United States Patent
Kim et al.

(10) Patent No.: US 12,227,498 B2
(45) Date of Patent: Feb. 18, 2025

(54) HETEROCYCLIC AMINE DERIVATIVE AND PHARMACEUTICAL COMPOSITION COMPRISING SAME

(71) Applicant: Daewoong Pharmaceutical Co., Ltd., Gyeonggi-do (KR)

(72) Inventors: Wol Young Kim, Gyeonggi-do (KR); Yeon Im Lee, Gyeonggi-do (KR); Youn Jung Yoon, Gyeonggi-do (KR); Joon Seok Park, Gyeonggi-do (KR); Deok Ki Eom, Gyeonggi-do (KR); Keuk-Chan Bang, Gyeonggi-do (KR); Jaehyun Jung, Gyeongsangnam-do (KR)

(73) Assignee: Daewoong Pharmaceutical Co., Ltd., Gyeonggi-do (KR)

( * ) Notice: Subject to any disclaimer, the term of this patent is extended or adjusted under 35 U.S.C. 154(b) by 755 days.

(21) Appl. No.: 17/269,325

(22) PCT Filed: Aug. 27, 2019

(86) PCT No.: PCT/KR2019/010894
§ 371 (c)(1),
(2) Date: Feb. 18, 2021

(87) PCT Pub. No.: WO2020/045941
PCT Pub. Date: Mar. 5, 2020

(65) Prior Publication Data
US 2022/0064155 A1  Mar. 3, 2022

(30) Foreign Application Priority Data

Aug. 27, 2018 (KR) .................. 10-2018-0100359
Aug. 26, 2019 (KR) .................. 10-2019-0104641

(51) Int. Cl.
| | |
|---|---|
| C07D 417/14 | (2006.01) |
| C07D 413/04 | (2006.01) |
| C07D 471/04 | (2006.01) |
| A61K 31/4427 | (2006.01) |
| A61K 31/4523 | (2006.01) |
| A61K 31/496 | (2006.01) |
| A61K 31/506 | (2006.01) |
| A61P 35/00 | (2006.01) |
| A61P 37/00 | (2006.01) |
| C07D 401/14 | (2006.01) |
| C07D 403/14 | (2006.01) |
| C07D 417/12 | (2006.01) |
| C07D 487/04 | (2006.01) |

(52) U.S. Cl.
CPC ......... *C07D 417/14* (2013.01); *C07D 413/04* (2013.01); *C07D 471/04* (2013.01)

(58) Field of Classification Search
CPC .. C07D 417/14; C07D 413/04; C07D 471/04; C07D 401/14; C07D 417/12; C07D 487/04; C07D 403/14; A61P 37/00; A61P 35/00; A61K 31/4427; A61K 31/4523; A61K 31/496; A61K 31/506
See application file for complete search history.

(56) References Cited

U.S. PATENT DOCUMENTS

| | | | |
|---|---|---|---|
| 7,897,600 | B2 | 3/2011 | Burkholder et al. |
| 9,987,276 | B2 | 6/2018 | Singh et al. |
| 11,149,019 | B2 | 10/2021 | Kim et al. |
| 11,339,167 | B2 | 5/2022 | Kim et al. |
| 2002/0137755 | A1 | 9/2002 | Bilodeau et al. |
| 2002/0147203 | A1 | 10/2002 | Bilodeau et al. |

(Continued)

FOREIGN PATENT DOCUMENTS

| | | |
|---|---|---|
| CA | 2853975 A1 | 5/2013 |
| CL | 200102242 | 1/2003 |

(Continued)

OTHER PUBLICATIONS

Office Action in AU Application No. 2019331328 dated Dec. 17, 2021, 8 pages.

(Continued)

*Primary Examiner* — Bruck Kifle
*Assistant Examiner* — Kevin S Martin
(74) *Attorney, Agent, or Firm* — MARSHALL, GERSTEIN & BORUN LLP

(57) ABSTRACT

The present disclosure relates to a novel heterocyclic amine derivative represented by the following Chemical Formula 1 and a pharmaceutical composition comprising the same, and the compound according to the present disclosure can be usefully used for the prevention or treatment of autoimmune diseases or cancers.

[Chemical Formula 1]

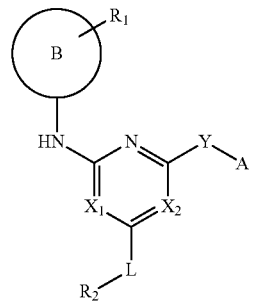

wherein, in Chemical Formula 1, $R_1$, $R_2$, $X_1$, $X_2$, L, Y, A and B are the same as defined in the specification.

18 Claims, No Drawings

(56) References Cited

U.S. PATENT DOCUMENTS

| | | |
|---|---|---|
| 2003/0064996 A1 | 4/2003 | Bilodeau et al. |
| 2004/0063720 A1 | 4/2004 | Bilodeau et al. |
| 2007/0225271 A1 | 9/2007 | Binggeli et al. |
| 2011/0117073 A1 | 5/2011 | Singh et al. |
| 2011/0230476 A1 | 9/2011 | Niu et al. |
| 2012/0071657 A1 | 3/2012 | Bebbington et al. |
| 2012/0172361 A1 | 7/2012 | Tao et al. |
| 2012/0277192 A1 | 11/2012 | Altman et al. |
| 2013/0190287 A1 | 7/2013 | Cianchetta et al. |
| 2014/0243290 A1 | 8/2014 | Altman et al. |
| 2015/0225422 A1 | 8/2015 | Bharathan et al. |
| 2016/0046608 A1 | 2/2016 | Cohen et al. |
| 2017/0073326 A1 | 3/2017 | Bharathan et al. |
| 2017/0174691 A1 | 6/2017 | Singh et al. |
| 2017/0233411 A1 | 8/2017 | Gray et al. |
| 2018/0118762 A1 | 5/2018 | Bharathan et al. |
| 2020/0079755 A1 | 3/2020 | Cianchetta et al. |
| 2020/0223821 A1 | 7/2020 | Kim et al. |
| 2023/0094404 A1 | 3/2023 | Kim et al. |

FOREIGN PATENT DOCUMENTS

| | | |
|---|---|---|
| CL | 201201627 | 5/2012 |
| CN | 1469874 A | 1/2004 |
| CN | 1469875 A | 1/2004 |
| CN | 102482277 A | 5/2012 |
| CN | 102573483 A | 7/2012 |
| CN | 102713618 A | 10/2012 |
| CN | 104628657 A | 5/2015 |
| CN | 105063001 A | 11/2015 |
| CN | 105916503 A | 8/2016 |
| CN | 112638910 A | 4/2021 |
| EA | 201490858 A1 | 8/2014 |
| EA | 201691421 A1 | 5/2017 |
| EP | 1103545 A1 | 5/2001 |
| EP | 1664025 A1 | 6/2006 |
| EP | 3845530 A1 | 7/2021 |
| JP | S5-5154971 A | 12/1980 |
| JP | H02-264775 A | 10/1990 |
| JP | 2003-509342 A | 3/2003 |
| JP | 2004-524282 A | 8/2004 |
| JP | 2017-503813 A | 2/2017 |
| KR | 2012-0034726 A | 4/2012 |
| KR | 2012-0093220 A | 8/2012 |
| KR | 2014-0113712 A | 9/2014 |
| KR | 2016-0002850 A | 1/2016 |
| KR | 2016-0122736 A | 10/2016 |
| KR | 20190040773 A | 4/2019 |
| KR | 20190104641 A | 9/2019 |
| KR | 20200024111 A | 3/2020 |
| RU | 2536584 C2 | 12/2014 |
| WO | WO-02/22602 A2 | 3/2002 |
| WO | WO-02/22603 A1 | 3/2002 |
| WO | WO-02/45652 A2 | 6/2002 |
| WO | WO-02/50071 A1 | 6/2002 |
| WO | WO-2005/056785 A2 | 6/2005 |
| WO | WO-2005/066335 A1 | 7/2005 |
| WO | WO-2006/124874 A2 | 11/2006 |
| WO | WO-2008/039218 A2 | 4/2008 |
| WO | WO-2008/060366 A2 | 5/2008 |
| WO | WO-2009/015254 A1 | 1/2009 |
| WO | WO-2010/144359 A1 | 12/2010 |
| WO | WO-2011-034907 A2 | 3/2011 |
| WO | WO-2011/110575 A1 | 9/2011 |
| WO | WO-2012/035055 A1 | 3/2012 |
| WO | WO-2012/115479 A2 | 8/2012 |
| WO | WO-2013050438 A1 | 4/2013 |
| WO | WO-2013/102431 A1 | 7/2013 |
| WO | WO-2014/036016 A1 | 3/2014 |
| WO | WO-2014/048065 A1 | 4/2014 |
| WO | WO-2014/055934 A2 | 4/2014 |
| WO | WO-2014/177524 A1 | 11/2014 |
| WO | WO-2014181137 A1 | 11/2014 |
| WO | WO-2015/025197 A1 | 2/2015 |
| WO | WO-2015/061247 A2 | 4/2015 |
| WO | WO-2015/108861 A1 | 7/2015 |
| WO | WO-2016/001341 A1 | 1/2016 |
| WO | WO-2016/065138 A1 | 4/2016 |
| WO | WO-2016105582 A1 | 6/2016 |
| WO | WO-2016/177347 A1 | 11/2016 |
| WO | WO-2018088780 A1 | 5/2018 |
| WO | WO-2019/074275 A1 | 4/2019 |
| WO | WO-2020045941 A1 | 3/2020 |
| WO | WO-2020/127200 A1 | 6/2020 |
| WO | WO-2020123675 A1 | 6/2020 |
| WO | WO-2021172922 A1 | 9/2021 |
| WO | WO-2022071772 A1 | 4/2022 |
| WO | WO-2022199599 A1 | 9/2022 |

OTHER PUBLICATIONS

Office Action in BR Application No. 1120210036520 dated Nov. 4, 2021, 10 pages.

Viira et al., "Design, Discovery, Modeling, Synthesis, and Biological Evaluation of Novel and Small, Low Toxicity s-triazine Derivatives as HIV-1 Non-nucleoside Reverse Transcriptase Inhibitors", Bioorganic & Medicinal Chemistry 24, 2016, pp. 2519-2529.

Harling et al., "Discovery of Novel Irreversible Inhibitors of Interleukin (IL)-2-inducible Tyrosine Kinase (Itk) by Targeting Cysteine 442 in the ATP Pocket", The Journal of Biological Chemistry, vol. 288 (39), Sep. 27, 2013, pp. 28195-28206.

Search Report and Written Opinion in SG Application No. 11202101451Q dated Dec. 27, 2021, 10 pages.

CAS Registry No. 2217212-09-2; STN Entry Date: Apr. 22, 2018; 1-[3-[4-methyl-6-[(5-methyl-2-thiazolyl)amino]-2-pyrimidinyl]-1-piperidinyl]-ethanone.

CAS Registry No. 2217211-96-4; STN Entry Date: Apr. 22, 2018; 1-[3-[4-methyl-6-(2-thiazolylamino)-2-pyrimidinyl]-1-pyrrolidinyl]-ethanone.

CAS Registry No. 2216847-73-1; STN Entry Date: Apr. 22, 2018; 1-[3-[4-methyl-6-(2-thiazolylamino)-2-pyrimidinyl]-1-piperidinyl]-ethanone.

CAS Registry No. 2215529-68-1; STN Entry Date: Apr. 19, 2018; 1-[3-[4-methyl-6-[(5-methyl-2-thiazolyl)amino]-2-pyrimidinyl]-1-pyrrolidinyl]-ethanone.

CAS Registry No. 2060394-15-0; STN Entry Date: Jan. 27, 2017; 1-[3-[4-methyl-6-[(4-methyl-2-thiazolyl)amino]-2-pyrimidinyl]-1-pyrrolidinyl]-ethanone.

CAS Registry No. 2060313-11-1; STN Entry Date: Jan. 27, 2017; 1-[3-[4-methyl-6-[(4-methyl-2-thiazolyl)amino]-2-pyrimidinyl]-1-piperidinyl]-ethanone.

CAS Registry No. 1381110-02-6; STN Entry Date: Jul. 4, 2012; 1-[3-[4-methyl-6-(2-pyrazinylamino)-2-pyrimidinyl]-1-pyrrolidinyl]-ethanone.

CAS Registry No. 1381108-65-1; STN Entry Date: Jul. 4, 2012; 1-[3-[4-methyl-6-(2-pyridinylamino)-2-pyrimidinyl]-1-piperidinyl]-ethanone.

CAS Registry No. 1381084-36-1; STN Entry Date: Jul. 4, 2012; 1-[3-[4-methyl-6-(2-pyrimidinylamino)-2-pyrimidinyl]-1-pyrrolidinyl]-ethanone.

CAS Registry No. 1381039-22-0; STN Entry Date: Jul. 4, 2012; 1-[3-[4-methyl-6-(2-pyrimidinylamino)-2-pyrimidinyl]-1-piperidinyl]-ethanone.

CAS Registry No. 1380968-78-4; STN Entry Date: Jul. 4, 2012; 1-[3-[4-methyl-6-[(3-methyl-2-pyridinyl)amino]-2-pyrimidinyl]-1-ethanone.

CAS Registry No. 1380963-03-0; STN Entry Date: Jul. 4, 2012; 1-[3-[4-methyl-6-[(3-methyl-2-pyridinyl)amino]-2-pyrimidinyl]-1-ethanone.

CAS Registry No. 1380946-82-6; STN Entry Date: Jul. 4, 2012; 1-[3-[4-methyl-6-[(6-methyl-2-pyridinyl)amino]-2-pyrimidinyl]-1-ethanone.

CAS Registry No. 1380850-66-7; STN Entry Date: Jul. 3, 2012; 1-[3-[4-methyl-6-[(6-methyl-2-pyridinyl)amino]-2-pyrimidinyl]-1-ethanone.

CAS Registry No. 1380832-77-8; STN Entry Date: Jul. 3, 2012; 1-[3-[4-methyl-6-(2-yridinylamino)-2-pyrimidinyl]-1-pyrrolidinyl]-ethanone.

(56) References Cited

OTHER PUBLICATIONS

CAS Registry No. 2125584-76-9; STN Entry Date: Sep. 6, 2017; 1-[3-[4-methyl-6-(2-pyrazinylamino)-2-pyrimidinyl]-1-piperidinyl]-2-propen-1-one.
CAS Registry No. 1381087-34-8; STN Entry Date: Jul. 4, 2012; 1-[3-[4-methyl-6-(1,3,4-thiadiazol-2-ylamino)-2-pyrimidinyl]-1-ethanone.
CAS Registry No. 1380963-14-3; STN Entry Date: Jul. 4, 2012; 1-[3-[4-methyl-6-[(5-methyl-3-isoxazolyl)amino]-2-pyrimidinyl]-1-ethanone.
CAS Registry No. 1381015-39-9; STN Entry Date: Jul. 4, 2012; 1-[3-[4-[(5-ethyl-1,3,4-thiadiazol-2-yl)amino]-6-methyl-2-pyrimidinyl]-1-pyrrolidinyl]-ethanone.
Das, J. et al. "Discovery and SAR of 2-amino-5-(thioaryl) Thiazoles as Potent and Selective ITK inhibitors." *Bioorganic & Medicinal Chemistry Letters 16*, No. 14 (2006): 3706-3712.
Bugatti et al., "B Cells in Rheumatoid Arthritis: From Pathogenic Players to Disease Biomarkers" Biomed Res Int. (2014) 2014:681678, 15 pages.
CAS Registry No. 1380832-77-8; STN Entry Date: Jul. 3, 2012; 1-[3-[4-methyl-6-(2-yridinylamino)-2-pyrimidinyl]-1-pyrrolidinyl]-ethanone. 1 page.
CAS Registry No. 1380850-66-7; STN Entry Date: Jul. 3, 2012; 1-[3-[4-methyl-6-[(6-methyl-2-pyridinyl)amino]-2-pyrimidinyl]-1-ethanone. 1 page.
CAS Registry No. 1380946-82-6; STN Entry Date: Jul. 4, 2012; 1-[3-[4-methyl-6-[(6-methyl-2-pyridinyl)amino]-2-pyrimidinyl]-1-ethanone. 1 page.
CAS Registry No. 1380963-03-0; STN Entry Date: Jul. 4, 2012; 1-[3-[4-methyl-6-[(3-methyl-2-pyridinyl)amino]-2-pyrimidinyl]-1-ethanone. 1 page.
CAS Registry No. 1380963-14-3; STN Entry Date: Jul. 4, 2012; 1-[3-[4-methyl-6-[(5-methyl-3-isoxazolyl)amino]-2-pyrimidinyl]-1-ethanone. 1 page.
CAS Registry No. 1380968-78-4; STN Entry Date: Jul. 4, 2012; 1-[3-[4-methyl-6-[(3-methyl-2-pyridinyl)amino]-2-pyrimidinyl]-1-ethanone. 1 page.
CAS Registry No. 1381015-39-9; STN Entry Date: Jul. 4, 2012; 1-[3-[4-[(5-ethyl-1 , 3 , 4-thiadiazol-2-yl)amino]-6-methyl-2-pyrimidinyl]-1-pyrrolidinyl]-ethanone. 1 page.
CAS Registry No. 1381039-22-0; STN Entry Date: Jul. 4, 2012; 1-[3-[4-methyl-6-(2-pyrimidinylamino)-2-pyrimidinyl]-1-piperidinyl]-ethanone. 1 page.
CAS Registry No. 1381084-36-1; STN Entry Date: Jul. 4, 2012; 1-[3-[4-methyl-6-(2-pyrimidinylamino)-2-pyrimidinyl]-1-pyrrolidinyl]-ethanone. 1 page.
CAS Registry No. 1381087-34-8; STN Entry Date: Jul. 4, 2012; 1-[3-[4-methyl-6-(1,3,4-thiadiazol-2-ylamino)-2-pyrimidinyl]-1-ethanone. 1 page.
CAS Registry No. 1381108-65-1; STN Entry Date: Jul. 4, 2012; 1-[3-[4-methyl-6-(2-pyridinylamino)-2-pyrimidinyl]-1-piperidinyl]-ethanone. 1 page.
CAS Registry No. 1381110-02-6; STN Entry Date: Jul. 4, 2012; 1-[3-[4-methyl-6-(2-pyrazinylamino)-2-pyrimidinyl]-1-pyrrolidinyl]-ethanone. 1 page.
CAS Registry No. 2060313-11-1; STN Entry Date: Jan. 27, 2017; 1-[3-[4-methyl-6-[(4-methyl-2-thiazolyl)amino]-2-pyrimidinyl]-1-piperidinyl]-ethanone. 1 page.
CAS Registry No. 2060394-15-0; STN Entry Date: Jan. 27, 2017; 1-[3-[4-methyl-6-[(4-methyl-2-thiazolyl)amino]-2-pyrimidinyl]-1-pyrrolidinyl]-ethanone. 1 page.
CAS Registry No. 2125584-76-9; STN Entry Date: Sep. 6, 2017; 1-[3-[4-methyl-6-(2-pyrazinylamino)-2-pyrimidinyl]-1-piperidinyl]-2-propen-1-one. 1 page.
CAS Registry No. 2215529-68-1; STN Entry Date: Apr. 19, 2018; 1-[3-[4-methyl-6-[(5-methyl-2-thiazolyl)amino]-2-pyrimidinyl]-1-ethanone. 1 page.
CAS Registry No. 2216847-73-1; STN Entry Date: Apr. 22, 2018; 1-[3-[4-methyl-6-(2-thiazolylamino)-2-pyrimidinyl]-1-piperidinyl]-ethanone. 1 page.
CAS Registry No. 2217211-96-4; STN Entry Date: Apr. 22, 2018; 1-[3-[4-methyl-6-(2-thiazolylamino)-2-pyrimidinyl]-1-pyrrolidinyl]-ethanone. 1 page.
CAS Registry No. 2217212-09-2; STN Entry Date: Apr. 22, 2018; 1-[3-[4-methyl-6-[(5-methyl-2-thiazolyl)amino]-2-pyrimidinyl]-1-piperidinyl]-ethanone. 1 page.
International Search Report and Written Opinion in International Application No. PCT/KR2021/002440 dated Jun. 4, 2021, 13 pages.
Office Action in Korean Application No. KR1020210025655 dated Jan. 16, 2023, 5 pages.
Written Opinion of the Intellectual Property Office of Singapore mailed on May 15, 2023, for SG Application No. 11202101451Q, 8 pages.
Office Action in CN Application No. 201980056437.8 dated May 4, 2023, 16 pages.
Office Action in KR Application No. 10-2019-0104641 dated Sep. 16, 2021, 8 pages.
Leipe et al., "Role of Th17 Cells in Human Autoimmune Arthritis", Arthritis & Rheumatism, vol. 62, No. 10, Oct. 2010, pp. 2876-2885.
Sahu et al., ITK Inhibitors in Inflammation and Immune-Mediated Disorders, Current Topics in Medicinal Chemistry, vol. 9, 2009, pp. 690-703.
Fowell et al., "Impaired NFATc Translocation and Failure of Th2 Development in Itk-Deficient CD4+ T Cells", Immunity, vol. 11, Oct. 1999, pp. 399-409.
Zhong et al., "Targeting Interleukin-2-inducible T-cell Kinase (ITK) and Resting Lymphocyte Kinase (RLK) Using a Novel Covalent Inhibitor PRN694", The Journal of Biological Chemistry, vol. 290, No. 10, Mar. 6, 2015, pp. 5960-5978.
Ho Yin Lo, "Itk Inhibitors: a Patent Review", Expert Opinion on Therapeutic Patents, vol. 20, Issue 4, 2010, pp. 459-469.
Schaeffer et al., "Mutation of Tec Family Kinases Alters T Helper Cell Differentiation", Nature Immunology, vol. 2, No. 12, Dec. 2001, pp. 1183-1188.
Iwaki et al., "Btk Plays a Crucial Role in the Amplification of FcεRI-mediated Mast Cell Activation by Kit", The Journal of Biological Chemistry, vol. 280, No. 48, Dec. 2, 2005, pp. 40261-40270.
Horwood et al., "Bruton's Tyrosine Kinase is Required for Lipopolysaccharide-induced Tumor Necrosis Factor α Production", The Journal of Experimental Medicine, vol. 197, No. 12, Jun. 16, 2003, pp. 1603-1611.
Gomez-Rodriguez et al., "Itk-mediated Integration of T Cell Receptor and Cytokine Signaling Regulates the Balance Between Th17 and Regulatory T Cells", The Journal of Experimental Medicine, vol. 211, No. 3, Feb. 17, 2014, pp. 529-543.
Search Report and Written Opinion in PCT/KR2019/010894 dated Dec. 9, 2019, 12 pages.
Alder et al., "Identification of a Novel and Selective Series of Itk Inhibitors via a Template-Hopping Strategy", ACS Med. Chem. Lett, vol. 4, 2013, pp. 948-952.
Takayama et al., "Profiling of Chiral and Achiral Carboxylic Acid Metabolomics: Synthesis and Evaluation of Triazine-type Chiral Derivatization Reagents for Carboxylic Acids by LC-ESI-MS/MS and the Application to Saliva of Healthy Volunteers and Diabetic Patients", Anal Bioanal Chem, vol. 407, 2015, pp. 1003-1014.
Shinde et al., "Synthesis of Novel Substituted 4,6-Dimethoxy-N-phenyl-1,3,5-triazin-2-amine Derivatives and Their Antibacterial and Antifungal Activities", Asian Journal of Chemistry, vol. 27, No. 11, 2015, pp. 4130-4134.
Trani et al., "Design, Synthesis and Structure-activity Relationships of a Novel Class of Sulfonylpyridine Inhibitors of Interleukin-2 Inducible T-cell Kinase (ITK)", Bioorganic & Medicinal Chemistry Letters, vol. 24, 2014, pp. 5818-5823.
Couderchet et al., "Pigments as Biomarkers of Exposure to the Vineyard Herbicide Flazasulfuron in Freshwater Algae", Ecotoxicology and Environmental Safety, vol. 55, 2003, pp. 271-277.
Bertrand et al., "Flazasulfuron: Alcoholysis, Chemical Hydrolysis, and Degradation on Various Minerals", J. Agric. Food Chem, vol. 51, 2003, pp. 7717-7721.
Vinod et al., "Development of an Efficient, Scalable Route for the Preparation of a Novel Insulin-Like Growth Factor-1 Receptor Modulator", Organic Process Research & Development, vol. 16, 2012, pp. 1416-1421.

(56) References Cited

OTHER PUBLICATIONS

Zhang et al., "Palladium-catalyzed Cross-coupling of Electron-deficient Heteroaromatic Amines With Heteroaryl Halides", Synthetic Communications, vol. 43, 2013, pp. 456-463.
Office Action in CL Application No. 421-2021 dated Feb. 14, 2022.
Extended European Search Report in EP Application No. 19855534.4 dated Mar. 25, 2022, 8 pages.
Office Action in JP Application No. 2021-534102 dated Mar. 29, 2022, 9 pages.
Examiner's Report in CA Application No. 3,108,856 dated Apr. 1, 2022, 4 pages.
Office Action in KZ Application No. 2021/0179.1 dated May 2, 2022, 6 pages.
Extended European Search Report mailed on Feb. 9, 2024, for EP Application No. 21761001.3, 7 pages.

HETEROCYCLIC AMINE DERIVATIVE AND PHARMACEUTICAL COMPOSITION COMPRISING SAME

TECHNICAL FIELD

Cross-Reference to Related Application(s)

This application is a National Stage Entry of International Application PCT/KR2019/010894 filed on Aug. 27, 2019, which claims the benefit of Korean Patent Application No. 10-2018-0100359 filed on Aug. 27, 2018 and Korean Patent Application No. 10-2019-0104641 filed on Aug. 26, 2019 with the Korean Intellectual Property Office, each of which is incorporated herein by reference in their entireties.

The present disclosure relates to a novel heterocyclic amine useful as BTK (Bruton's Tyrosine Kinase) inhibitor and a pharmaceutical composition comprising the same.

Background of Art

ITK (Interleukin-2 Tyrosine Kinase) and BTK (Bruton's Tyrosine Kinase) are a type of tyrosine kinase, together with Tec (tyrosine kinase expressed in hepatocellular carcinoma), RLK (Resting Lymphocyte Kinase) and BMX (Bone-Marrow tyrosine kinase gene on chromosome X), which that does not have a TEC family receptor and acts on various immune responses.

ITK is expressed not only in T cells but also in NK cells and mast cells, and plays an important role in T-cell proliferation and production of important cytokines such as IL-2, IL-4, IL-5, IL-10, IL-13 and IL-17 (Schaeffer et al. Nat. Immune 2001, 2, 1183; Fowell et al. Immunity, 1999, 11, 399). T cells are activated by TCR signaling, and the activated T cells produce inflammatory cytokine and activate B cells and macrophages, causing autoimmune diseases such as RA (Sahu N. et al. Curr Top Med Chem. 2009, 9, 690). Previously, it was known that T cells are activated into Th1 cells to induce RA diseases, but recently, it has been reported that not only Th17/Treg but also Th1 cells act as a pathogenesis of RA (J Leipe J. et al. Arthritis Rheum. 2010, 62, 2876). In addition, the ITK has been previously developed as an immunotherapeutic drug target such as asthma, but no ITK has been developed as a therapeutic for RA (Lo H. Y Expert Opin Ther Pat. 2010, 20, 459). Recently, however, it has been reported to regulate the development of Th17 and Treg cells via ITK−/−mice, and it has ample potential as a therapeutic target for RA (Gomez-Rodriguez J. et al. J. Exp. Med. 2014, 211, 529).

In a study using the ITK inhibitor PRN694, a study on the reduction of TNF-α, which is a representative inflammatory cytokine of RA diseases, have been reported, confirming the possibility of development as a therapeutic agent by regulating Th17 expression via ITK inhibition (Zhong Y. et al. THE JOURNAL OF BIOLOGICAL CHEMISTRY 2015, 290, 5960).

BTK acts as a regulator of early B-cell development as well as of mature B-cell activation, signaling and survival. The B-cell is signaled by a B cell receptor (BCR) that recognizes an antigen attached to the surface of an antigen-presenting cell and is activated into a mature antibody-producing cell. However, aberrant signaling via BCR leads to abnormal B-cell proliferation and the formation of pathologic autoantibodies, and thereby can induce cancer, autoimmune and/or inflammatory diseases. Thus, in the abnormal B-cell proliferation, signaling via BCR may be blocked when BTK is deficient. Thus, inhibition of BTK can block B-cell mediated disease processes, and the use of BTK inhibitors may be a useful approach for the treatment of B-cell mediated diseases.

Furthermore, BTK can be expressed by other cells that may be associated with disease besides B-cells. For example, BTK is important components for Fc-gamma signaling in bone marrow cells, and is expressed by mast cells. Specifically, BTK-deficient bone marrow-induced mast cells exhibit impaired antigen-induced degranulation, and inhibition of BTK activity is known to be useful for treating pathological mast cell responses such as allergy and asthma (Iwaki et al. J. Biol Chem. 2005 280:40261). In addition, it is known that monocytes from XLA patients, in which BTK activity is absent, decreases in TNF alpha production following stimulation and thus TNF alpha-mediated inflammation could be inhibited by BTF inhibitors (see, Horwood et al., J. Exp. Med. 197:1603, 2003).

At present, there has been no case where it has been developed as a substance that dually inhibits BTK and ITK. However, as the BTK inhibitor, WO 2008/039218 discloses 4-aminopyrazolo[3,4-d]pyrimidinylpiperidine derivatives, and WO2015/061247 discloses hetero compounds such as pyridine, pyrimidine, pyrazine and pyridazine, and WO2014/055934 discloses pyrimidinyl phenyl acrylamide derivatives. As the ITK inhibitor, WO2005/066335 discloses aminobenzimidazoles, WO2005/056785 discloses pyridones, WO2002/050071 discloses aminothiazole derivatives, and recently, WO2014/036016 discloses benzimidazole derivatives.

In view of the above, as a result of studying novel compounds, the present inventors has found that a compound having a chemical structure different from BTK, ITK inhibitors reported so far has excellent BTK and ITK dual-activity inhibitory effect, thereby completing the present disclosure. The compounds belonging to the present disclosure mainly have BTK and ITK inhibitory activity on their own, but do not exclude a possibility of exhibiting a pharmacological action as an efficacious agent by a special body environment or by products of metabolic process, after absorption into the body.

DETAILED DESCRIPTION OF THE INVENTION

Technical Problem

It is one object of the present disclosure to provide a novel heterocyclic amine derivative useful as a BTK inhibitor, and a pharmaceutical composition comprising the same.

Technical Solution

In order to achieve the above objects, there is provided a compound represented by the following Chemical Formula 1, or a pharmaceutically acceptable salt thereof:

[Chemical Formula 1]

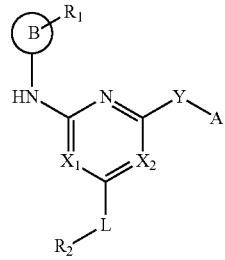

wherein, in Chemical Formula 1,

B is a 5-membered or 6-membered heterocycle containing 1 to 3 heteroatoms each independently selected from the group consisting of N, O and S, provided that the 5-membered or 6-membered heterocycle includes at least one N, $R_1$ is hydrogen, halogen, $C_{1-4}$ alkyl, or $C_{1-4}$ haloalkyl, $X_1$ and $X_2$ are each independently N, or CR',
  wherein R' is hydrogen or halogen, L is a bond, $C_{1-4}$ alkylene, or —O—, $R_2$ is cyano; $C_{1-4}$ alkyl; $C_{6-10}$ aryl; pyridinyl; morpholino; piperazinyl; or piperidinyl,
  wherein, the piperazinyl and the piperidinyl are each independently, unsubstituted, or substituted with $C_{1-4}$ alkyl, $C_{1-4}$ alkyl substituted with cyano, $C_{1-4}$ alkyl substituted with amino, $C_{1-4}$ alkyl substituted with $C_{1-4}$ alkoxy, or —CO—($C_{1-4}$ alkyl), Y is a bond, —O—, —NH—, or —N($C_{1-4}$ alkyl)-, A is $C_{1-4}$ alkyl,

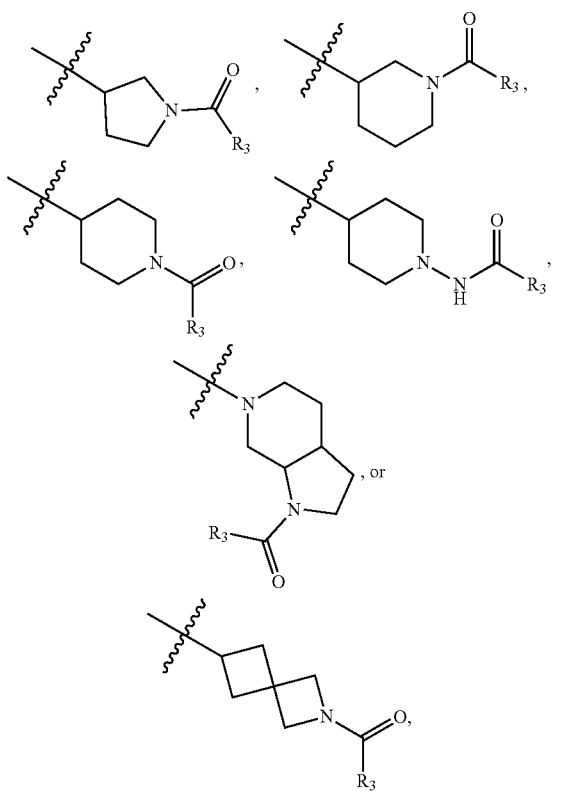

wherein $R_3$ is $C_{1-4}$ alkyl, $C_{1-4}$ haloalkyl, $C_{2-4}$ alkenyl, $C_{2-4}$ haloalkenyl, $C_{2-4}$ alkynyl, or $C_{2-4}$ haloalkynyl.

Preferably, B is thiazole, pyrazole, pyridine, or pyrimidine ring, and $R_1$ is hydrogen, chloro, methyl, or trifluoromethyl.

Preferably,
both $X_1$ and $X_2$ are CH;
one of $X_1$ and $X_2$ is CF and the other is CH; or
one of $X_1$ and $X_2$ is N and the other is CH.

More preferably,
both $X_1$ and $X_2$ are CH, or
$X_1$ is CH and $X_2$ is CF; or
$X_1$ is CH and $X_2$ is N; or
$X_1$ is N and $X_2$ is CH.

Preferably, L is a bond, methylene, or —O—.

Preferably, $R_2$ is cyano; methyl; phenyl; pyridinyl; morpholino; piperazinyl substituted with methyl; piperazinyl substituted with ethyl; piperazinyl substituted with 2-cyanoethyl; piperazinyl substituted with 3-aminopropyl; piperazinyl substituted with 2-methoxyethyl; piperazinyl substituted with —CO-(methyl); unsubstituted piperidinyl; or piperidinyl substituted with methyl.

Preferably, Y is a bond, —O—, —NH—, or —N(methyl)-.

Preferably, $R_3$ is —$CH_2CH_2Cl$, —CH=$CH_2$, —CH=$CHCH_3$, —CH=CHCl, —C≡CH, or —C≡$CCH_3$.

Preferably, the compound represented by Chemical Formula 1 is represented by the following Chemical Formula 1-1:

[Chemical Formula 1-1]

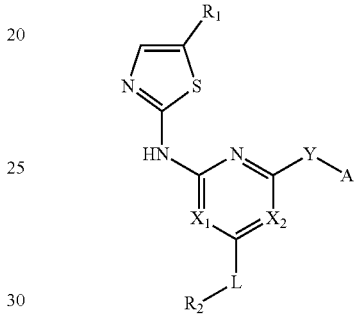

wherein, in Chemical Formula 1-1, $R_1$ is hydrogen, $C_{1-4}$ alkyl, or $C_{1-4}$ haloalkyl, $X_1$ and $X_2$ are each independently N, or CR',
  wherein R' is hydrogen or halogen, L is a bond, $C_{1-4}$ alkylene, or —O—, $R_2$ is cyano; $C_{1-4}$ alkyl; $C_{6-10}$ aryl; pyridinyl; morpholino; piperazinyl; or piperidinyl,
  wherein the piperazinyl and the piperidinyl are each independently, unsubstituted, or substituted with $C_{1-4}$ alkyl, $C_{1-4}$ alkyl substituted with cyano, $C_{1-4}$ alkyl substituted with amino, $C_{1-4}$ alkyl substituted with $C_{1-4}$ alkoxy, or —CO—($C_{1-4}$ alkyl), Y is a bond, —O—, —NH—, or —N($C_{1-4}$ alkyl)-, A is $C_{1-4}$ alkyl,

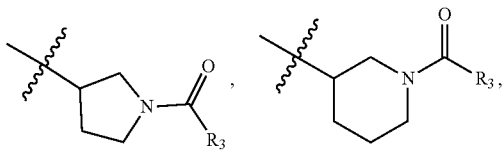

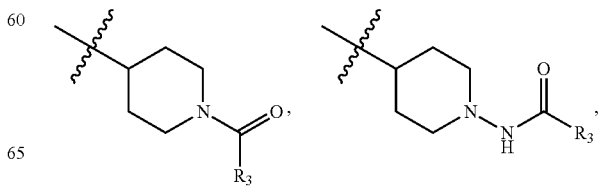

-continued

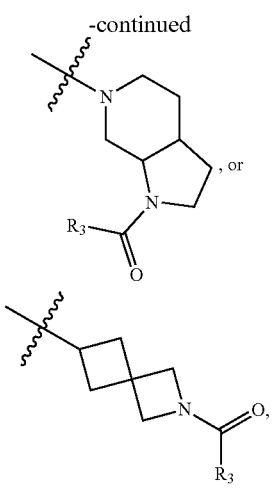

wherein, $R_3$ is $C_{1-4}$ haloalkyl, $C_{2-4}$ alkenyl, $C_{2-4}$ haloalkenyl, or $C_{2-4}$ alkynyl.

Preferably, in Chemical Formula 1-1,
$R_1$ is $C_{1-4}$ alkyl,
$X_1$ and $X_2$ are each independently N or CH,
L is a bond, $C_{1-4}$ alkylene, or —O—,
$R_2$ is cyano; $C_{1-4}$ alkyl; $C_{6-10}$ aryl; pyridinyl; morpholino; piperazinyl; or piperidinyl,
  wherein, the piperazinyl and the piperidinyl are each independently, unsubstituted, or substituted with $C_{1-4}$ alkyl, $C_{1-4}$ alkyl substituted with cyano, $C_{1-4}$ alkyl substituted with $C_{1-4}$ alkoxy, or —CO—($C_{1-4}$ alkyl),
Y is a bond, —O—, —NH—, or —N($C_{1-4}$ alkyl)-, A is

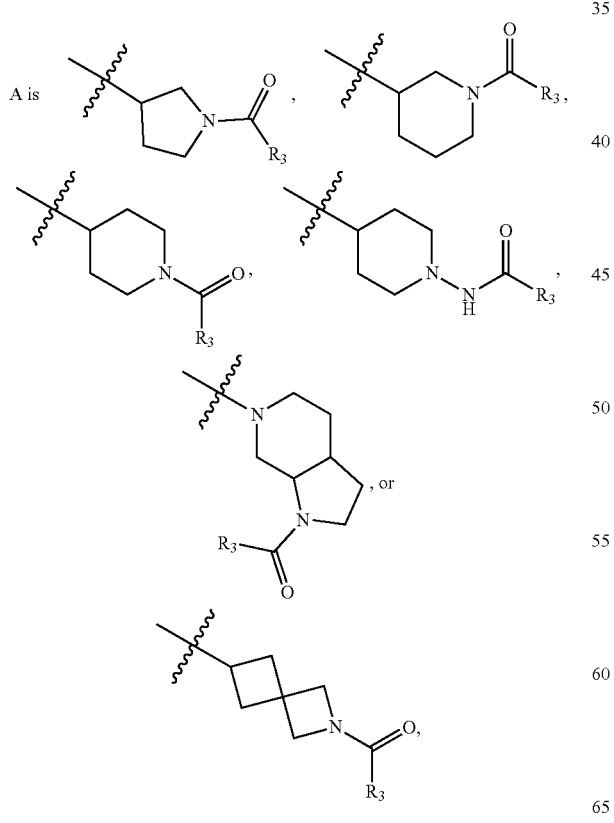

wherein, $R_3$ is $C_{2-4}$ alkenyl, or $C_{2-4}$ alkynyl.

Also preferably, the compound represented by Chemical Formula 1 is represented by the following Chemical Formula 1-2:

[Chemical Formula 1-2]

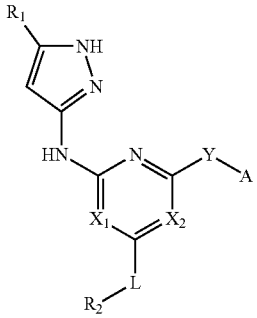

wherein, in Chemical Formula 1-2,
$R_1$ is hydrogen, or halogen,
$X_1$ and $X_2$ are each independently N, or CH,
L is $C_{1-4}$ alkylene,
$R_2$ is morpholino,
Y is —NH—,
A is

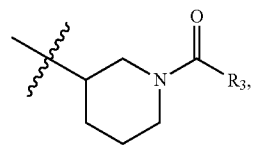

wherein, $R_3$ is $C_{2-4}$ alkenyl.

Further, preferably, the compound represented by Chemical Formula 1 is represented by the following Chemical Formula 1-3:

[Chemical Formula 1-3]

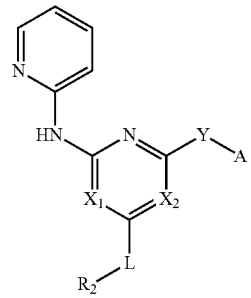

wherein, in Chemical Formula 1-3,
$X_1$ and $X_2$ are each independently N or CH,
L is $C_{1-4}$ alkylene,
$R_2$ is morpholino,
Y is —NH—,

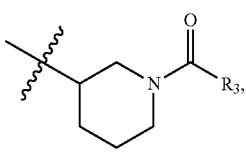

A is wherein, $R_3$ is $C_{2-4}$ alkenyl.

Further, preferably, the compound represented by Chemical Formula 1 is represented by the following Chemical Formula 1-4:

[Chemical Formula 1-4]

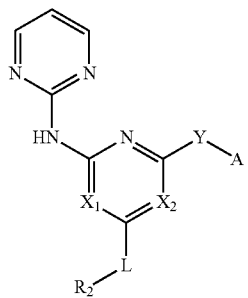

wherein, in Chemical Formula 1-4,
$X_1$ and $X_2$ are each independently N or CH,
L is $C_{1-4}$ alkylene,
$R_2$ is morpholino,
Y is —NH—,
A is

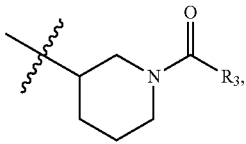

wherein, $R_3$ is $C_{2-4}$ alkenyl.

In addition, the compounds of the present disclosure may exist in the form of salts, especially pharmaceutically acceptable salts. As salts, salts commonly used in the art, such as acid addition salts formed by pharmaceutically acceptable free acids can be used without limitation. The term "pharmaceutically acceptable salt" as used herein refers to any organic or inorganic addition salt of the compound represented by Chemical Formula 1, whose concentration is relatively non-toxic and harmless to a patient and activates effectively and whose side effects do not degrade the beneficial efficacy of the above compound.

As the free acid, an organic acid and an inorganic acid can be used. Examples of the inorganic acids include hydrochloric acid, phosphoric acid, sulfuric acid, nitric acid, tartaric acid and the like. Examples of the organic acids include methanesulfonic acid, p-toluenesulfonic acid, acetic acid, trifluoroacetic acid, maleic acid, succinic acid, oxalic acid, benzoic acid, tartaric acid, fumaric acid, mandelic acid, propionic acid, citric acid, lactic acid, glycollic acid, gluconic acid, galacturonic acid, glutamic acid, glutaric acid, glucuronic acid, aspartic acid, ascorbic acid, carbonic acid, vanillic acid, hydroiodic acid and the like, but are not limited thereto. Preferably, the salt may be a hydrochloride salt.

Further, a pharmaceutically acceptable metal salt can be obtained by a conventional method using a base. For example, the compound represented by Chemical Formula 1 is dissolved in an excessive amount of an alkali metal hydroxide or an alkaline earth metal hydroxide solution, the non-soluble salt is filtered, and then the filtrate is evaporated and dried to obtain a pharmaceutically acceptable metal salt. At this time, it is particularly preferable to prepare a sodium salt, a potassium salt or a calcium salt as the metal salt.

In addition, a pharmaceutically unacceptable salt or solvate of the compound of Chemical Formula 1 may be used as an intermediate when preparing the compound of Chemical Formula 1, or the pharmaceutically acceptable salt or the solvate thereof.

Further, the compound represented by Chemical Formula 1 according to the present disclosure includes not only pharmaceutically acceptable salts thereof, but also solvates such as hydrates that can be prepared therefrom, and includes all possible stereoisomers, without being limited thereto. The solvate and the stereoisomer of the compound represented by Chemical Formula 1 may be prepared from the compound of Chemical Formula 1 using common methods known in the art.

Further, the compound represented by Chemical Formula 1 according to the present disclosure may be prepared either in a crystalline form or in a non-crystalline form, and when the compound of Chemical Formula 1 is prepared in a crystalline form, it may be optionally hydrated or solvated. In the present disclosure, the compound represented by Chemical Formula 1 may not only include a stoichiometric hydrate, but also include a compound containing various amounts of water. The solvate of the compound represented by Chemical Formula 1 according to the present disclosure includes both stoichiometric solvates and non-stoichiometric solvates.

Representative examples of the compound represented by Chemical Formula 1 or a pharmaceutically acceptable salt thereof are as follows:

1) 1-(3-((6-((5-methylthiazol-2-yl) amino)-4-(morpholinomethyl) pyridin-2-yl) amino) piperidin-1-yl) prop-2-en-1-one,
2) 1-(3-((6-((5-methylthiazol-2-yl) amino)-4-(morpholinomethyl) pyridin-2-yl) amino) pyrrolidin-1-yl) prop-2-en-1-one,
3) 1-(4-((6-((5-methylthiazol-2-yl) amino)-4-(morpholinomethyl) pyridin-2-yl) amino) piperidin-1-yl) prop-2-en-1-one,
4) (R)-1-(3-((6-((5-methylthiazol-2-yl) amino)-4-(morpholinomethyl) pyridin-2-yl) amino) piperidin-1-yl) prop-2-en-1-one,
5) (S)-1-(3-((6-((5-methylthiazol-2-yl) amino)-4-(morpholinomethyl) pyridin-2-yl) amino) piperidin-1-yl) prop-2-en-1-one,
6) (R)-1-(3-((6-((5-methylthiazol-2-yl) amino)-4-(morpholinomethyl) pyridin-2-yl) amino) pyrrolidin-1-yl) prop-2-en-1-one,
7) (S)-1-(3-((6-((5-methylthiazol-2-yl) amino)-4-(morpholinomethyl) pyridin-2-yl) amino) pyrrolidin-1-yl) prop-2-en-1-one,
8) 1-(3-((2-((5-methylthiazol-2-yl) amino)-6-(morpholinomethyl) pyrimidin-4-yl) amino) pyrrolidin-1-yl) prop-2-en-1-one,
9) (E)-1-(3-((2-((5-methylthiazol-2-yl) amino)-6-(morpholinomethyl) pyrimidin-4-yl) amino) pyrrolidin-1-yl) but-2-en-1-one, 10) 1-(3-((6-((5-methylthiazol-2-yl) amino)-4-(morpholinomethyl) pyridin-2-yl) oxy) pyrrolidin-1-yl) prop-2-en-1-one,
11) 1-(4-((6-((5-methylthiazol-2-yl) amino)-4-(morpholinomethyl) pyridin-2-yl) oxy) piperidin-1-yl) prop-2-en-1-one,
12) 1-(3-((6-((5-methylthiazol-2-yl) amino)-4-(morpholinomethyl) pyridin-2-yl) oxy) piperidin-1-yl) prop-2-en-1-one,
13) (R)-1-(3-((6-((5-methylthiazol-2-yl) amino)-4-(morpholinomethyl) pyridin-2-yl) amino) piperidin-1-yl) but-2-yn-1-one,
14) 1-(3-((6-((5-methylthiazol-2-yl) amino)-4-(morpholinomethyl) pyridin-2-yl) amino) pyrrolidin-1-yl) but-2-yn-1-one,
15) (S)-1-(3-((6-((5-methylthiazol-2-yl) amino)-4-(morpholinomethyl) pyridin-2-yl) oxy) piperidin-1-yl) prop-2-en-1-one,
16) (R)-1-(3-((6-((5-methylthiazol-2-yl) amino)-4-(morpholinomethyl) pyridin-2-yl) oxy) piperidin-1-yl) prop-2-en-1-one,
17) 1-(3-((4-((5-methylthiazol-2-yl) amino)-6-(morpholinomethyl) pyrimidin-2-yl) amino) piperidin-1-yl) prop-2-en-1-one,
18) (S)-1-(3-((6-((5-methylthiazol-2-yl) amino)-4-(morpholinomethyl) pyridin-2-yl) amino) piperidin-1-yl) but-2-yn-1-one,
19) 1-(4-((6-((5-methylthiazol-2-yl) amino)-4-(morpholinomethyl) pyridin-2-yl) amino) piperidin-1-yl) but-2-yn-1-one,
20) (S)-1-(3-((4-((4-acetylpiperazin-1-yl) methyl)-6-(5-methylthiazol-2-yl) amino) pyridin-2-yl) amino) piperidin-1-yl) prop-2-en-1-one,
21) (S)-1-(3-((4-((5-methylthiazol-2-yl) amino)-6-(morpholinomethyl) pyrimidin-2-yl) amino) piperidin-1-yl) prop-2-en-1-one,
22) (S)-1-(3-((4-((4-(2-methoxyethyl) piperazin-1-yl) methyl)-6-(5-methylthiazol-2-yl) amino) pyridin-2-yl) amino) piperidin-1-yl) prop-2-en-1-one,
23) (S)-1-(3-((4-((5-methylthiazol-2-yl) amino)-6-(morpholinomethyl) pyrimidin-2-yl) amino) piperidin-1-yl) but-2-yn-1-one,
24) (S)-1-(3-((4-((5-methylthiazol-2-yl) amino)-6-(morpholinomethyl) pyrimidin-2-yl) amino) pyrrolidin-1-yl) prop-2-en-1-one,
25) (R)-1-(3-((4-((5-methylthiazol-2-yl) amino)-6-(morpholinomethyl) pyrimidin-2-yl) amino) piperidin-1-yl) prop-2-en-1-one,
26) (S)-1-(3-(methyl (6-((5-methylthiazol-2-yl) amino)-4-(morpholinomethyl) pyridin-2-yl) amino) piperidin-1-yl) prop-2-en-1-one,
27) N-(1-(6-((5-methylthiazol-2-yl) amino)-4-(morpholinomethyl) pyridin-2-yl) piperidin-4-yl) acrylamide,
28) 1-(6-(6-((5-methylthiazol-2-yl) amino)-4-(morpholinomethyl) pyridin-2-yl) octahydro-1H-pyrrolo[2,3-c] pyridin-1-yl) prop-2-en-1-one,
29) 1-(6-(6-((5-methylthiazol-2-yl) amino)-4-(morpholinomethyl) pyridin-2-yl) octahydro-1H-pyrrolo[2,3-c] pyridin-1-yl) but-2-yn-1-one,
30) 1-(6-((6-((5-methylthiazol-2-yl) amino)-4-(morpholinomethyl) pyridin-2-yl) amino)-2-azaspiro[3.3] heptan-2-yl) prop-2-en-1-one,
31) (S)-1-(3-((4-((5-methylthiazol-2-yl) amino)-6-(piperidin-1-ylmethyl) pyrimidin-2-yl) amino) piperidin-1-yl) prop-2-en-1-one,
32) (S)-1-(3-((4-((4-ethylpiperazin-1-yl) methyl)-6-(5-methylthiazol-2-yl) amino) pyrimidin-2-yl) amino) piperidin-1-yl) prop-2-en-1-one,
33) (S)-1-(3-((4-((1-methylpiperidin-4-yl) oxy)-6-((5-methylthiazol-2-yl) amino) pyridin-2-yl) amino) piperidin-1-yl) prop-2-en-1-one,
34) (S)-3-(4-((2-((1-acryloylpiperidin-3-yl) amino)-6-((5-methylthiazol-2-yl) amino) pyridin-4-yl) methyl) piperazin-1-yl) propanenitrile,
35) (S)-1-(3-((4-methyl-6-((5-methylthiazol-2-yl) amino) pyridin-2-yl) amino) piperidin-1-yl) prop-2-en-1-one,
36) (S)-1-(3-((6-((5-methylthiazol-2-yl) amino)-4-(pyridin-3-ylmethyl) pyridin-2-yl) amino) piperidin-1-yl) prop-2-en-1-one,
37) (S)-1-(3-((6-((5-methylthiazol-2-yl) amino)-4-(pyridin-2-ylmethyl) pyridin-2-yl) amino) piperidin-1-yl) prop-2-en-1-one,
38) (S)-2-((1-acryloylpiperidin-3-yl) amino)-6-(5-methylthiazol-2-yl) amino) isonicotinonitrile,
39) (S)-1-(3-((6-((5-methylthiazol-2-yl) amino)-4-phenylpyridin-2-yl) amino) piperidin-1-yl) prop-2-en-1-one,
40) (S)-1-(3-((4-((1-methylpiperidin-4-yl) oxy)-6-((5-methylthiazol-2-yl) amino) pyridin-2-yl) amino) piperidin-1-yl) prop-2-yn-1-one,
41) (S)-1-(3-((4-((1-methylpiperidin-4-yl) oxy)-6-((5-methylthiazol-2-yl) amino) pyridin-2-yl) amino) piperidin-1-yl) but-2-yn-1-one,
42) (S)-1-(3-((4-((4-ethylpiperazin-1-yl) methyl)-6-((5-methylthiazol-2-yl) amino) pyridin-2-yl) amino) piperidin-1-yl) prop-2-en-1-one,
43) (S)-1-(3-((4-((4-methylpiperazin-1-yl) methyl)-6-(5-methylthiazol-2-yl) amino) pyridin-2-yl) amino) piperidin-1-yl) prop-2-en-1-one, 44) 5-methyl-N-(6-methyl-4-(morpholinomethyl) pyridin-2-yl) thiazol-2-amine,
45) (S)-3-chloro-1-(3-((6-((5-methylthiazol-2-yl) amino)-4-(morpholinomethyl) pyridin-2-yl) amino) piperidin-1-yl) propan-1-one,
46) (S,E)-3-chloro-1-(3-(6-(5-methylthiazol-2-ylamino)-4-(morpholinomethyl) pyridin-2-ylamino) piperidin-1-yl) prop-2-en-1-one,
47) (S)-1-(3-(4-((4-(3-aminopropyl) piperazin-1-yl) methyl)-6-(5-methylthiazol-2-ylamino) pyridin-2-ylamino) piperidin-1-yl) prop-2-en-1-one,
48) (S)-1-(3-(6-(1H-pyrazol-3-ylamino)-4-(morpholinomethyl) pyridin-2-ylamino) piperidin-1-yl) prop-2-en-1-one,
49) (S)-1-(3-(4-(morpholinomethyl)-6-(5-(trifluoromethyl) thiazol-2-ylamino) pyridin-2-ylamino) piperidin-1-yl) prop-2-en-1-one,
50) (S)-1-(3-(6-(5-chloro-1H-pyrazol-3-ylamino)-4-(morpholinomethyl) pyridin-2-ylamino) piperidin-1-yl) prop-2-en-1-one,
51) (S)-1-(3-(4-(morpholinomethyl)-6-(thiazol-2-ylamino) pyridin-2-ylamino) piperidin-1-yl) prop-2-en-1-one,
52) (S)-1-(3-(3-fluoro-6-(5-methylthiazol-2-ylamino)-4-(morpholinomethyl) pyridin-2-ylamino) piperidin-1-yl) prop-2-en-1-one,
53) (S)-1-(3-(4-(morpholinomethyl)-6-(pyridin-2-ylamino) pyridin-2-ylamino) piperidin-1-yl) prop-2-en-1-one, and
54) (S)-1-(3-(4-(morpholinomethyl)-6-(pyrimidin-2-ylamino) pyridin-2-ylamino) piperidin-1-yl) prop-2-en-1-one.

In addition, according to the present disclosure, when A is not $C_{1-4}$ alkyl, the compound represented by Chemical Formula 1 may be prepared, for example, through Reaction Formula 1 below.

[Reaction Scheme 1]

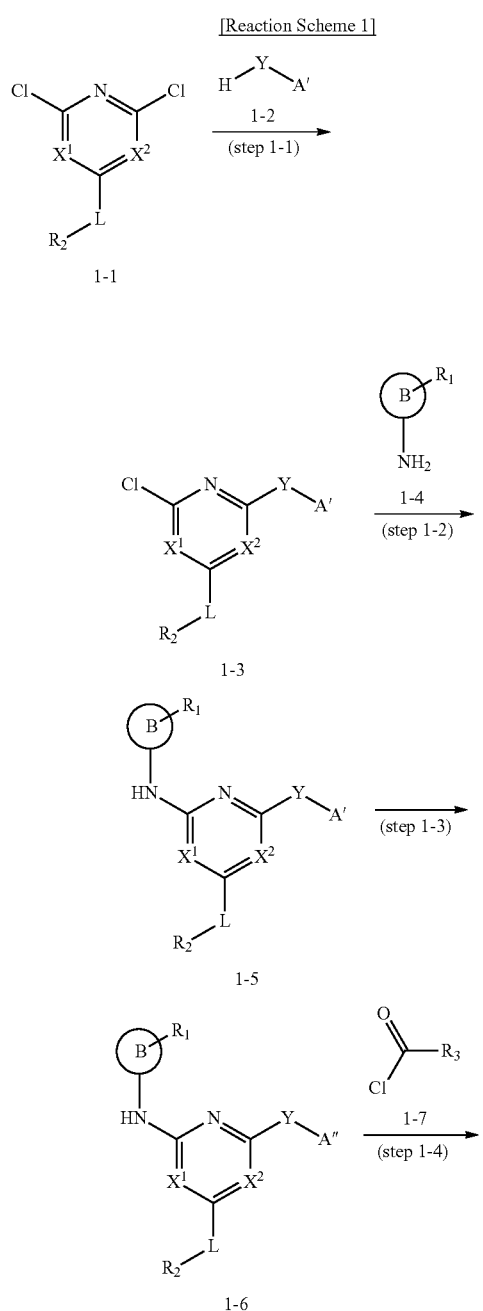

In Reaction Scheme 1, A' is

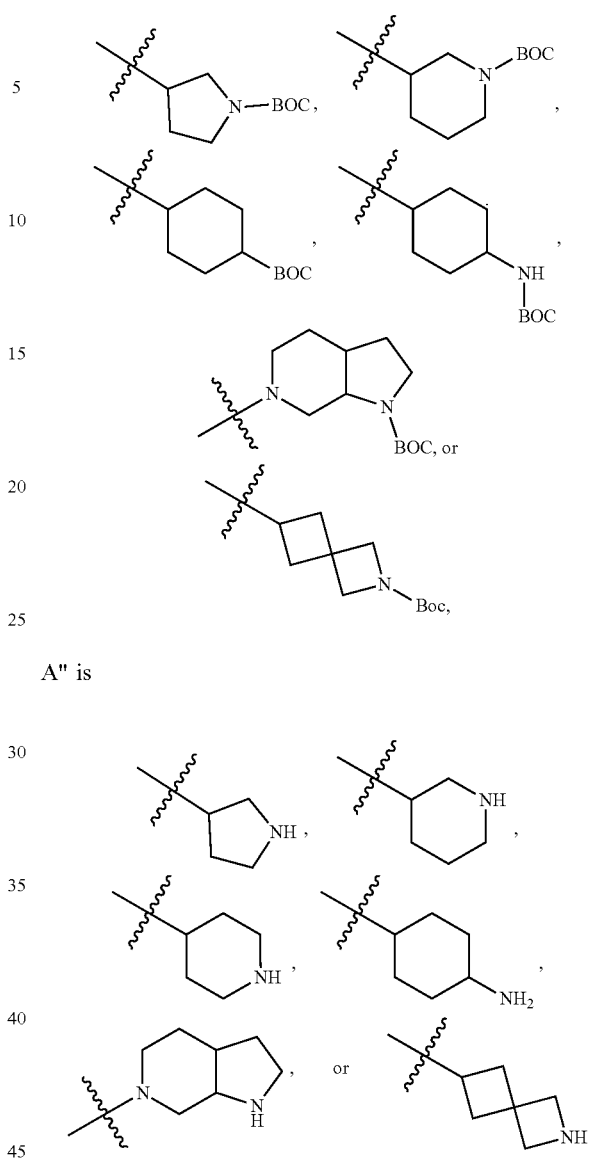

A" is

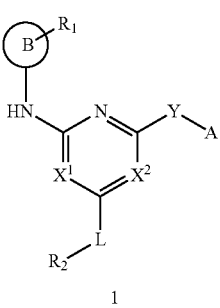

and the rest are as defined above.

Step 1-1 is a step of reacting the compound represented by Chemical Formula 1-1 and the compound represented by Chemical Formula 1-2 to prepare the compound represented by Chemical Formula 1-3. When the reaction is an amine substitution reaction, the reaction is preferably carried out in the presence of a palladium catalyst and a base, and when the reaction is a solvolysis reaction of an alkyl chloride due to a secondary alcohol, the reaction is preferably carried out in the presence of a base.

Step 1-2 is a step of reacting the compound represented by Chemical Formula 1-3 and the compound represented by Chemical Formula 1-4 to prepare the compound represented by Chemical Formula 1-5. The reaction is an amine substitution reaction, which is preferably carried out in the presence of a palladium catalyst and a base.

Step 1-3 is a step of removing a protecting group (BOC; tert-butyloxycarbonyl protecting group) from the compound represented by Chemical Formula 1-5 to prepare the compound represented by Chemical Formula 1-6. The reaction is preferably carried out under acidic conditions capable of removing the protecting group.

Step 1-4 is a step of reacting the compound represented by Chemical Formula 1-6 with the compound represented by Chemical Formula 1-7 to prepare the compound represented by Chemical Formula 1. The reaction is an amidation reaction, which is preferably carried out in the presence of a base.

Further, in Reaction Scheme 1, a reaction for protecting with a protecting group and a reaction for removing the protecting group may be added depending on each substituent.

According to another embodiment of the present disclosure, in the compound represented by Chemical Formula 1, when L is methylene and A is not $C_{1-4}$ alkyl, the compound represented by Chemical Formula 1 may be prepared, for example, through Reaction Scheme 2 below.

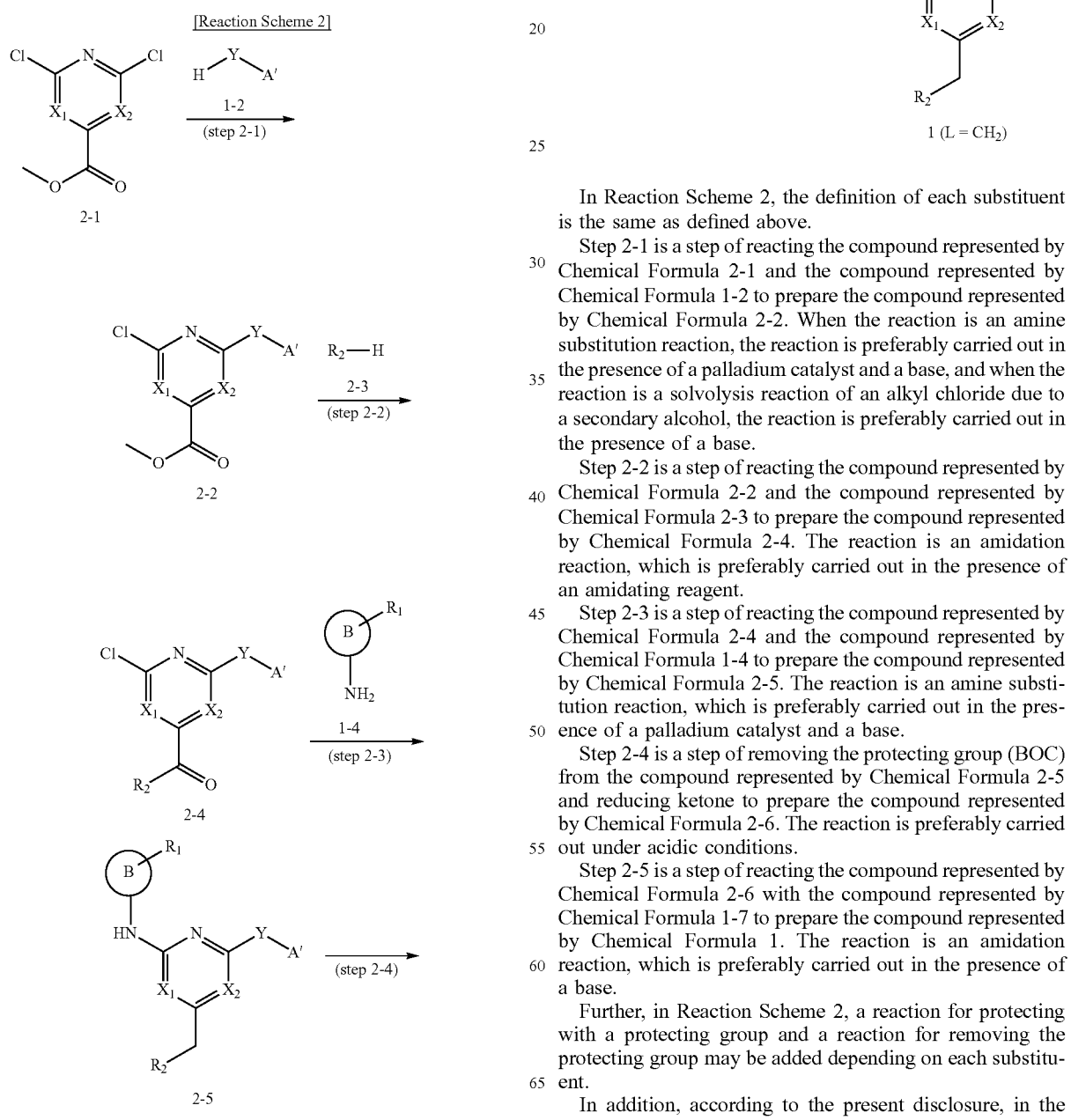

In Reaction Scheme 2, the definition of each substituent is the same as defined above.

Step 2-1 is a step of reacting the compound represented by Chemical Formula 2-1 and the compound represented by Chemical Formula 1-2 to prepare the compound represented by Chemical Formula 2-2. When the reaction is an amine substitution reaction, the reaction is preferably carried out in the presence of a palladium catalyst and a base, and when the reaction is a solvolysis reaction of an alkyl chloride due to a secondary alcohol, the reaction is preferably carried out in the presence of a base.

Step 2-2 is a step of reacting the compound represented by Chemical Formula 2-2 and the compound represented by Chemical Formula 2-3 to prepare the compound represented by Chemical Formula 2-4. The reaction is an amidation reaction, which is preferably carried out in the presence of an amidating reagent.

Step 2-3 is a step of reacting the compound represented by Chemical Formula 2-4 and the compound represented by Chemical Formula 1-4 to prepare the compound represented by Chemical Formula 2-5. The reaction is an amine substitution reaction, which is preferably carried out in the presence of a palladium catalyst and a base.

Step 2-4 is a step of removing the protecting group (BOC) from the compound represented by Chemical Formula 2-5 and reducing ketone to prepare the compound represented by Chemical Formula 2-6. The reaction is preferably carried out under acidic conditions.

Step 2-5 is a step of reacting the compound represented by Chemical Formula 2-6 with the compound represented by Chemical Formula 1-7 to prepare the compound represented by Chemical Formula 1. The reaction is an amidation reaction, which is preferably carried out in the presence of a base.

Further, in Reaction Scheme 2, a reaction for protecting with a protecting group and a reaction for removing the protecting group may be added depending on each substituent.

In addition, according to the present disclosure, in the compound represented by Chemical Formula 1, the compound in which A is $C_{1-4}$ alkyl can be prepared using the same method as in step 1-1 and step 1-2 of Reaction Scheme 1, except that in step 1-1 of Reaction Scheme 1, the compound represented by

is used instead of the compound represented by Chemical Formula 1-2.

The production method of each step described above can be more embodied in Examples described hereinafter.

According to a further embodiment of the present disclosure, there is provided a pharmaceutical composition for preventing or treating autoimmune diseases or cancer diseases, which is effective for ITK and BTK inhibitory actions, comprising the compound represented by Chemical Formula 1, or a pharmaceutically acceptable salt, hydrate, solvate or isomer thereof as an active ingredient.

In this case, the autoimmune diseases include rheumatoid arthritis, systemic lupus erythematosus, childhood diabetes, psoriasis, aphthous stomatitis, chronic thyroiditis, acquired aplastic anemia, primary cirrhosis, ulcerative colitis, Behcet's disease, Crohn's disease, Silicosis, asbestosis, Sjogren's syndrome, Guillain-Barre syndrome, dermatomyositis, polymyositis, multiple sclerosis, autoimmune hemolytic anemia, autoimmune encephalomyelitis, myasthenia gravis, Graves thyroid hyperplasia, nodular polyarteritis, ankylosing spondylitis, fibrositis, temporal arteritis, Wilson's disease, or Fanconi syndrome, and the cancer may be blood cancer, extranodal marginal zone B-cell lymphoma, glioblastoma, lymphoplasmacytic lymphoma, acute myelogenous leukemia, macroglobulinemia, B cell lymphoma, chronic lymphocytic leukemia, follicular lymphoma, non-hodgkin lymphoma, diffuse large B cell lymphoma, hairy cell leukemia, mantle cell lymphoma, glioblastoma, bladder cancer, pancreatic cancer, ovarian cancer, colorectal cancer, renal cancer, gastric cancer, transitional cell carcinoma, carcinoid tumor, breast cancer, non-small cell lung cancer, or multiple myeloma.

As used herein, the term "prevention" refers to any act to delay or inhibit occurrence, spread or recurrence of the above-mentioned diseases by administration of the composition of the present disclosure, and "treatment" refers to any act to improve or change the symptoms of the above diseases for the better by administration of the composition of the present disclosure.

The pharmaceutical composition according to the present disclosure can be formulated in types for oral or parenteral administrations according to a standard pharmaceutical practice. These formulations may contain additives such as pharmaceutically acceptable carrier, adjuvant or diluent in addition to the active ingredient.

Suitable carriers include, for example, physiological saline, polyethylene glycol, ethanol, vegetable oil, and isopropyl myristate and the like. Diluents include, for example, lactose, dextrose, sucrose, mannitol, sorbitol, cellulose and/or glycine and the like. but are not limited thereto. Further, the compounds of the present disclosure can be dissolved in oils, propylene glycol or other solvents commonly used in the preparation of injection solutions. Furthermore, the compounds of the present disclosure can be formulated in ointments or creams for topical application.

A preferred dose of the compound of the present disclosure may be varied according to the condition and weight of a patient, the severity of a disease, the type of a drug, and the route and duration of administration, but it may be suitably selected by those skilled in the art. In order to achieve the desirable effects, however, the compound of the present disclosure may be administrated daily at a dose of 0.0001 to 100 mg/kg (body weight), and preferably 0.001 to 100 mg/kg (body weight). The administration may be performed once a day or in divided doses each day through an oral or parenteral route.

Depending on the method of administration, the pharmaceutical composition may contain the compound of the present disclosure in an amount of 0.001 to 99% by weight, preferably 0.01 to 60% by weight.

The pharmaceutical composition according to the present disclosure may be administered to mammals such as a rat, a mouse, a domestic animal, a human, through various routes. The administration may be carried out through all possible methods, for example, oral, rectal, intravenous, intramuscular, subcutaneous, intra-endometrial, intracerebroventricular injection.

Advantageous Effects

The compound represented by Chemical Formula 1 according to the present disclosure or a pharmaceutically acceptable salt, hydrate, solvate or isomer thereof can be usefully used for the prevention or treatment of autoimmune diseases or cancers.

DETAILED DESCRIPTION OF THE EMBODIMENTS

Below, the present disclosure will be described in more detail by way of examples. However, these examples are provided for illustrative purposes only, and should not be construed as limiting the scope of the present disclosure to these examples.

Example 1: Preparation of 1-(3-((6-((5-methylthiazol-2-yl) amino)-4-(morpholinomethyl) pyridin-2-yl) amino) piperidin-1-yl) prop-2-en-1-one Step 1-1: Preparation of (2,6-dichloropyridin-4-yl) (morpholino) methanone

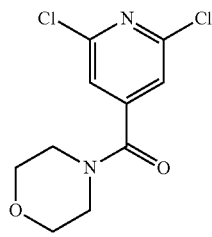 [SMILES: O=C(c1cc(Cl)nc(Cl)c1)N1CCOCC1]

2,6-Dichloroisonicotinic acid (10.0 g, 1.0 eq) was dissolved in dimethylformamide (100.0 mL), and then 1,1-carbonyldiimidazole (1.0 g, 1.2 eq) was added thereto. The mixture was stirred at room temperature (25~30° C.) for 1 hour under nitrogen gas, and then morpholine (5.4 mL, 1.2 eq) was added and stirred at the same temperature for 2 hours to complete the reaction. Ethyl acetate (200.0 mL) and water (200.0 mL) were added thereto, followed by extraction, and the aqueous layer was re-extracted three times using ethyl acetate (200.0 mL). The ethyl acetate layer was dried over anhydrous sodium sulfate and then concentrated under reduced pressure. The resulting residue was purified by column chromatography (ethyl acetate:hexane=1:5) to give the title compound (13.0 g, yield: 93.0%).

Step 1-2: Preparation of 4-((2,6-dichloropyridin-4-yl) methyl) morpholine

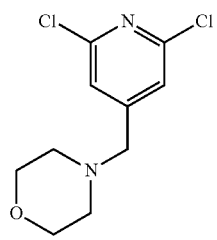 [SMILES: Clc1cc(CN2CCOCC2)cc(Cl)n1]

The intermediate (10.0 g, 1.0 eq) obtained in step 1-1 was dissolved in dichloromethane (100.0 mL), and then cooled to 0 to 10° C. under nitrogen gas. 1M borane-tetrahydrofuran (115.0 mL, 3.0 eq) was slowly added dropwise. The mixture was stirred at room temperature for 12 hours to complete the reaction. The reaction solution was cooled to 0 to 10° C. and then 6N-hydrochloric acid aqueous solution (256.0 mL, 20.0 eq) was slowly added dropwise, and then stirred at the same temperature for 1 hour. After adjusting the pH to 9~12 using 10N-sodium hydroxide aqueous solution, extraction was performed twice with dichloromethane. The dichloromethane layer was separated, dried over anhydrous sodium sulfate, and then concentrated under reduced pressure. The resulting residue was purified by column chromatography (ethyl acetate:hexane=1:1) to give the title compound (8.1 g, yield: 90.0%).

Step 1-3: Preparation of tert-butyl 3-((6-chloro-4-(morpholinomethyl) pyridin-2-yl) amino) piperidine-1-carboxylate

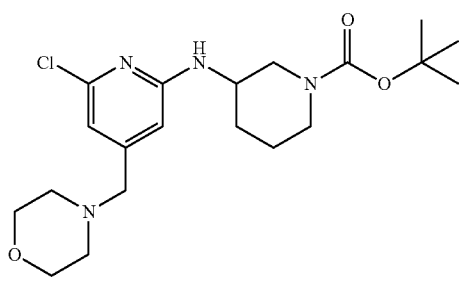 [SMILES: CC(C)(C)OC(=O)N1CCCC(Nc2cc(CN3CCOCC3)cc(Cl)n2)C1]

After 1,4-dioxane (10.0 mL) was added to the intermediate (1.0 g, 1.0 eq) obtained in step 1-2 and dissolved, tris(dibenzylideneacetone) dipalladium (0) (465.8 mg, 0.2 eq) and Xantphos (1.5 g, 0.4 eq) were added thereto. Tert-butyl 3-aminopiperidine-1-carboxylate (780.0 μl, 1.0 eq) was added, and then sodium carbonate (1.3 g, 3.0 eq) was added, and the mixture was refluxed for 12 hours to complete the reaction. After cooling to 30° C. or less, water (20.0 mL) and ethyl acetate (20.0 mL) were added, and then the layers were separated. The ethyl acetate layer was dried over anhydrous sodium sulfate and then concentrated under reduced pressure. The resulting residue was purified by column chromatography (ethyl acetate:hexane=1:1) to give the title compound (900.0 mg, yield: 54.1%).

Step 1-4: Preparation of tert-butyl 3-((6-((5-methylthiazol-2-yl) amino)-4-(morpholinomethyl) pyridin-2-yl) amino) piperidine-1-carboxylate

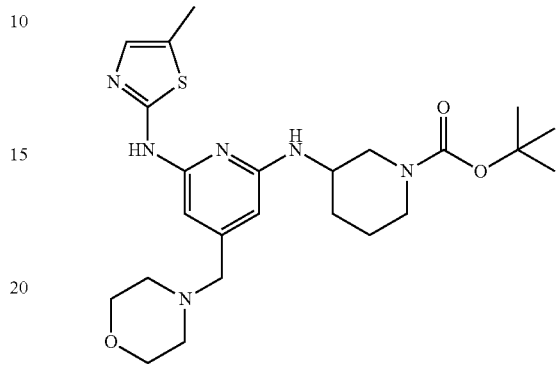

The intermediate (730.0 mg, 1.0 eq) obtained in step 1-3 was dissolved in 1,4-dioxane (14.0 mL). Palladium acetate (40.0 mg, 0.1 eq), Xantphos (204.7 mg, 0.2 eq), 5-methylthio-2-amine (203.6 mg, 1.0 eq), and cesium carbonate (1.7 g, 3.0 eq) were sequentially added. The mixture was reacted in a microwave reactor at 150° C. for 30 minutes. Ethyl acetate (10.0 mL) and water (10.0 mL) were added, and the resulting solid was filtered to give the title compound (424.9 mg, yield 65.4%). After cooling to 30° C. or less, water (15.0 mL) and ethyl acetate (15.0 mL) were added thereto, followed by layer separation. The ethyl acetate layer was dried over anhydrous sodium sulfate and then concentrated under reduced pressure. The resulting residue was purified by column chromatography (EA 100%) to give the title compound (564.0 mg, yield: 65.0%).

Step 1-5: Preparation of $N^2$-(5-methylthiazol-2-yl)-4-(morpholinomethyl)-$N^6$-(piperidin-3-yl) pyridin-2,6-diamine

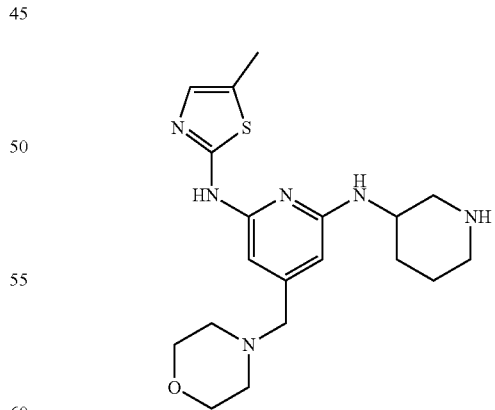

The intermediate (500.0 mg, 1.0 eq) obtained in step 1-4 was dissolved in dichloromethane (10.0 mL), and then cooled to 0 to 10° C. Trifluoroacetic acid (1.6 mL, 20.0 eq) was slowly added dropwise, and then stirred for 1 hour. After adjusting the pH to 9-12 using 12N-sodium hydroxide aqueous solution, the separated dichloromethane layer was dried over anhydrous sodium sulfate and then concentrated under reduced pressure. Ethyl acetate (10.0 mL) was added to the resulting residue to form crystals for 30 minutes. The crystals were filtered and dried to give the title compound (357.5 mg, yield: 90.0%).

Step 1-6: Preparation of 1-(3-((6-((5-methylthiazol-2-yl) amino)-4-(morpholinomethyl) pyridin-2-yl) amino) piperidin-1-yl) prop-2-en-1-one

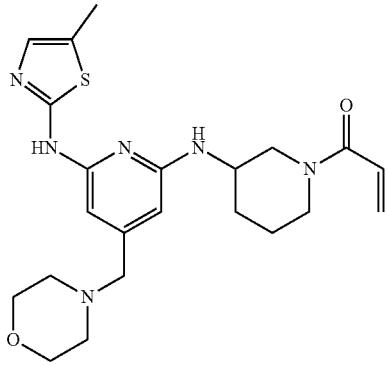 [SMILES: C=CC(=O)N1CCCC(Nc2cc(CN3CCOCC3)cc(Nc3ncc(C)s3)n2)C1]

After the intermediate (350.0 mg, 1.0 eq) obtained in step 1-5 was dissolved in tetrahydrofuran (7.0 mL), water (7.0 mL) was added and sodium bicarbonate (226.8 mg, 3.0 eq) was added, and then cooled to 0 to 10° C. Acryloyl chloride (73.1 μl, 1.0 eq) was slowly added dropwise, and then stirred for 30 minutes to complete the reaction. The layers were separated with dichloromethane, dried over anhydrous sodium sulfate and concentrated under reduced pressure. The resulting residue was purified by column chromatography (dichloromethane:methanol=15:1) to give the title compound (318.0 mg, yield: 80.0%).

1H NMR (500 MHZ, DMSO): 10.5 (s, 1H), 6.94 (s, 1H), 6.86-6.80 (q, 1H), 6.50-6.49 (d, 1H), 6.10-6.07 (d, 1H), 6.04 (s, 1H), 5.94 (s, 1H), 5.66-5.64 (d, 1H), 4.38-4.36 (m, 1H), 4.18-4.16 (m, 1H), 4.08-4.06 (m, 1H), 3.55 (m, 4H), 3.21 (s, 3H), 2.88-2.83 (m, 2H), 2.32 (m, 4H), 2.28 (s, 3H), 2.03 (m, 2H), 1.30 (m, 2H)

Example 2: Preparation of 1-(3-((6-((5-methylthiazol-2-yl) amino)-4-(morpholinomethyl) pyridin-2-yl) amino) pyrrolidin-1-yl) prop-2-en-1-one

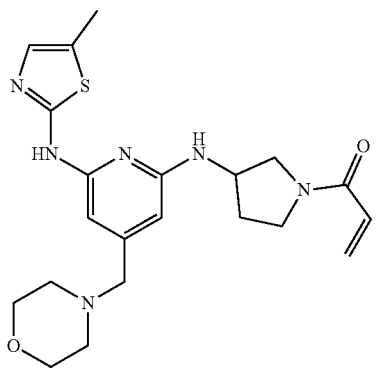 [SMILES: C=CC(=O)N1CCC(Nc2cc(CN3CCOCC3)cc(Nc3ncc(C)s3)n2)C1]

The title compound (15.0 mg, yield: 23.0%) was obtained in the same manner as in Example 1, except that in steps 1-3 of Example 1, tert-butyl 3-aminopyrrolidine-1-carboxylate was used instead of tert-butyl 3-aminopiperidine-1-carboxylate.

1H NMR (500 MHZ, DMSO): 10.58-10.57 (m, 1H), 6.94 (s, 1H), 6.83-6.75 (m, 1H), 6.63-6.48 (m, 1H), 6.14-6.10 (m, 1H), 6.08 (s, 1H), 5.99-5.98 (m, 1H), 5.67-5.59 (m, 1H), 4.65-4.50 (m, 1H), 3.99-3.97 (m, 0.5H), 3.70-3.66 (m, 1.5H), 3.55 (m, 4H), 3.48 (m, 1H), 3.35 (m, 1H), 3.22 (s, 2H), 2.34-2.32 (m, 4H), 2.26-2.24 (d, 3H), 2.25 (m, 1H), 1.95-1.85 (m, 1H)

Example 3: Preparation of 1-(4-((6-((5-methylthiazol-2-yl) amino)-4-(morpholinomethyl) pyridin-2-yl) amino) piperidin-1-yl) prop-2-en-1-one

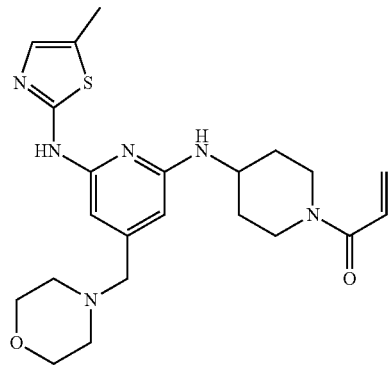 [SMILES: C=CC(=O)N1CCC(Nc2cc(CN3CCOCC3)cc(Nc3ncc(C)s3)n2)CC1]

The title compound (8.0 mg, yield: 53.0%) was obtained in the same manner as in Example 1, except that in step 1-3 of Example 1, tert-butyl 4-aminopiperidine-1-carboxylate was used instead of tert-butyl 3-aminopiperidine-1-carboxylate.

1H NMR (500 MHZ, DMSO): 10.54 (s, 1H), 6.94 (s, 1H), 6.93-6.83 (m, 1H), 6.51-6.49 (d, 1H), 6.10 (d, 1H), 6.07 (s, 1H), 5.94 (s, 1H), 5.66-5.64 (d, 1H), 4.38-4.36 (m, 1H), 4.16 (m, 1H), 4.08-4.02 (m, 1H), 3.56 (m, 4H), 3.21 (s, 2H), 2.85 (m, 1H), 2.61 (m, 1H), 2.34-2.33 (m, 4H), 2.28 (s, 3H), 2.0 (m, 2H), 1.30-1.21 (m, 2H)

Example 4: Preparation of (R)-1-(3-((6-((5-methylthiazol-2-yl) amino)-4-(morpholinomethyl) pyridin-2-yl) amino) piperidin-1-yl) prop-2-en-1-one

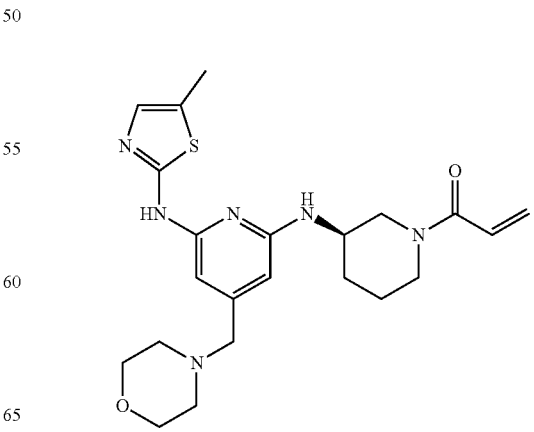

The title compound (10.0 mg, yield: 53.0%) was obtained in the same manner as in Example 1, except that in steps 1-3 of Example 1, tert-butyl (R)-3-aminopiperidine-1-carboxylate was used instead of tert-butyl 3-aminopiperidine-1-carboxylate.

1H NMR (500 MHZ, DMSO): 10.55-10.50 (m, 1H), 6.91-6.90 (m, 1H), 6.90-6.78 (m, 0.5H), 6.47-6.56 (m, 1.5H), 6.06-5.96 (m, 3H), 5.65-5.67 (m, 0.5H), 5.42-5.40 (m, 0.5H), 4.42-4.40 (m, 0.5H), 4.10-4.0 (m, 1H), 3.90-3.87 (m, 1.5H), 3.56 (m, 4H), 3.20 (s, 2H), 3.14-3.10 (m, 1H), 2.68-2.63 (m, 0.5H), 2.32 (m, 4H), 2.19 (s, 3H), 1.90-2.0 (m, 1H), 1.80 (m, 1H), 1.50-1.40 (m, 2.5H)

Example 5: Preparation of(S)-1-(3-((6-((5-methylthiazol-2-yl) amino)-4-(morpholinomethyl) pyridin-2-yl) amino) piperidin-1-yl) prop-2-en-1-one

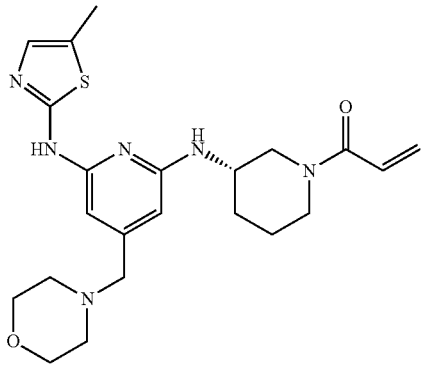 [SMILES: C=CC(=O)N1CCC[C@H](Nc2cc(CN3CCOCC3)cc(Nc3ncc(C)s3)n2)C1]

The title compound (13.0 mg, yield: 63.0%) was obtained in the same manner as in Example 1, except that in steps 1-3 of Example 1, tert-butyl(S)-3-aminopiperidine-1-carboxylate was used instead of tert-butyl 3-aminopiperidine-1-carboxylate.

1H NMR (500 MHZ, DMSO): 10.57 (m, 1H), 6.91-6.90 (m, 1H), 6.80-6.85 (m, 0.5H), 6.70-6.40 (m, 1.5H), 6.10-5.96 (m, 3H), 5.65-5.63 (d, 0.5H), 5.42-5.40 (d, 0.5H), 4.42-4.40 (m, 0.5H), 4.10-4.0 (m, 1H), 3.90-3.87 (m, 1.5H), 3.56 (m, 4H), 3.20 (s, 2H), 3.14-3.10 (m, 1H), 2.68-2.63 (m, 0.5H), 2.32 (m, 4H), 2.19 (s, 3H), 1.90-2.0 (m, 1H), 1.80 (m, 1H), 1.50-1.40 (m, 2.5H)

Example 6: Preparation of (R)-1-(3-((6-((5-methylthiazol-2-yl) amino)-4-(morpholinomethyl) pyridin-2-yl) amino) pyrrolidin-1-yl) prop-2-en-1-one

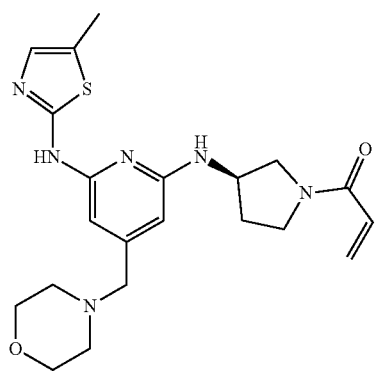 [SMILES: C=CC(=O)N1CC[C@@H](Nc2cc(CN3CCOCC3)cc(Nc3ncc(C)s3)n2)C1]

The title compound (10.0 mg, yield: 58.0%) was obtained in the same manner as in Example 1, except that in step 1-3 of Example 1, tert-butyl (R) 3-aminopyrrolidine-1-carboxylate was used instead of tert-butyl 3-aminopiperidine-1-carboxylate.

1H NMR (500 MHZ, DMSO): 10.7 (m, 1H), 6.94 (s, 1H), 6.83-6.75 (m, 1H), 6.63-6.47 (m, 1H), 6.14-6.10 (m, 2H), 6.09-3.08 (m, 1H), 5.67-5.59 (m, 1H), 4.67-4.50 (1H), 3.97-3.96 (m, 0.5H), 3.70 (m, 1.5H), 3.55-3.54 (m, 4H), 3.40 (m, 1H), 3.38 (m, 1H), 3.22 (s, 2H), 2.32 (m, 4H), 2.26-2.24 (d, 3H), 2.20 (m, 1H), 1.95-1.80 (m, 1H)

Example 7: Preparation of(S)-1-(3-((6-((5-methylthiazol-2-yl) amino)-4-(morpholinomethyl) pyridin-2-yl) amino) pyrrolidin-1-yl) prop-2-en-1-one

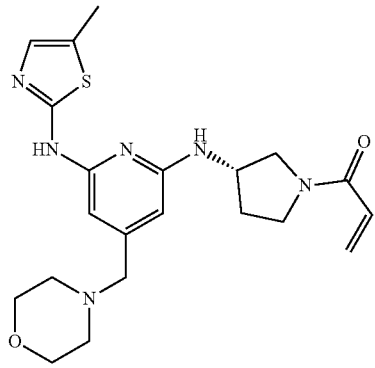 [SMILES: C=CC(=O)N1CC[C@H](Nc2cc(CN3CCOCC3)cc(Nc3ncc(C)s3)n2)C1]

The title compound (15.0 mg, yield: 63.0%) was obtained in the same manner as in Example 1, except that in step 1-3 of Example 1, tert-butyl(S) 3-aminopyrrolidine-1-carboxylate was used instead of tert-butyl 3-aminopiperidine-1-carboxylate.

1H NMR (500 MHZ, DMSO): 10.7 (m, 1H), 6.94 (s, 1H), 6.83-6.75 (m, 1H), 6.63-6.47 (m, 1H), 6.14-6.10 (m, 2H), 6.09-3.08 (m, 1H), 5.67-5.59 (m, 1H), 4.67-4.50 (1H), 3.97-3.96 (m, 0.5H), 3.70 (m, 1.5H), 3.55-3.54 (m, 4H), 3.40 (m, 1H), 3.38 (m, 1H), 3.22 (s, 2H), 2.32 (m, 4H), 2.26-2.24 (d, 3H), 2.20 (m, 1H), 1.95-1.80 (m, 1H)

Example 8: Preparation of 1-(3-((2-((5-methylthiazol-2-yl) amino)-6-(morpholinomethyl) pyrimidin-4-yl) amino) pyrrolidin-1-yl) prop-2-en-1-one Step 8-1: Preparation of methyl 6-((1-(tert-butoxycarbonyl) pyrrolidin-3-yl) amino)-2-chloropyrimidine-4-carboxylate

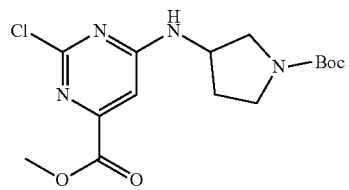 [SMILES: COC(=O)c1cc(NC2CCN(C(=O)OC(C)(C)C)C2)nc(Cl)n1]

After methyl 2,4-dichloropyrimidine-6-carboxylate (500 mg, 1.0 eq) was dissolved in tetrahydrofuran (10.0 mL), diisopropylethylamine (1.5 eq) and tert-butyl 3-aminopyrrolidine-1-carboxylate (1.5 eq) were added thereto and then stirred at 80° C. for 1 hour. Upon completion of the reaction, the mixture was cooled to 30° C. or less, water (100.0 mL) and dichloromethane (100.0 mL) were added thereto, followed by extraction. The separated organic layer was dried over anhydrous sodium sulfate and then concentrated under reduced pressure. The resulting residue was purified by column chromatography (ethyl acetate:hexane=1:1) to give the title compound (640.0 mg, yield: 74.0%).

Step 8-2: Preparation of tert-butyl 3-((2-chloro-6-(morpholin-4-carbonyl) pyrimidin-4-yl) amino) pyrrolidine-1-carboxylate

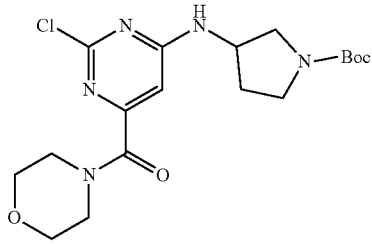 [SMILES: CC(C)(C)OC(=O)N1CCC(Nc2cc(C(=O)N3CCOCC3)nc(Cl)n2)C1]

After methyl 6-((1-tert-butoxycarbonyl) pyrrolidin-3-yl) amino)-2-chloropyrimidine-4-carboxylate (640.0 mg, 1.0 eq) obtained in step 8-1 was dissolved in tetrahydrofuran (10.0 mL), 1,5,7-triazabicyclo[4,4,0] dec-5-ene (0.3 eq) and morpholine (1.2 eq) were added thereto, and stirred at 60° C. for 3 hours. Upon completion of the reaction, water (200.0 mL) and dichloromethane (200.0 mL) were added thereto, followed by extraction. The separated organic layer was dried over sodium hydroxide and then concentrated under reduced pressure. The resulting residue was purified by column chromatography (ethyl acetate:methanol=9:1) to give the title compound (470.0 mg, yield: 63.7%).

Step 8-3: Preparation of tert-butyl 3-((2-((5-methylthiazol-2-yl) amino)-6-(morpholine-4-carbonyl) pyrimidin-4-yl) amino) pyrrolidine-1-carboxylate

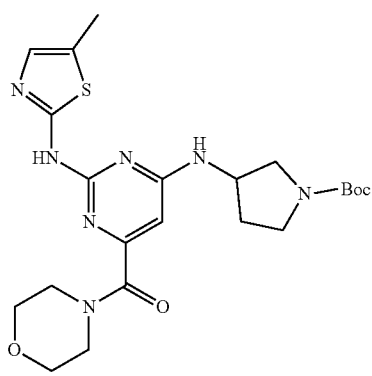 [SMILES: Cc1cnc(Nc2nc(NC3CCN(C(=O)OC(C)(C)C)C3)cc(C(=O)N3CCOCC3)n2)s1]

After tert-butyl 3-((2-chloro-6-(morpholin-4-carbonyl) pyrimidin-4-yl) amino) pyrrolidine-1-carboxylate (450.0 mg, 1.0 eq) obtained in step 8-2 was dissolved in 1,4-dioxane (10.0 mL), palladium acetate (0.1 eq), 4,5-bis(diphenylphosphino)-9,9-dimethylxanthene (0.2 eq), cesium carbonate (3.0 eq), 2-amino-5-methylthiazole (1.2 eq) were added thereto, and reacted in a microwave reactor (160° C., 30 min). Upon completion of the reaction, water (200.0 mL) and ethyl acetate (200.0 mL) were added thereto, followed by extraction. The separated organic layer was dried over anhydrous sodium sulfate and then concentrated under reduced pressure. The resulting residue was purified by column chromatography (ethyl acetate:methanol=9:1) to give the title compound (410.0 mg, yield: 76.6%).

Step 8-4: Preparation of $N^2$-(5-methylthiazol-2-yl)-6-(morpholinomethyl)-$N^4$-(pyrrolidin-3-yl) pyrimidine-2,4-diamine

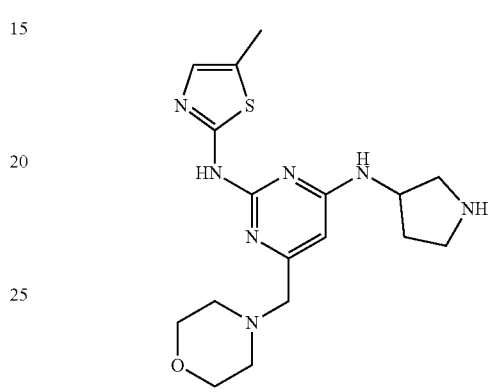

After tert-butyl 3-((2-((5-methylthiazol-2-yl) amino)-6-(morpholin-4-carbonyl) pyrimidin-4-yl) amino) pyrrolidine-1-carboxylate (250.0 mg, 1.0 eq) obtained in step 8-3 was dissolved in tetrahydrofuran (10.0 mL), 0.9M borane-tetrahydrofuran solution (5.0 eq) was added thereto, and stirred at 50° C. for 5 hours. The reaction solution was cooled to 0° C., and then 6N aqueous hydrochloric acid solution (5.0 eq) was added and then stirred at 50° C. for 12 hours. The reaction solution was again cooled to 0° C., and then the pH was adjusted to 12 using 12N sodium hydroxide aqueous solution, and then extracted with dichloromethane (200.0 mL) and water (200.0 mL). The separated organic layer was dried over anhydrous sodium sulfate and then concentrated under reduced pressure to give the title compound (40.0 mg, yield: 20.9%).

Step 8-5: Preparation of 1-(3-((2-((5-methylthiazol-2-yl) amino)-6-(morpholinomethyl) pyrimidin-4-yl) amino) pyrrolidin-1-yl) prop-2-en-1-one

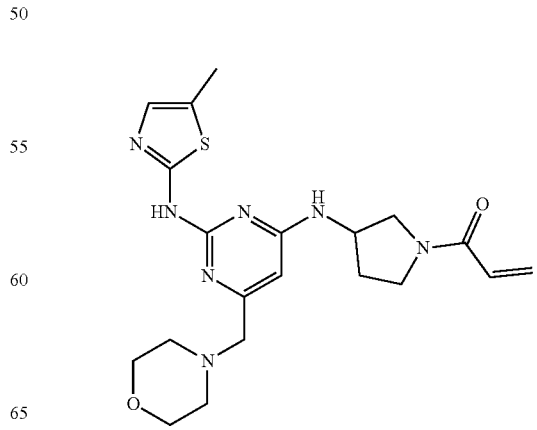

After N²-(5-methylthiazol-2-yl)-6-(morpholinomethyl)-N⁴-(pyrrolidin-3-yl) pyrimidine-2,4-diamine (50.0 mg, 1.0 eq) obtained in step 8-4 was dissolved in tetrahydrofuran (1.6 mL) and water (0.4 mL), sodium bicarbonate (3.0 eq) and acryloyl chloride (1.1 eq) were added thereto, and stirred at 0° C. for 30 minutes. Upon completion of the reaction, water (50.0 mL) and ethyl acetate (50.0 mL) were added thereto, followed by extraction. The separated organic layer was dried over anhydrous sodium sulfate and then concentrated under reduced pressure. The resulting residue was purified by column chromatography (ethyl acetate:methanol=3:1) to give the title compound (7.0 mg, yield: 12.2%).

1H NMR (500 MHZ, CDCl₃): 6.95 (s, 1H), 6.40-6.46 (m, 3H), 6.18 (s, 1H), 5.69-5.74 (m, 1H), 3.91-4.10 (m, 1H), 3.76 (s, 2H), 3.50-3.75 (m, 8H), 2.46-2.56 (m, 6H), 2.36 (s, 3H)

Example 9: Preparation of (E)-1-(3-((2-((5-methylthiazol-2-yl) amino)-6-(morpholinomethyl) pyrimidin-4-yl) amino) pyrrolidin-1-yl) but-2-en-1-one

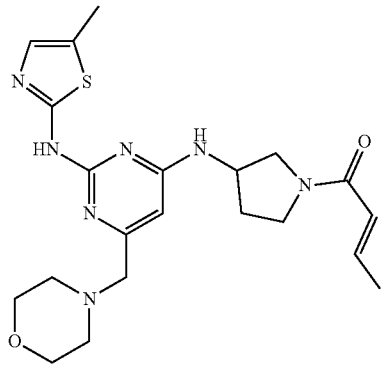 [SMILES: C/C=C/C(=O)N1CCC(Nc2cc(CN3CCOCC3)nc(Nc3ncc(C)s3)n2)C1]

The title compound (5.0 mg, yield: 8.5%) was obtained in the same manner as in Example 8, except that in step 8-5 of Example 8, crotonyl chloride was used instead of acryloyl chloride.

1H NMR (500 MHZ, CDCl₃): 6.94-7.00 (m, 3H), 6.18 (s, 1H), 6.13-6.16 (m, 2H), 4.3 (s, 1H), 3.75 (s, 2H), 3.61-3.73 (m, 8H), 2.56 (s, 4H), 2.29-2.36 (m, 5H), 1.86-1.91 (m, 3H)

Example 10: Preparation of 1-(3-((6-((5-methylthiazol-2-yl) amino)-4-(morpholinomethyl) pyridin-2-yl) oxy) pyrrolidin-1-yl) prop-2-en-1-one Step 10-1: Preparation of tert-butyl 3-((6-chloro-4-(morpholinomethyl) pyridin-2-yl) oxy) pyrrolidine-1-carboxylate

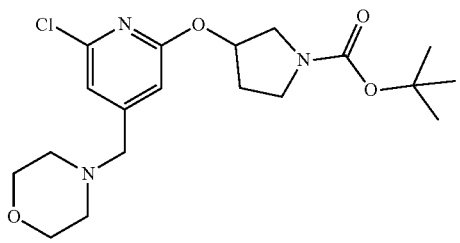 [SMILES: CC(C)(C)OC(=O)N1CCC(Oc2cc(CN3CCOCC3)cc(Cl)n2)C1]

After tert-butyl 3-hydroxypyrrolidine-1-carboxylate (2.0 g. 1.0 eq) was dissolved in dimethylformamide (10.0 ml), potassium t-butoxide (1.4 g. 1.5 eq) was added thereto and stirred for 30 minutes. The intermediate (2.0 g, 1.0 eq) obtained in step 1-2 of Example 1 was added, and then the mixture was stirred at 60 to 80° C. for 4 hours. After cooling to 30° C. or less, water (40.0 mL) and ethyl acetate (40.0 mL) were added, and then the layers were separated. The ethyl acetate layer was dried over anhydrous sodium sulfate and then concentrated under reduced pressure. The resulting residue was purified by column chromatography (ethyl acetate:hexane=1:5) to give the title compound (1.8 g, yield: 55.3%).

Step 10-2: Preparation of (1-(3-((6-((5-methylthiazol-2-yl) amino)-4-(morpholinomethyl) pyridin-2-yl) oxy) pyrrolidin-1-yl) prop-2-en-1-one

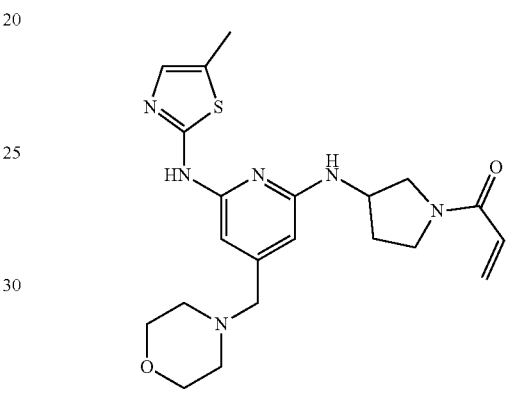

The title compound (13.2 mg, yield 65.5%) was obtained in the same manner as in Example 1, except that the intermediate obtained in step 10-1 was used instead of the intermediate obtained in step 1-3 of Example 1.

1H NMR (500 MHZ, DMSO): 10.18 (s, 1H), 6.62 (m, 1H), 6.53 (s, 1H), 6.04 (m, 1H), 5.65 (s, 1H), 5.58 (m, 1H), 5.20 (s, 1H), 4.44 (s, 2H), 3.99 (m, 1H), 3.71 (m, 2H), 3.57 (m, 4H), 3.50-3.49 (m, 2H), 2.42 (m, 4H), 2.04 (m, 2H)

Example 11: Preparation of 1-(4-((6-((5-methylthiazol-2-yl) amino)-4-(morpholinomethyl) pyridin-2-yl) oxy) piperidin-1-yl) prop-2-en-1-one

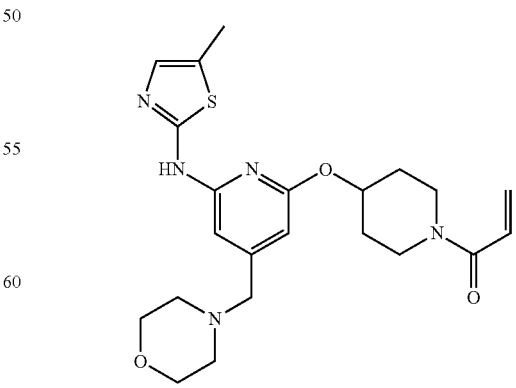

The title compound (8.5 mg, yield: 65.0%) was obtained in the same manner as in Example 10, except that in step 10-1 of Example 10, tert-butyl 4-hydroxypiperidine-1-carboxylate was used instead of tert-butyl 3-hydroxypyrrolidine-1-carboxylate.

1H NMR (500 MHZ, DMSO): 10.9 (s, 1H), 7.00 (s, 1H), 6.86-6.80 (m, 1H), 6.53 (s, 1H), 6.20 (s, 1H), 6.11-6.08 (d, 1H), 5.68-5.65 (d, 1H), 5.36-5.32 (m, 1H), 4.03 (m, 1.5H), 3.90 (m, 1.5H), 3.50 (m, 4H), 3.45 (m, 2H), 3.40 (s, 2H), 2.34 (m, 4H), 2.31 (s, 3H), 2.08-2.06 (m, 2H), 1.61-1.59 (m, 2H)

Example 12: Preparation of 1-(3-((6-((5-methylthiazol-2-yl) amino)-4-(morpholinomethyl) pyridin-2-yl) oxy) piperidin-1-yl) prop-2-en-1-one

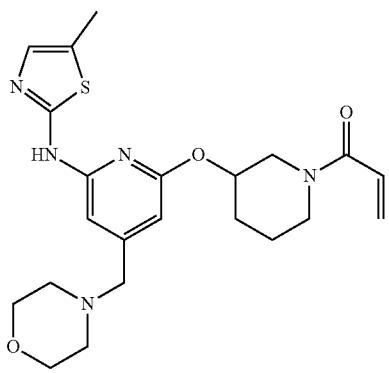 [SMILES: C=CC(=O)N1CCCC(Oc2cc(CN3CCOCC3)cc(Nc3ncc(C)s3)n2)C1]

The title compound (9.5 mg, yield: 63.0%) was obtained in the same manner as in Example 10, except that in step 10-1 of Example 10, tert-butyl 3-hydroxypiperidine-1-carboxylate was used instead of tert-butyl 3-hydroxypyrrolidine-1-carboxylate.

1H NMR (500 MHZ, DMSO): 10.994-10.92 (m, 1H), 7.00-6.99 (m, 1H), 6.95-6.85 (m, 0.5H), 6.53 (s, 1H), 6.60-6.5 (m, 0.5H), 6.15-6.13 (m, 1H), 6.10-5.96 (m, 1H), 5.74 (d, 0.5H), 5.43-5.45 (d, 0.5H), 5.25-5.15 (m, 1H), 4.01-3.95 (m, 0.5H), 3.90-3.75 (m, 2H), 3.70 (m, 0.5H), 3.55 (m, 4H), 3.40 (s, 2H), 2.34 (m, 4H), 2.37-2.20 (s, 3H), 2.09-2.04 (m, 1.5H), 1.97-1.78 (m, 2.5H), 1.50 (m, 1H)

Example 13: Preparation of (R)-1-(3-((6-((5-methylthiazol-2-yl) amino)-4-(morpholinomethyl) pyridin-2-yl) amino) piperidin-1-yl) but-2-yn-1-one Step 13-1: Preparation of (R)—N²-(5-methylthiazol-2-yl)-4-(morpholinomethyl)-N⁶-(piperidin-3-yl) pyridine-2,6-diamine

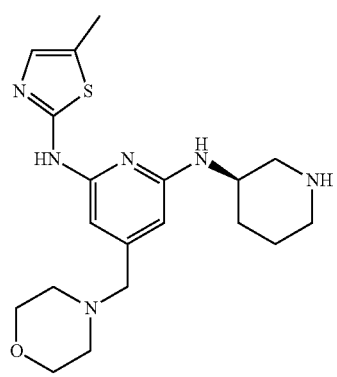 [SMILES: Cc1cnc(Nc2cc(CN3CCOCC3)cc(N[C@@H]3CCCNC3)n2)s1]

The title compound (150.0 mg, yield: 75.0%) was obtained in the same manner as in steps 1-3, 1-4, and 1-5 of Example 1, except that in steps 1-3 of Example 1, tert-butyl (R)-3-aminopiperidine-1-carboxylate was used instead of tert-butyl 3-aminopiperidine-1-carboxylate.

Step 13-2: Preparation of (R)-1-(3-((6-((5-methylthiazol-2-yl) amino)-4-(morpholinomethyl) pyridin-2-yl) amino) piperidin-1-yl) but-2-yn-1-one

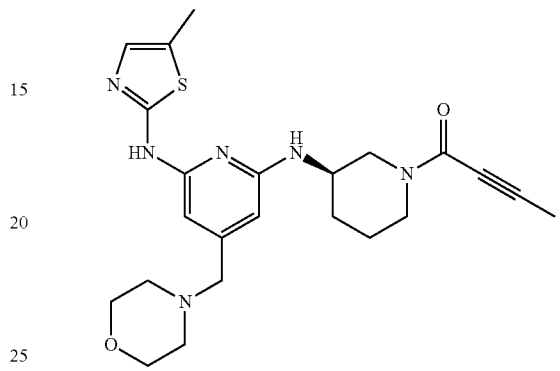

After 2-butynoic acid (21.6 mg, 1.0 eq) was dissolved in dimethylamide (1.0 mL), 1-[bis (dimethylamino) methylene]-1H-1,2,3-triazolo[4,5-b]pyridinium 3-oxidehexafluorophosphate (97.3 mg, 1.0 eq) was added thereto, and then stirred for 30 minutes. The intermediate (100.0 mg. 1.0 eq) obtained in step 13-1 was added and triethylamine (53.5 μl. 1.5 eq) was added, and then stirred for 1 hour. Water (1.0 mL) and ethyl acetate (1.0 mL) were added, and then the layers were separated. The ethyl acetate layer was dried over anhydrous sodium sulfate and then concentrated under reduced pressure. The resulting residue was purified by column chromatography (dichloromethane:methanol=10:1) to give the title compound (64.0 mg, yield: 55.0%).

1H NMR (500 MHZ, DMSO): 10.59-10.58 (d, 1H), 6.95-6.94 (m, 1H), 6.84-6.79 (m, 1H), 6.10 (m, 1H), 5.99-5.97 (m, 1H), 4.57-4.56 (m, 1H), 3.85-3.65 (m, 2H), 3.55 (m, 4H), 3.45-3.35 (m, 4H), 3.20 (s, 2H), 3.30 (m, 4H), 2.26 (s, 3H), 2.25-2.15 (m, 2H), 2.0 (d, 3H)

Example 14: Preparation of 1-(3-((6-((5-methylthiazol-2-yl) amino)-4-(morpholinomethyl) pyridin-2-yl) amino) pyrrolidin-1-yl) but-2-yn-1-one

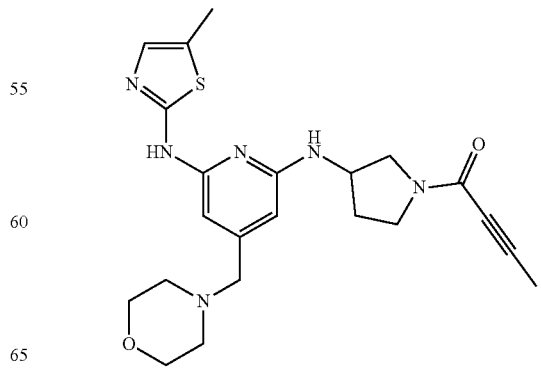

The title compound (58.6 mg, yield: 50.0%) was obtained in the same manner as in Example 13, except that in step 13-1 of Example 13, tert-butyl 3-aminopyrrolidine-1-carboxylate was used instead of tert-butyl (R)-3-aminopiperidine-1-carboxylate.

1H NMR (500 MHZ, CDCl₃): 7.03 (s, 1H), 6.11 (s, 1H), 5.96 (s, 1H), 4.56-4.54 (d, 1H), 4.42-4.40 (d, 1H), 3.73-3.71 (m, 4H), 3.33 (s, 2H), 3.30 (m, 1H), 2.93 (m, 1H), 2.45 (m, 4H), 2.38 (s, 3H), 1.47-1.40 (m, 1H)

Example 15: Preparation of(S)-1-(3-((6-((5-methylthiazol-2-yl) amino)-4-(morpholinomethyl) pyridin-2-yl) oxy) piperidin-1-yl) prop-2-en-1-one

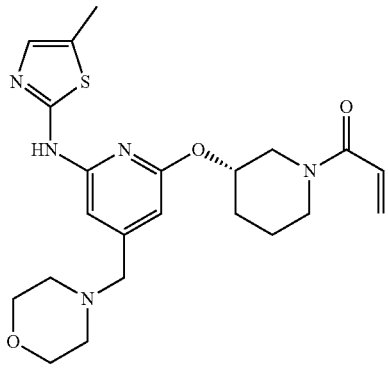 [SMILES: C=CC(=O)N1CCC[C@H](Oc2cc(CN3CCOCC3)cc(Nc3ncc(C)s3)n2)C1]

The title compound (496.0 mg, yield: 50.0%) was obtained in the same manner as in Example 10, except that in step 10-1 of Example 10, tert-butyl(S) 3-hydroxypiperidine-1-carboxylate was used instead of tert-butyl 3-hydroxypyrrolidine-1-carboxylate.

1H NMR (500 MHZ, DMSO): 10.95 (m, 1H), 6.99-6.98 (m, 1H), 6.75-6.85 (m, 0.5H), 6.50 (s, 1H), 6.4-6.5 (m, 0.5H), 5.74-5.65 (d, 1H), 6.45-6.43 (d, 1H), 5.24-5.15 (m, 1H), 4.02-4.00 (m, 0.5H), 3.82-3.81 (m, 2H), 3.78 (m, 0.5H), 3.55 (m, 4H), 3.50 (m, 0.5H), 3.15-3.14 (d, 2H), 2.32 (m, 4H), 2.27-2.24 (d, 3H), 2.06-1.96 (m, 1.5H), 1.78-1.72 (m, 2.5H), 1.51 (m, 1H)

Example 16: Preparation of (R)-1-(3-((6-((5-methylthiazol-2-yl) amino)-4-(morpholinomethyl) pyridin-2-yl) oxy) piperidin-1-yl) prop-2-en-1-one

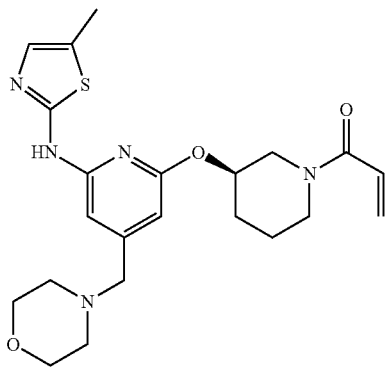 [SMILES: C=CC(=O)N1CCC[C@@H](Oc2cc(CN3CCOCC3)cc(Nc3ncc(C)s3)n2)C1]

The title compound (15.0 mg, yield: 55.0%) was obtained in the same manner as in Example 10, except that in step 10-1 of Example 10, tert-butyl (R) 3-hydroxypiperidine-1-carboxylate was used instead of tert-butyl 3-hydroxypyrrolidine-1-carboxylate.

1H NMR (500 MHZ, DMSO): 10.95 (m, 1H), 6.99-6.98 (m, 1H), 6.75-6.85 (m, 0.5H), 6.50 (s, 1H), 6.4-6.5 (m, 0.5H), 5.74-5.65 (d, 1H), 6.45-6.43 (d, 1H), 5.24-5.15 (m, 1H), 4.09-4.00 (m, 0.5H), 3.82-3.81 (m, 2H), 3.78 (m, 0.5H), 3.56 (m, 4H), 3.50 (m, 0.5H), 3.15-3.14 (d, 2H), 2.32 (m, 4H), 2.27-2.25 (d, 3H), 2.04 (m, 1.5H), 1.87-1.72 (m, 2.5H), 1.51 (m, 1H)

Example 17: Preparation of 1-(3-((4-((5-methylthiazol-2-yl) amino)-6-(morpholinomethyl) pyrimidin-2-yl) amino) piperidin-1-yl) prop-2-en-1-one

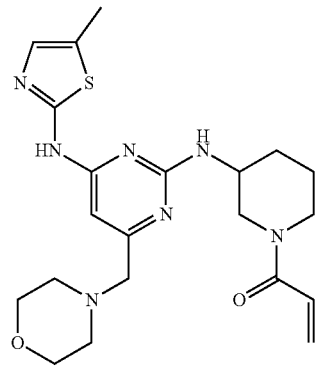 [SMILES: C=CC(=O)N1CCCC(Nc2nc(CN3CCOCC3)cc(Nc3ncc(C)s3)n2)C1]

The title compound (10.0 mg, yield: 17.5%) was obtained in the same manner as in Example 8, except that in step 8-1 of Example 8, 3-amino-1-tert-butoxy-carbonylpiperidine was used instead of tert-butyl 3-aminopyrrolidine-1-carboxylate.

1H NMR (500 MHZ, CDCl₃): 7.25 (s, 1H), 6.56-6.65 (m, 1H), 6.25-6.39 (m, 2H), 5.53 (s, 0.5H), 5.22 (s, 0.5H), 4.26 (s, 1H), 4.09 (s, 1H), 3.77 (s, 4H), 3.72 (s, 0.5H), 3.27-3.37 (m, 4.5H), 2.54 (s, 4H), 2.40 (s, 3H), 2.14 (s, 1H), 1.85 (s, 1H), 1.66-1.67 (m, 2H)

Example 18: Preparation of(S)-1-(3-((6-((5-methylthiazol-2-yl) amino)-4-(morpholinomethyl) pyridin-2-yl) amino) piperidin-1-yl) but-2-yn-1-one

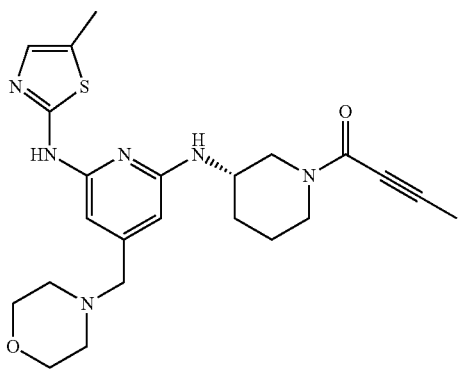 [SMILES: CC#CC(=O)N1CCC[C@H](Nc2cc(CN3CCOCC3)cc(Nc3ncc(C)s3)n2)C1]

The title compound (12.1 mg, yield: 68.0%) was obtained in the same manner as in Example 13, except that in 13-1 of Example 13, tert-butyl(S)-3-aminopiperidine-1-carboxylate was used instead of tert-butyl (R)-3-aminopiperidine-1-carboxylate.

1H NMR (500 MHZ, DMSO): 10.18 (s, 1H), 6.53 (s, 1H), 5.87 (s, 1H), 5.85 (s, 1H), 4.44 (s, 2H), 3.71-3.47 (m, 8H), 2.78 (m, 1H), 2.42 (m, 4H), 2.30 (s, 3H), 1.87-1.58 (m, 4H), 1.80 (s, 3H)

Example 19: Preparation of 1-(4-((6-((5-methylthiazol-2-yl) amino)-4-(morpholinomethyl) pyridin-2-yl) amino) piperidin-1-yl) but-2-yn-1-one

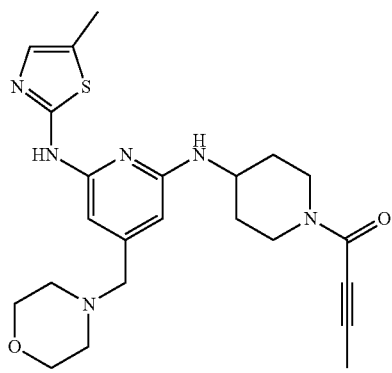 [SMILES: CC#CC(=O)N1CCC(Nc2cc(CN3CCOCC3)cc(Nc3ncc(C)s3)n2)CC1]

The title compound (8.5 mg. yield: 53.0%) was obtained in the same manner as in Example 13, except that in step 13-1 of Example 13, tert-butyl 4-aminopiperidine-1-carboxylate was used instead of tert-butyl (R)-3-aminopiperidine-1-carboxylate.

1H NMR (500 MHZ, DMSO): 10.18 (s, 1H), 6.53 (s, 1H), 5.87 (s, 1H), 5.80 (s, 1H), 4.44 (s, 2H), 3.59-3.49 (m, 8H), 2.68 (m, 1H), 2.42 (m, 4H), 2.30 (s, 3H), 1.97-1.72 (m, 4H), 1.80 (s, 3H)

Example 20: Preparation of(S)-1-(3-((4-((4-acetylpiperazin-1-yl) methyl)-6-(5-methylthiazol-2-yl) amino) pyridin-2-yl) amino) piperidin-1-yl) prop-2-en-1-one Step 20-1: Preparation of 1-((2,6-dichloropyridin-4-yl) methyl) piperazine

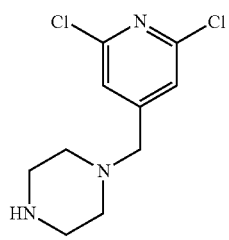 [SMILES: Clc1cc(CN2CCNCC2)cc(Cl)n1]

The title compound (11.0 mg, yield: 86.0%) was obtained in the same manner as in steps 1-1 and 1-2 of Example 1, except that in step 1-1 of Example 1, tert-butyl piperazine-1-carboxylate was used instead of morpholine.

Step 20-2: Preparation of 1-(4-((2,6-dichloropyridin-4-yl) methyl) piperazin-1-yl) ethan-1-one

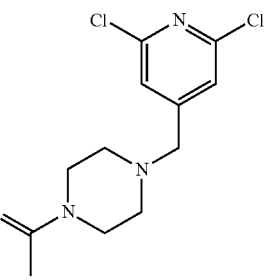

The intermediate (1.0 g. 1.0 eq) obtained in step 20-1 was dissolved in tetrahydrofuran (10.0 mL), and then triethylamine (1.1 mL, 2.0 eq) was added thereto. Acetyl chloride (434.6 μl, 1.5 eq) was added thereto and stirred for 6 hours. After concentration, ethyl acetate (10.0 mL) and water (10.0 mL) were added, and then the layers were separated. The ethyl acetate layer was dried over anhydrous sodium sulfate and then concentrated under reduced pressure. The resulting residue was purified by column chromatography (dichloromethane:methanol=10:1) to give the title compound (1.0 g, yield: 85.5%).

Step 20-3: Preparation of(S)-1-(3-((4-((4-acetylpiperazin-1-yl) methyl)-6-(5-methylthiazol-2-yl) amino) pyridin-2-yl) amino) piperidin-1-yl) prop-2-en-1-one

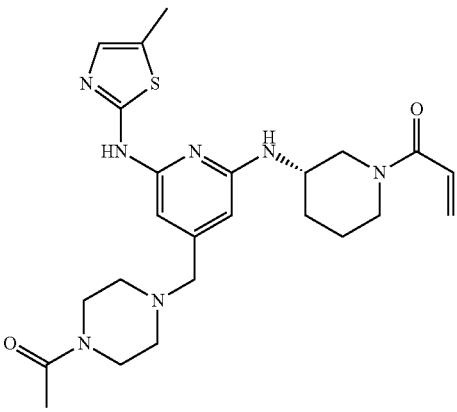 [SMILES: C=CC(=O)N1CCC[C@H](Nc2cc(CN3CCN(C(C)=O)CC3)cc(Nc3ncc(C)s3)n2)C1]

The title compound (50.0 mg, yield: 45.0%) was obtained in the same manner as in Example 1, except that the intermediate obtained in step 20-2 of Example 20 was used instead of the intermediate obtained in step 1-2 of Example 1, and tert-butyl(S)-3-aminopiperidine-1-carboxylate was used instead of tert-butyl 3-aminopiperidine-1-carboxylate in steps 1-3.

1H NMR (500 MHZ, DMSO): 10.55 (m, 1H), 6.91-6.90 (m, 1H), 6.85-6.75 (m, 0.5H), 6.57-6.48 (m, 1.5H), 6.06-6.04 (m, 1.5H), 5.99-5.96 (m, 1.5H), 5.65-5.63 (m, 0.5H), 5.43-5.41 (m, 0.5H), 4.43-4.40 (m, 0.5H), 4.14-4.10 (m, 1H), 3.98-3.88 (1.5H), 3.40 (m, 4H), 3.24 (s, 2H), 3.15-3.11 (m, 2H), 2.67 (m, 0.5H), 2.33-2.27 (m, 4H), 2.19 (s, 3H), 1.96 (d, 3H), 1.79 (m, 1H), 1.54-1.44 (m, 2.5H)

Example 21: Preparation of(S)-1-(3-((4-((5-methyl-thiazol-2-yl) amino)-6-(morpholinomethyl) pyrimidin-2-yl) amino) piperidin-1-yl) prop-2-en-1-one

Step 21-1: Preparation of methyl(S)-6-((1-(tert-butoxycarbonyl) piperidin-3-yl) amino)-2-chloropyrimidine-4-carboxylate

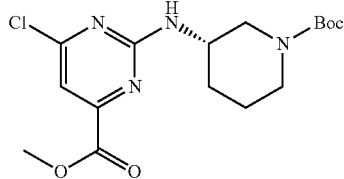 [SMILES: COC(=O)c1cc(Cl)nc(N[C@H]2CCCN(C(=O)OC(C)(C)C)C2)n1]

After methyl 2,4-dichloropyrimidine-6-carboxylate (5.0 g, 1.0 eq) was dissolved in tetrahydrofuran (100.0 mL), diisopropylethylamine (1.2 eq) and tert-butyl(S)-3-aminopiperidine-1-carboxylate (1.2 eq) were added thereto, and stirred at 80° C. for 1 hour. Upon completion of the reaction, the mixture was cooled to 30° C. or less, water (500.0 mL) and dichloromethane (500.0 mL) were added thereto, followed by extraction. The separated organic layer was dried over anhydrous sodium sulfate and then concentrated under reduced pressure. The resulting residue was purified by column chromatography (ethyl acetate:hexane=1:3) to give the title compound (1.7 g, yield: 19.3%).

Step 21-2: Preparation of tert-butyl(S)-3-((2-chloro-6-(morpholine-4-carbonyl) pyrimidin-4-yl) amino) piperidine-1-carboxylate

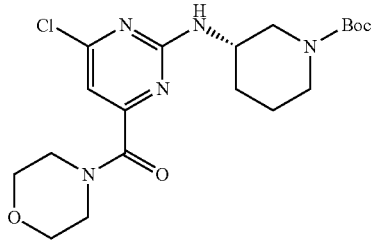 [SMILES: CC(C)(C)OC(=O)N1CCC[C@H](Nc2nc(Cl)cc(C(=O)N3CCOCC3)n2)C1]

After methyl(S)-6-((1-(tert-butoxycarbonyl) piperidin-3-yl) amino)-2-chloropyrimidine-4-carboxylate (1.7 g, 1.0 eq) obtained in step 21-1 was dissolved in tetrahydrofuran (20.0 mL), 1,5,7-triazabicyclo[4,4,0] dec-5-ene (0.3 eq) and morpholine (1.2 eq) were added thereto and stirred at room temperature for 3 hours. Upon completion of the reaction, water (200.0 mL) and dichloromethane (200.0 mL) were added thereto, followed by extraction. The separated organic layer was dried over anhydrous sodium sulfate and then concentrated under reduced pressure. The resulting residue was purified by column chromatography (ethyl acetate: methanol=19:1) to give the title compound (970.0 mg, yield: 55.7%).

Step 21-3: Preparation of tert-butyl 3-((2-((5-methylthiazol-2-yl) amino)-6-(morpholine-4-carbonyl) pyrimidin-4-yl) amino) piperidine-1-carboxylate

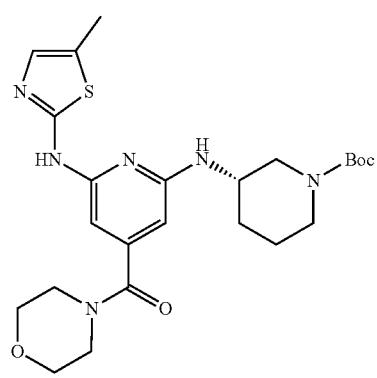 [SMILES: Cc1cnc(Nc2cc(C(=O)N3CCOCC3)cc(N[C@H]3CCCN(C(=O)OC(C)(C)C)C3)n2)s1]

After tert-butyl(S)-3-((2-chloro-6-(morpholin-4-carbonyl) pyrimidin-4-yl) amino) piperidine-1-carboxylate (950.0 mg, 1.0 eq) obtained in step 21-2 was dissolved in 1,4-dioxane (10.0 mL), palladium acetate (0.1 eq), 4,5-bis (diphenylphosphino)-9,9-dimethylxanthene (0.2 eq), cesium carbonate (3.0 eq) and 2-amino-5-methylthiazole (1.2 eq) were added thereto and reacted in a microwave reactor (160° C., 30 min). Upon completion of the reaction, water (100.0 mL) and ethyl acetate (100.0 mL) were added thereto, followed by extraction. The separated organic layer was dried over anhydrous sodium sulfate and then concentrated under reduced pressure. The resulting residue was purified by column chromatography (ethyl acetate:methanol=19:1) to give the title compound (900.0 mg, yield: 80.0%).

Step 21-4: Preparation of(S)—N²-(5-methylthiazol-2-yl)-6-(morpholinomethyl)-N⁴-(piperidin-3-yl) pyrimidine-2,4-diamine

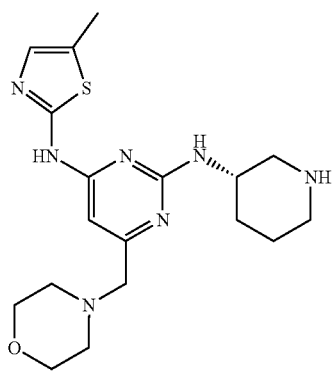 [SMILES: Cc1cnc(Nc2cc(CN3CCOCC3)nc(N[C@H]3CCCNC3)n2)s1]

After tert-butyl 3-((2-((5-methylthiazol-2-yl) amino)-6-(morpholine-4-carbonyl) pyrimidin-4-yl) amino) piperidine-1-carboxylate (500.0 mg, 1.0 eq) obtained in step 21-3 was dissolved in tetrahydrofuran (10.0 mL), 0.9M borane-tetrahydrofuran solution (3.0 eq) was added thereto and stirred at 50° C. for 5 hours. The reaction solution was cooled to 0° C., and then 6N aqueous hydrochloric acid solution (5.0 eq) was added and then stirred at 50° C. for 12 hours. The reaction solution was again cooled to 0° C., and then the pH was adjusted to 12 using 12N aqueous sodium hydroxide solution, and extracted with dichloromethane (200.0 mL) and water (200.0 mL). The separated organic layer was dried over anhydrous sodium sulfate and then concentrated under reduced pressure to give the title compound (270.0 mg, yield: 69.8%).

Step 21-5: Preparation of(S)-1-(3-((4-((5-methylthiazol-2-yl) amino)-6-(morpholinomethyl) pyrimidin-2-yl) amino) piperidin-1-yl) prop-2-en-1-one

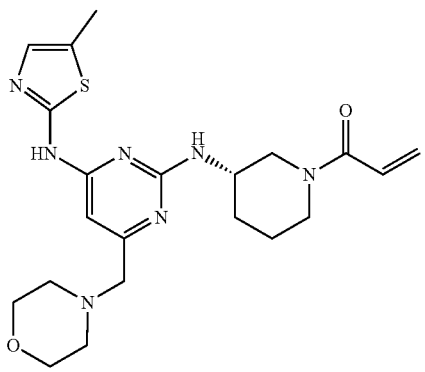 [SMILES: C=CC(=O)N1CCC[C@H](Nc2nc(CN3CCOCC3)cc(Nc3ncc(C)s3)n2)C1]

After(S)—N²-(5-methylthiazol-2-yl)-6-(morpholinomethyl)-N⁴-(piperidin-3-yl) pyrimidine-2,4-diamine (270.0 mg, 1.0 eq) obtained in steps 21-4 was dissolved in tetrahydrofuran (4.0 mL) and water (1.0 mL), sodium bicarbonate (3.0 eq) and acryloyl chloride (1.2 eq) were added thereto and stirred at 0° C. for 30 minutes. Upon completion of the reaction, water (100.0 mL) and dichloromethane (100.0 mL) were added thereto, followed by extraction. The separated organic layer was dried over anhydrous sodium sulfate and then concentrated under reduced pressure. The resulting residue was purified by column chromatography (ethyl acetate:methanol=5:1) to give the title compound (45.0 mg, yield: 14.6%).

1H NMR (500 MHZ, CDCl$_3$): 7.17 (s, 1H), 6.57-6.61 (m, 1H), 6.25-6.42 (m, 2H), 5.53 (s, 1H), 4.25 (s, 1H), 4.10 (s, 1H), 3.77 (s, 4H), 3.72 (s, 0.5H), 3.30-3.37 (m, 4.5H), 2.54 (s, 4H), 2.40 (s, 3H), 2.15 (s, 1H), 1.85 (s, 1H), 1.66-1.67 (m, 2H)

Example 22: Preparation of(S)-1-(3-((4-((4-(2-methoxyethyl) piperazin-1-yl) methyl)-6-(5-methylthiazol-2-yl) amino) pyridin-2-yl) amino) piperidin-1-yl) prop-2-en-1-one Step 22-1: Preparation of 1-((2,6-dichloropyridin-4-yl) methyl)-4-(2-methoxyethyl) piperazine

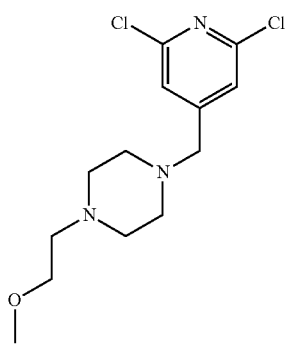 [SMILES: COCCN1CCN(Cc2cc(Cl)nc(Cl)c2)CC1]

After the intermediate (1.0 g, 1.0 eq) obtained in step 20-1 of Example 20 was dissolved in tetrahydrofuran (10.0 mL), triethylamine (1.1 mL, 2.0 eq) was added thereto. 1-Bromo-2-methoxyethane (572.0 µl, 1.5 eq) was added and stirred for 6 hours. After concentration, ethyl acetate (10.0 mL) and water (10.0 mL) were added, and then the layers were separated. The ethyl acetate layer was dried over anhydrous sodium sulfate and then concentrated under reduced pressure. The resulting residue was purified by column chromatography (dichloromethane:methanol=10:1) to give the title compound (711.1 mg, yield: 60.0%).

Step 22-2: Preparation of(S)-1-(3-((4-((4-(2-methoxyethyl) piperazin-1-yl) methyl)-6-(5-methylthiazol-2-yl) amino) pyridin-2-yl) amino) piperidin-1-yl) prop-2-en-1-one

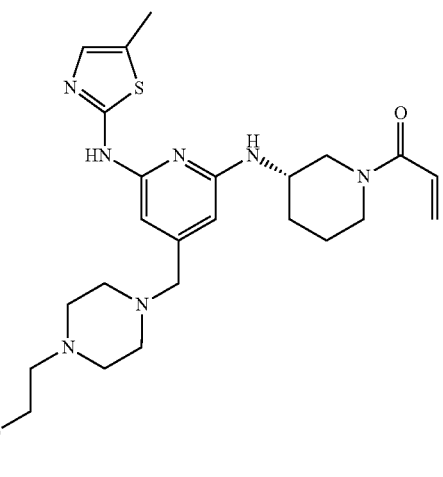

The title compound (15.0 mg, yield: 68.0%) was obtained in the same manner as in Example 1, except that the intermediate obtained in step 22-1 of Example 22 was used instead of the intermediate obtained in step 1-2 of Example 1, and tert-butyl(S)-3-aminopiperidine-1-carboxylate was used instead of tert-butyl 3-aminopiperidine-1-carboxylate in step 1-3.

1H NMR (500 MHZ, CDCl₃): 10.50 (m, 1H), 7.04-7.02 (m, 1.5H), 6.60 (m, 0.5H), 6.44-6.49 (m, 1H), 6.33-3.18 (m, 3H), 5.50-5.48 (m, 0.5H), 5.80 (m, 0.5H), 4.52-4.05 (m, 2H), 4.0-3.70 (m, 2H), 3.47 (s, 2H), 3.36 (s, 3H), 2.74-2.52 (m, 13H), 2.35 (s, 3H), 2.12-2.01 (m, 1H), 1.83 (m, 1H), 1.67 (m, 2H)

Example 23: Preparation of (S)-1-(3-((4-((5-methyl-thiazol-2-yl) amino)-6-(morpholinomethyl) pyrimidin-2-yl) amino) piperidin-1-yl) but-2-yn-1-one

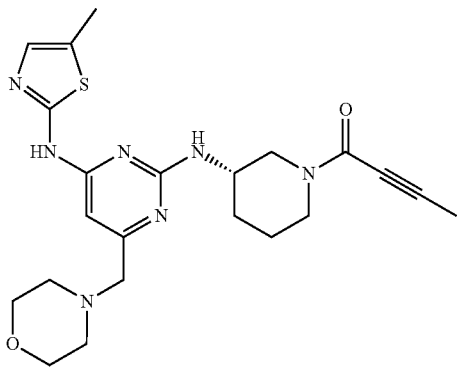 [SMILES: CC#CC(=O)N1CCC[C@H](Nc2nc(CN3CCOCC3)cc(Nc3ncc(C)s3)n2)C1]

The title compound (25.0 mg, yield 10.7%) was obtained in the same manner as in Example 21, except that in steps 21-5 of Example 21, but-2-ynoyl chloride was used instead of acryloyl chloride.

1H NMR (500 MHZ, CDCl₃): 7.17 (d, 1H), 6.34 (d, 1H), 5.30 (s, 1H), 4.32-4.36 (m, 1H), 4.22 (s, 1H), 4.01 (s, 1H), 3.78 (s, 4H), 3.41-3.45 (m, 1H), 3.39 (d, 2H), 3.36 (s, 1H), 2.54 (s, 4H), 2.45 (s, 3H), 2.17 (s, 1H), 2.04 (s, 3H), 1.62-1.72 (m, 3H)

Example 24: Preparation of (S)-1-(3-((4-((5-methyl-thiazol-2-yl) amino)-6-(morpholinomethyl) pyrimidin-2-yl) amino) pyrrolidin-1-yl) prop-2-en-1-one

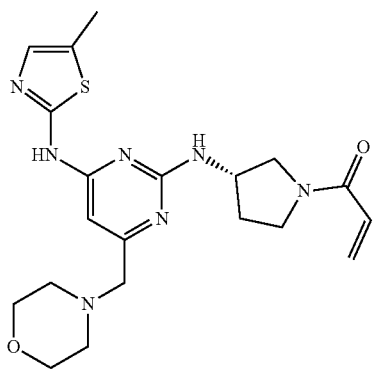 [SMILES: C=CC(=O)N1CC[C@H](Nc2nc(CN3CCOCC3)cc(Nc3ncc(C)s3)n2)C1]

The title compound (15.0 mg, yield: 10.1%) was obtained in the same manner as in Example 21, except that in step 21-1 of Example 21, tert-butyl(S)-3-aminopyrrolidine-1-carboxylate was used instead of tert-butyl(S)-3-aminopiperidine-1-carboxylate.

1H NMR (500 MHZ, CDCl₃): 11.4 (s, 1H), 7.21 (s, 1H), 6.38-6.47 (m, 2H), 5.66-5.72 (m, 1H), 5.34 (s, 1H), 4.75-4.80 (m, 1H), 3.91 (d, 0.5H), 3.68-3.77 (m, 8H), 3.51 (d, 0.5H), 3.38 (d, 2H), 2.54 (s, 4H), 2.43 (d, 3H), 2.17-2.26 (m, 1H), 1.96-2.03 (m, 1H).

Example 25: Preparation of (R)-1-(3-((4-((5-methylthiazol-2-yl) amino)-6-(morpholinomethyl) pyrimidin-2-yl) amino) piperidin-1-yl) prop-2-en-1-one

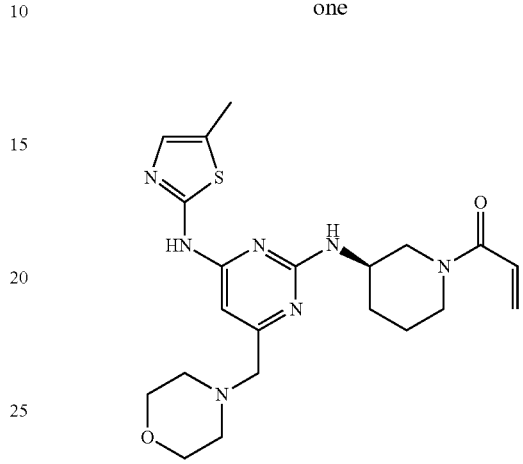

The title compound (7.0 mg, yield: 6.2%) was obtained in the same manner as in Example 21, except that in step 21-1 of Example 21, tert-butyl (R)-3-aminopiperidine-1-carboxylate was used instead of tert-butyl(S)-3-aminopiperidine-1-carboxylate.

1H NMR (500 MHZ, CDCl₃): 7.10 (s, 1H), 6.50-6.61 (m, 2H), 6.28-6.31 (m, 3H), 4.40 (s, 1H), 4.20 (s, 1H), 4.01 (s, 1H), 3.77 (s, 4H), 3.30-3.36 (m, 4H), 2.53 (s, 2H), 2.37 (s, 3H), 1.84 (s, 2H), 1.70 (m, 4H)

Example 26: Preparation of (S)-1-(3-(methyl (6-((5-methylthiazol-2-yl) amino)-4-(morpholinomethyl) pyridin-2-yl) amino) piperidin-1-yl) prop-2-en-1-one

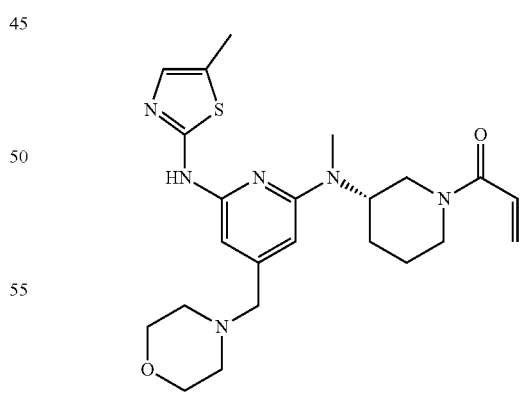

The title compound (145.0 mg, yield: 60.0%) was obtained in the same manner as in Example 1, except that in steps 1-3 of Example 1, tert-butyl(S)-3-(methylamino) piperidine-1-carboxylate was used instead of tert-butyl 3-aminopiperidine-1-carboxylate.

1H NMR (500 MHZ, DMSO): 10.62-10.60 (m, 1H), 6.92 (s, 1H), 6.91-6.81 (m, 0.5H), 6.66 (m, 0.5H), 6.22 (s, 1H), 6.09-5.99 (m, 2H), 5.66-5.64 (m, 0.5H), 5.50-5.48 (m 0.5H), 4.9 (m, 0.5H), 4.8 (m, 0.5H), 4.49-4.40 (m, 1H), 4.08-3.92 (m, 1H), 3.56 (m, 4H), 3.30 (s, 2H), 3.25-3.22 (m, 0.5H), 2.86 (s, 3H), 2.99-2.96 (m, 0.5H), 2.80-2.77 (m, 0.5H), 2.59-2.54 (m, 0.5H), 2.34 (m, 4H), 2.18 (s, 3H), 1.83-1.77 (m, 3H), 1.50 (m, 1H)

Example 27: Preparation of N-(1-(6-((5-methylthiazol-2-yl) amino)-4-(morpholinomethyl) pyridin-2-yl) piperidin-4-yl) acrylamide Step 27-1: Preparation of tert-butyl (1-(6-chloro-4-(morpholinomethyl) pyridin-2-yl) piperidin-4-yl) carbamate

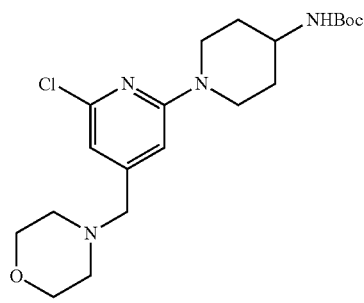 [SMILES: CC(C)(C)OC(=O)NC1CCN(c2cc(CN3CCOCC3)cc(Cl)n2)CC1]

After 4-((2,6-dichloropyridin-4-yl) methyl) morpholine (1.0 g, 3.8 mmol) was dissolved in N,N-dimethylformamide (8 mL), tert-butyl piperidin-4-ylcarbamate (0.9 g, 3.8 mmol) and cesium carbonate (1.3 g, 3.8 mmol) were added thereto, and then the mixture was stirred at reflux at 80° C. for 12 hours. Upon completion of the reaction, the reaction mixture was diluted with ethyl acetate and washed with brine. The organic layer was collected, dried over anhydrous sodium sulfate, filtered, concentrated under reduced pressure, and purified by column chromatography (hexane/ethyl acetate=1/1) to give the title compound (580 mg, yield: 35%).

Step 27-2: Preparation of tert-butyl (1-(6-((5-methylthiazol-2-yl) amino)-4-(morpholinomethyl) pyridin-2-yl) piperidin-4-yl) carbamate

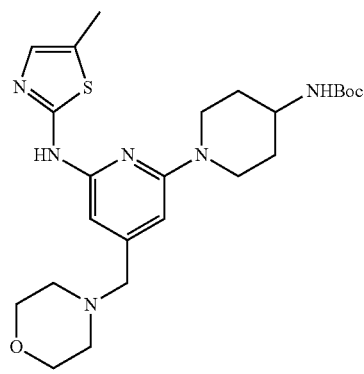 [SMILES: Cc1cnc(Nc2cc(CN3CCOCC3)cc(N3CCC(NC(=O)OC(C)(C)C)CC3)n2)s1]

After tert-butyl (1-(6-chloro-4-(morpholinomethyl) pyridin-2-yl) piperidin-4-yl) carbamate (0.5 g, 1.3 mmol) obtained in step 27-1 was dissolved in 1,4-dioxane (9 mL), 5-methylthiazol-2-amine (0.2 g, 1.4 mmol), palladium acetate (0.06 g, 0.3 mmol), Xantphos (0.3 g, 0.5 mmol) and cesium carbonate (1.2 g, 3.8 mmol) were sequentially added thereto and then reacted in a microwave reactor at 150° C. for 1 hour. Upon completion of the reaction, the reaction mixture was filtered through celite, concentrated under reduced pressure, and then purified by column chromatography (dichloromethane/methanol=9/1) to give the title compound (106 mg, yield: 17%).

Step 27-3: Preparation of N-(6-(4-aminopepyridin-1-yl)-4-(morpholinomethyl) pyridin-2-yl)-5-methylthiazol-2-amine

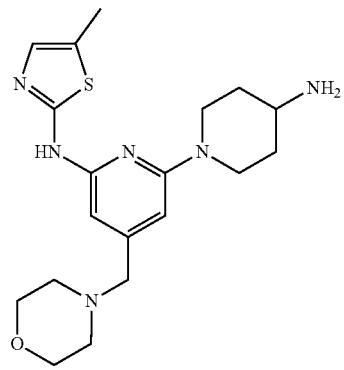 [SMILES: Cc1cnc(Nc2cc(CN3CCOCC3)cc(N3CCC(N)CC3)n2)s1]

After tert-butyl (1-(6-((5-methylthiazol-2-yl) amino)-4-(morpholinomethyl) pyridin-2-yl) piperidin-4-yl) carbamate (0.1 g, 0.2 mmol) obtained in step 27-2 was dissolved in dichloromethane (11 mL), trifluoroacetic acid (229 mg, 3.0 mmol) was added thereto, and then stirred at 20° C. for 2 hours. Upon completion of the reaction, 1N sodium hydroxide solution was added to adjust the pH to 7, diluted with ethyl acetate, and washed with brine. The organic layers were collected, dried over anhydrous sodium sulfate, filtered, and concentrated under reduced pressure to give the title compound (195 mg, yield: 100%).

Step 27-4: Preparation of N-(1-(6-((5-methylthiazol-2-yl) amino)-4-(morpholinomethyl) pyridin-2-yl) piperidin-4-yl) acrylamide

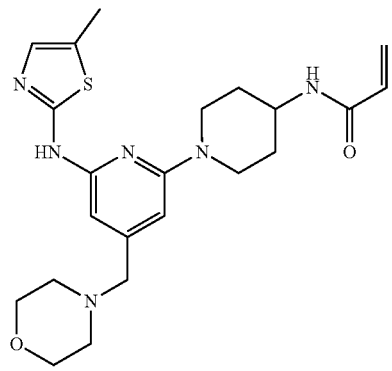 [SMILES: C=CC(=O)NC1CCN(c2cc(CN3CCOCC3)cc(Nc3ncc(C)s3)n2)CC1]

N-(6-(4-aminopepyridin-1-yl)-4-(morpholinomethyl) pyridin-2-yl)-5-methylthiazol-2-amine (0.1 g, 0.2 mmol) obtained in step 27-3 was dissolved in tetrahydrofuran (6 mL) and water (2 mL), and then cooled to 0° C., and sodium bicarbonate (0.08 g, 1.0 mmol) was added thereto. Acryloyl chloride (0.02 mL, 0.3 mmol) was slowly added to the reaction solution, and then stirred at 0° C. for 10 minutes. Upon completion of the reaction, the reaction mixture was diluted with ethyl acetate, washed with brine, concentrated under reduced pressure, and purified by column chromatography (dichloromethane/methanol=9/1) to give the title compound (33 mg, yield: 37%).

1H NMR (500 MHZ, CDCl$_3$): 7.02 (s, 1H), 6.30-6.32 (m, 1H), 6.15-6.20 (m, 1H), 6.01-6.10 (m, 1H), 5.60-5.62 (m, 1H), 5.41-5.45 (m, 1H), 4.35-4.38 (m, 2H), 4.15-4.20 (m, 1H), 3.78 (s, 4H), 3.38 (s, 2H), 3.07-3.12 (m, 2H), 2.45 (s, 4H), 2.37 (s, 3H), 2.10-2.12 (m, 2H), 1.50-1.60 (m, 2H).

Example 28: Preparation of 1-(6-(6-((5-methylthiazol-2-yl) amino)-4-(morpholinomethyl) pyridin-2-yl) octahydro-1H-pyrrolo[2,3-c]pyridin-1-yl) prop-2-en-1-one

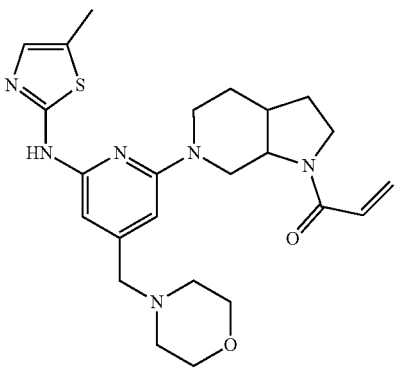 [SMILES: C=CC(=O)N1CCC2CCN(c3cc(CN4CCOCC4)cc(Nc4ncc(C)s4)n3)CC21]

The title compound (7 mg, yield 19%) was obtained in the same manner as in Example 27, except that in step 27-1 of Example 27, tert-butyl octahydro-1H-pyrrolo[2,3-c] pyridin-1-carboxylate was used instead of tert-butyl piperidin-4-ylcarbamate.

1H NMR (500 MHZ, CDCl$_3$): 6.97 (s, 1H), 6.40-6.47 (m, 2H), 6.07-6.20 (m, 2H), 5.67-5.71 (m, 1H), 4.32-4.42 (m, 2H), 4.05-4.15 (m, 2H), 3.70 (s, 4H), 3.58-3.62 (m, 2H), 3.50 (s, 2H), 3.32 (s, 2H), 2.95-3.05 (m, 2H), 2.50-2.52 (m, 1H), 2.47 (s, 4H), 2.37 (s, 3H), 1.85-1.90 (m, 1H).

Example 29: Preparation of 1-(6-(6-((5-methylthiazol-2-yl) amino)-4-(morpholinomethyl) pyridin-2-yl) octahydro-1H-pyrrolo[2,3-c]pyridin-1-yl) but-2-yn-1-one

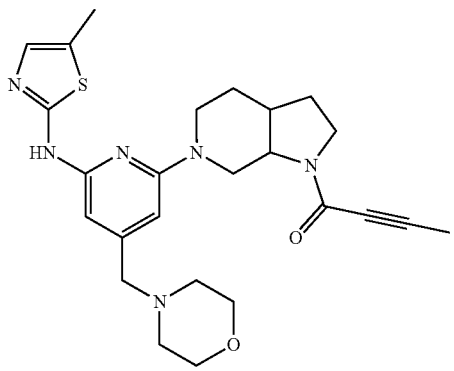 [SMILES: CC#CC(=O)N1CCC2CCN(c3cc(CN4CCOCC4)cc(Nc4ncc(C)s4)n3)CC21]

The title compound (12 mg, yield: 15%) was obtained in the same manner as in Example 27, except that in step 27-1 of Example 27, tert-butyl octahydroxy-1H-pyrrolo[2,3-c] pyridin-1-carboxylate was used instead of tert-butyl piperidin-4-ylcarbamate, and in step 27-4, but-2-ynoyl chloride was used instead of acryloyl chloride.

1H NMR (500 MHZ, CDCl$_3$): 6.98 (s, 1H), 6.06-6.10 (m, 2H), 4.20-4.25 (m, 2H), 3.67 (s, 3H), 3.60-3.65 (m, 2H), 3.41-3.50 (m, 2H), 3.31-3.37 (m, 2H), 2.95-3.05 (m, 2H), 2.39-2.50 (m, 4H), 2.38 (s, 3H), 2.27-2.35 (m, 2H), 1.87-1.95 (m, 4H), 1.75-1.87 (m, 2H).

Example 30: Preparation of 1-(6-((6-((5-methylthiazol-2-yl) amino)-4-(morpholinomethyl) pyridin-2-yl) amino)-2-azaspiro[3.3] heptan-2-yl) prop-2-en-1-one

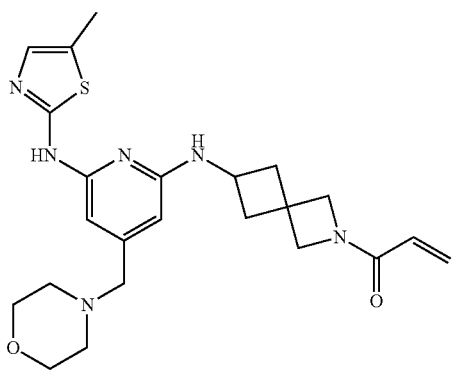 [SMILES: C=CC(=O)N1CC2(CC(Nc3cc(CN4CCOCC4)cc(Nc4ncc(C)s4)n3)C2)C1]

The title compound (5 mg, yield 11%) was obtained in the same manner as in Example 1, except that in step 1-3 of Example 1, tert-butyl 6-amino-2-azaspiro[3.3] heptane-2-carboxylate was used instead of tert-butyl 3-aminopiperidine-1-carboxylate.

1H NMR (500 MHZ, CDCl$_3$): 6.95 (s, 1H), 6.40-6.46 (m, 2H), 6.25-6.30 (m, 1H), 6.18 (m, 1H), 5.69-5.74 (m, 1H), 3.82 (s, 2H), 3.72-3.77 (m, 2H), 3.65-3.70 (m, 2H), 3.10-3.12 (m, 1H), 2.39-2.50 (m, 4H), 2.36 (s, 3H), 1.87-1.95 (m, 4H), 1.85-1.87 (m, 2H), 1.60-1.62 (m, 2H).

Example 31: Preparation of(S)-1-(3-((4-((5-methyl-thiazol-2-yl) amino)-6-(piperidin-1-ylmethyl) pyrimidin-2-yl) amino) piperidin-1-yl) prop-2-en-1-one

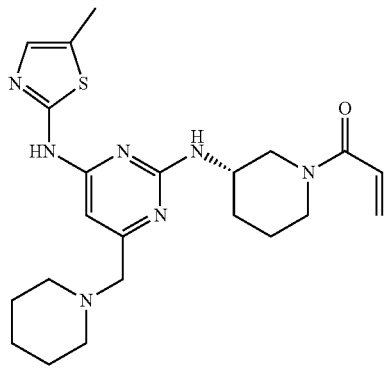 [SMILES: C=CC(=O)N1CCC[C@H](Nc2nc(CN3CCCCC3)cc(Nc3ncc(C)s3)n2)C1]

The title compound (1.0 mg, yield: 1.5%) was obtained in the same manner as in Example 21, except that in step 21-2 of Example 21, piperidine was used instead of morpholine.

1H NMR (500 MHZ, CDCl$_3$): 7.05 (s, 1H), 6.50-6.63 (m, 2H), 6.21-6.28 (m, 2H), 5.70 (s, 0.5H), 5.54 (s, 0.5H), 4.50-4.70 (m, 1H), 4.20-4.40 (m, 4H), 3.31 (s, 2H), 3.20-3.30 (m, 4H), 2.36 (s, 3H), 1.33-1.72 (m, 10H)

Example 32: Preparation of(S)-1-(3-((4-((4-eth-ylpiperazin-1-yl) methyl)-6-(5-methylthiazol-2-yl) amino) pyrimidin-2-yl) amino) piperidin-1-yl) prop-2-en-1-one

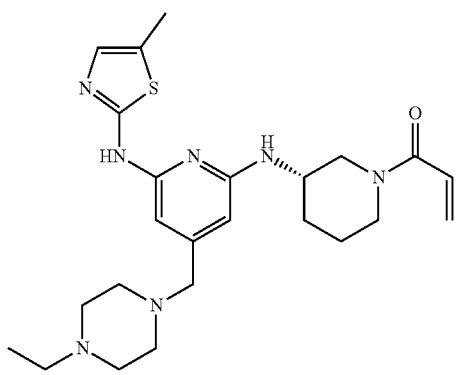 [SMILES: C=CC(=O)N1CCC[C@H](Nc2cc(CN3CCN(CC)CC3)cc(Nc3ncc(C)s3)n2)C1]

The title compound (0.5 mg, yield: 1.1%) was obtained in the same manner as in Example 21, except that in step 21-2 of Example 21, 1-ethylpiperazine was used instead of morpholine.

1H NMR (500 MHZ, CDCl$_3$): 7.06 (s, 1H), 6.50-6.63 (m, 1H), 6.19-6.28 (m, 2H), 5.71 (s, 0.5H), 5.54 (s, 0.5H), 4.20-4.44 (m, 1H), 3.51-3.60 (m, 1H), 3.37 (s, 2H), 3.27-3.32 (m, 1H), 2.52-2.57 (m, 4H), 2.41-2.46 (m, 4H), 2.36 (s, 3H), 1.66-1.84 (m, 8H), 1.08 (t, 3H)

Example 33: Preparation of(S)-1-(3-((4-((1-meth-ylpiperidin-4-yl) oxy)-6-((5-methylthiazol-2-yl) amino) pyridin-2-yl) amino) piperidin-1-yl) prop-2-en-1-one

Step 33-1: Preparation of tert-butyl 4-((2,6-dichloropyridin-4-yl) oxy) piperidine-1-carboxylate

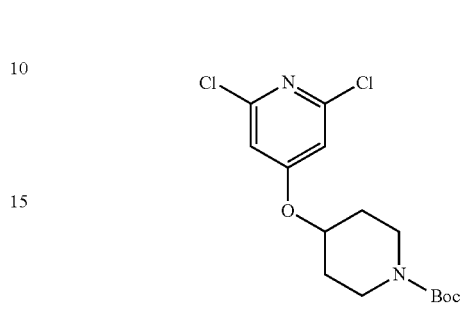

After 1-(tert-butoxycarbonyl)-4-hydroxypiperidine (5.5 g, 1.0 eq) was dissolved in dimethylformamide (50.0 mL), 60% sodium hydride (3.0 eq) was added and reacted at 0° C. for 10 minutes, then 2,4,6-trichloropyridine (1.0 eq) was added and reacted for 30 minutes. Upon completion of the reaction, water (500.0 mL) and ethyl acetate (500.0 mL) were added thereto, followed by extraction. The separated organic layer was dried over anhydrous sodium sulfate and then concentrated under reduced pressure. The resulting residue was purified by column chromatography (ethyl acetate:hexane=1:5) to give the title compound (5.1 g, yield: 53.7%).

Step 33-2: Preparation of 2,6-dichloro-4-(piperidin-4-yloxy) pyridine

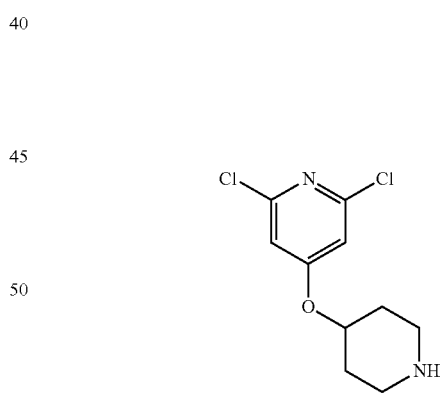

To tert-butyl 4-((2,6-dichloropyridin-4-yl) oxy) piperidine-1-carboxylate (5.0 g, 1.0 eq) obtained in step 33-1,4M hydrochloric acid-dioxane solution (50.0 mL) was added and reacted at room temperature for 30 minutes. Upon completion of the reaction, the reaction solution was cooled at 0° C., and then the pH was adjusted to 12 using 12N sodium hydroxide aqueous solution, and water (250 mL) and ethyl acetate (500.0 mL) were added thereto, followed by extraction. The separated organic layer was dried over anhydrous sodium sulfate and then concentrated under reduced pressure to give the title compound (2.4 g, yield: 68.2%).

Step 33-3: Preparation of 2,6-dichloro-4-((1-methylpiperidin-4-yl) oxy) pyridine

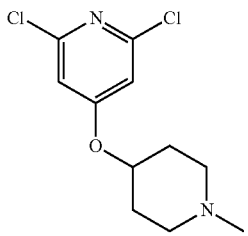 [SMILES: CN1CCC(Oc2cc(Cl)nc(Cl)c2)CC1]

After 2,6-dichloro-4-(piperidin-4-yloxy) pyridine (2.4 g, 1.0 eq) obtained in step 33-2 was dissolved in methanol (50.0 mL) and dichloromethane (50.0 mL), formaldehyde solution (1.0 eq), acetic acid (0.1 eq), and sodium triacetoxyborohydride (2.0 eq) were added thereto and reacted at room temperature for 30 minutes. Upon completion of the reaction, water (500.0 mL) and dichloromethane (500.0 mL) were added thereto, followed by extraction. The separated organic layer was dried over anhydrous sodium sulfate and then concentrated under reduced pressure to give the title compound (5.1 g, yield: 89.8%).

Step 33-4: Preparation of tert-butyl(S)-3-((6-chloro-4-((1-methylpiperidin-4-yl) oxy) pyridin-2-yl) amino) piperidine-1-carboxylate

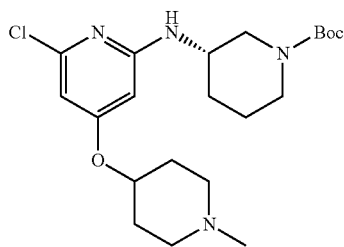 [SMILES: CN1CCC(Oc2cc(Cl)nc(N[C@H]3CCCN(C(=O)OC(C)(C)C)C3)c2)CC1]

After 2,6-dichloro-4-((1-methylpiperidin-4-yl) oxy) pyridine (2.0 g, 1.0 eq) obtained in step 33-3 was dissolved in 1,4-dioxane (20.0 mL), palladium acetate (0.1 eq), 4,5-bis(diphenylphosphino)-9,9-dimethylxanthene (0.2 eq), cesium carbonate (3.0 eq), and 2-amino-5-methylthiazole (1.2 eq) were added thereto and reacted in a microwave reactor (150° C., 30 min). Upon completion of the reaction, water (250.0 mL) and dichloromethane (250.0 mL) were added thereto, followed by extraction. The separated organic layer was dried over anhydrous sodium sulfate and then concentrated under reduced pressure. The resulting residue was purified by column chromatography (ethyl acetate:methanol=1:1) to give the title compound (900.0 mg, yield: 27.7%).

Step 33-5: Preparation of tert-butyl(S)-3-((4-((1-methylpiperidin-4-yl) oxy)-6-((5-methylthiazol-2-yl) amino) pyridin-2-yl) amino) piperidine-1-carboxylate

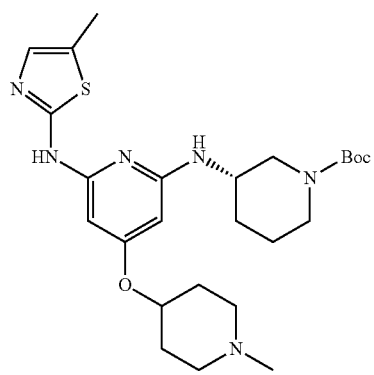 [SMILES: Cc1cnc(Nc2cc(OC3CCN(C)CC3)cc(N[C@H]3CCCN(C(=O)OC(C)(C)C)C3)n2)s1]

After tert-butyl(S)-3-((6-chloro-4-((1-methylpiperidin-4-yl) oxy) pyridin-2-yl) amino) piperidine-1-carboxylate (900.0 mg, 1.0 eq) obtained in step 33-4 was dissolved in 1,4-dioxane (20.0 ml), palladium acetate (0.1 eq), 4,5-bis(diphenylphosphino)-9,9-dimethylxanthene (0.2 eq), cesium carbonate (3.0 eq), and 2-amino-5-methylthiazole (1.1 eq) were added thereto, and reacted in a microwave reactor (160° C., 2 hr). Upon completion of the reaction, water (250.0 mL) and ethyl acetate (250.0 mL) were added thereto, followed by extraction. The separated organic layer was dried over anhydrous sodium sulfate and then concentrated under reduced pressure. The resulting residue was purified by column chromatography (ethyl acetate:methanol=1:1) to give the title compound (300.0 mg, yield: 28.3%).

Step 33-6: Preparation of(S)-4-((1-methylpiperidin-4-yl) oxy)-$N^2$-(5-methylthiazol-2-yl)-$N^6$-(piperidin-3-yl) pyridin-2,6-diamine

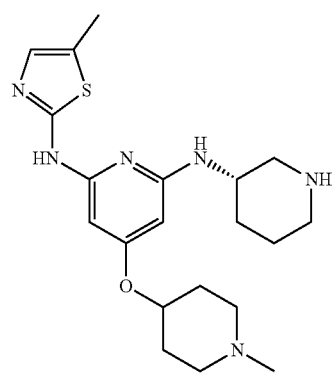 [SMILES: Cc1cnc(Nc2cc(OC3CCN(C)CC3)cc(N[C@H]3CCCNC3)n2)s1]

To tert-butyl(S)-3-((4-((1-methylpiperidin-4-yl) oxy)-6-((5-methylthiazol-2-yl) amino) pyridin-2-yl) amino) piperidine-1-carboxylate (300.0 mg, 1.0 eq) obtained in steps 33-5, 1.25M hydrochloric acid-methanol solution (5.0 mL) was added and reacted at 50° C. for 12 hours. Upon completion of the reaction, the reaction solution was cooled at 0° C., and then the pH was adjusted to 8~9 using saturated sodium bicarbonate aqueous solution, and water (100.0 mL) and ethyl acetate (100.0 mL) were added thereto, followed by extraction. The separated organic layer was dried over anhydrous sodium sulfate and then concentrated under reduced pressure to give the title compound (150.0 mg, yield: 62.5%).

Step 33-7: Preparation of(S)-1-(3-((4-((1-methylpiperidin-4-yl) oxy)-6-((5-methylthiazol-2-yl) amino) pyridin-2-yl) amino) piperidin-1-yl) prop-2-en-1-one

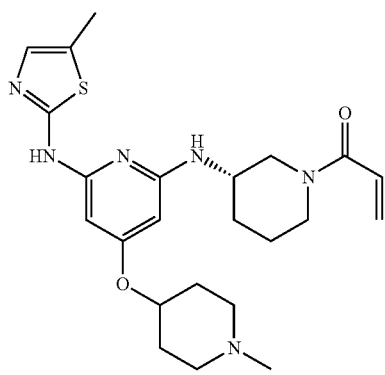 [SMILES: C=CC(=O)N1CCC[C@H](Nc2cc(OC3CCN(C)CC3)cc(Nc3ncc(C)s3)n2)C1]

After(S)-4-((1-methylpiperidin-4-yl) oxy)-N²-(5-methylthiazol-2-yl)-N⁶-(piperidin-3-yl) pyridin-2,6-diamine (130.0 mg, 1.0 eq) obtained in steps 33-6 was dissolved in tetrahydrofuran (2.4 mL) and water (0.6 mL), sodium bicarbonate (3.0 eq) and acryloyl chloride (1.2 eq) were added and reacted at room temperature for 1 hour. Upon completion of the reaction, water (100.0 mL) and dichloromethane (100.0 mL) were added thereto, followed by extraction. The separated organic layer was dried over anhydrous sodium sulfate and then concentrated under reduced pressure. The resulting residue was purified by column chromatography (ethyl acetate:methanol=1:1) to give the title compound (1.0 mg, yield: 0.7%).

1H NMR (500 MHZ, CDCl$_3$): 6.99 (s, 1H), 6.60-6.65 (m, 0.5H), 6.46-6.51 (m, 0.5H), 6.32 (d, 0.5H), 6.24 (d, 0.5H), 5.71 (s, 1H), 5.53-5.59 (m, 1H), 5.40 (d, 2H), 4.46 (s, 0.5H), 4.31 (s, 2H), 4.29 (s, 0.5H), 3.93 (d, 1H), 3.86 (s, 0.5H), 3.71 (s, 0.5H), 3.48 (s, 1H), 3.37-3.39 (m, 1H), 2.69 (s, 2H), 2.34 (s, 3H), 2.30 (s, 5H), 2.11 (s, 1H), 2.00 (s, 2H), 1.81 (s, 3H), 1.65 (s, 2H)

Example 34: Preparation of(S)-3-(4-((2-((1-acryloylpiperidin-3-yl) amino)-6-((5-methylthiazol-2-yl) amino) pyridin-4-yl) methyl) piperazin-1-yl) propanenitrile Step 34-1: Preparation of 3-(4-((2,6-dichloropyridin-4-yl) methyl) piperazin-1-yl) propanenitrile

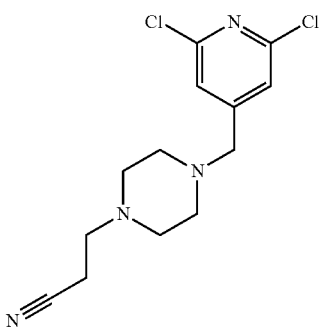 [SMILES: N#CCCN1CCN(Cc2cc(Cl)nc(Cl)c2)CC1]

The title compound (7.1 g, yield: 57.2%) was obtained in the same manner as in steps 1-1 and 1-2 of Example 1, except that in step 1-1 of Example 1, 3-(piperazin-1-yl) propanenitrile was used instead of morpholine.

Step 34-2: Preparation of t-butyl(S)-3-((4-((4-(2-cyanoethyl) piperazin-1-yl) methyl)-6-((5-methylthiazol-2-yl) amino) pyridin-2-yl) amino) piperidine-1-carboxylate

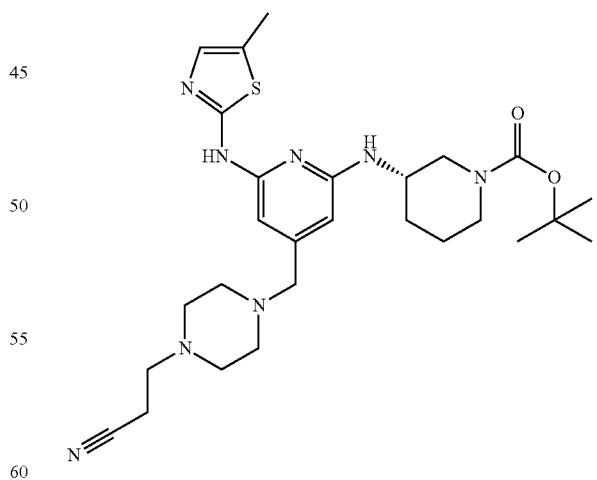

The title compound (400 mg, yield: 76.0%) was obtained in the same manner as in steps 1-3 and 1-4 of Example 1, except that the intermediate obtained in step 34-1 was used instead of the intermediate obtained in step 1-3 of Example 1, and t-butyl(S)-3-aminopiperidine-1-carboxylate was used instead of t-butyl 3-aminopiperidine-1-carboxylate.

Step 34-3: Preparation of(S)-3-(4-((2-((5-methylthi- azol-2-yl) amino)-6-(piperidin-3-ylamino) pyridin- 4-yl) methyl) piperazine-1-yl) propanenitrile

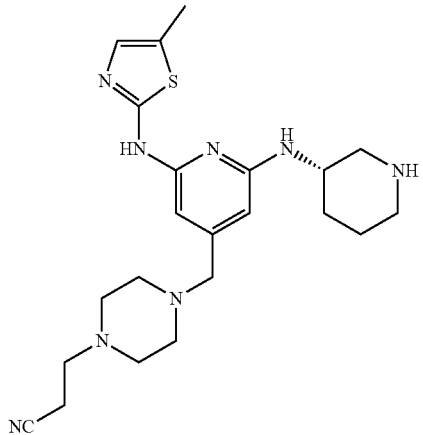 [SMILES: Cc1cnc(Nc2cc(CN3CCN(CCC#N)CC3)cc(N[C@H]3CCCNC3)n2)s1]

After tert-butyl(S)-3-((4-((4-(2-cyanoethyl) piperazin-1-yl) methyl)-6-((5-methylthiazol-2-yl) amino) pyridin-2-yl) amino) piperidine-1-carboxylate (100.0 mg, 1.0 eq) obtained in step 34-2 was dissolved in dichloromethane (10.0 mL), trifluoroacetic acid (141.5 μL, 10.0 eq) was added thereto at room temperature, and the reactant was allowed to react at room temperature for 2 hours. The reaction mixture was neutralized with 2.0M aqueous sodium hydroxide solution and then extracted with dichloromethane. The separated organic layer was dried over anhydrous sodium sulfate and then concentrated under reduced pressure. The resulting residue was purified by column chromatography to give 65.0 mg (yield: 77.6%) of the title compound as a brown solid.

Step 34-4: Preparation of(S)-3-(4-((2-((1-acryloylpi- peridin-3-yl) amino)-6-((5-methylthiazol-2-yl) amino) pyridin-4-yl) methyl) piperazin-1-yl) propa- nenitrile

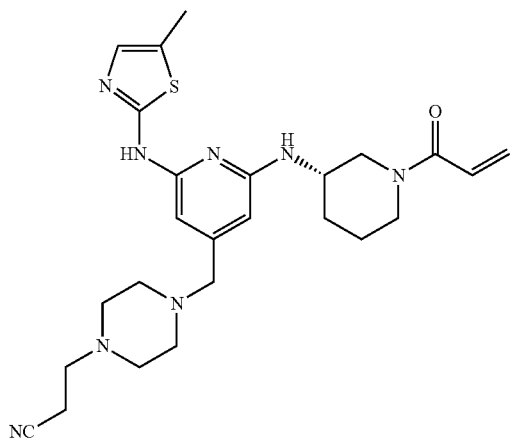 [SMILES: C=CC(=O)N1CCC[C@H](Nc2cc(CN3CCN(CCC#N)CC3)cc(Nc3ncc(C)s3)n2)C1]

After(S)-3-(4-((2-((5-methylthiazol-2-yl) amino)-6-(piperidin-3-ylamino) pyridin-4-yl) methyl) piperazine-1-yl) propanenitrile (65.0 mg, 1.0 eq) obtained in step 34-3 was dissolved in tetrahydrofuran (5.0 mL) and water (1.0 mL), sodium hydrogen carbonate (24.8 mg, 2.0 eq) was added at room temperature, and reacted for 30 minutes. Acryloyl chloride (24.0 μL, 2.0 eq) was added to the mixture at room temperature. The reactant was allowed to react at room temperature for 10 minutes, then methanol was added, and water and ethyl acetate were added thereto, followed by extraction. The separated organic layer was dried over anhydrous sodium sulfate and then concentrated under reduced pressure. The resulting residue was purified by column chromatography to give 25.0 mg (yield: 34.1%) of the title compound as a brown solid.

1H NMR (500 MHZ, MeOD): 6.89 (d, 1H), 6.84-6.79 (m, 1H), 6.55-6.50 (m, 1H), 6.20-6.03 (m, 2H), 5.47 (d, 1H), 4.61 (d, 1H), 4.38-4.30 (m, 1H), 4.29-4.18 (m, 1H), 4.09-3.97 (m, 2H), 3.34 (s, 3H), 2.83 (t, 1H), 2.61-4.24 (m, 14H), 2.19-2.11 (m, 1H), 1.97-1.88 (m, 1H), 1.71-1.55 (m, 1H).

Example 35: Preparation of(S)-1-(3-((4-methyl-6-((5-methylthiazol-2-yl) amino) pyridin-2-yl) amino) piperidin-1-yl) prop-2-en-1-one

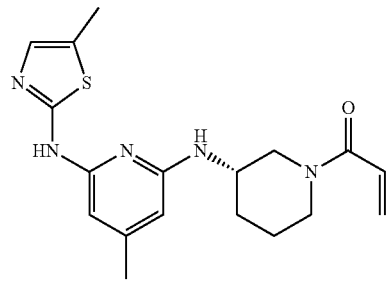 [SMILES: C=CC(=O)N1CCC[C@H](Nc2cc(C)cc(Nc3ncc(C)s3)n2)C1]

The title compound (15 mg, yield: 21%) was obtained in the same manner as in Example 1, except that in steps 1-3 of Example 1, 2,6-dichloro-4-methylpyridine was used instead of 4-((2,6-dichloropyridin-4-yl) methyl) morpho- line.

1H NMR (500 MHZ, CDCl₃): 6.94-6.98 (m, 1H), 6.45-6.50 (m, 1H), 6.20-6.25 (m, 1H), 5.97-6.00 (m, 1H), 5.75-5.85 (m, 1H), 5.47-5.51 (m, 1H), 4.22-4.40 (m, 2H), 3.78-3.96 (m, 2H), 3.70-3.72 (m, 1H), 3.27-3.40 (m, 2H), 2.36 (s, 3H), 2.21 (s, 3H), 1.85-1.90 (m, 1H), 1.75-1.80 (m, 1H).

Example 36: Preparation of(S)-1-(3-((6-((5-methyl- thiazol-2-yl) amino)-4-(pyridin-3-ylmethyl) pyridin- 2-yl) amino) piperidin-1-yl) prop-2-en-1-one Step 36-1: Preparation of 2,6-dichloro-4-(pyridin-3-ylmethyl) pyridine

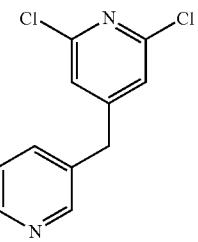

After (2,6-dichloropyridin-4-yl) boronic acid (0.5 g, 2.6 mmol) was dissolved in 1,4-dioxane (13 mL) and water (1.6 mL), 3-(bromomethyl) pyridine hydrogen bromide (0.7 g, 1.6 mmol), potassium carbonate (1.8 g, 13.0 mmol), [1,1'-bis (diphenylphosphino) ferrocene] dichloropalladium (II) (0.1 g, 0.2 mmol) were sequentially added thereto, and then the mixture was stirred at reflux at 110° C. for 2 hours. Upon completion of the reaction, the reaction mixture was concentrated under reduced pressure and purified by column chromatography (hexane/ethyl acetate=1/1) to give the title compound (420 mg, yield: 67%).

Step 36-2: Preparation of tert-butyl(S)-3-((6-chloro-4-(pyridin-3-ylmethyl) pyridin-2-yl) amino) piperidine-1-carboxylate

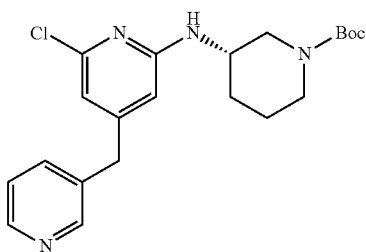 [SMILES: CC(C)(C)OC(=O)N1CCC[C@H](Nc2cc(Cc3cccnc3)cc(Cl)n2)C1]

After 2,6-dichloro-4-(pyridin-3-ylmethyl) pyridine (1.7 g, 7.1 mmol) obtained in step 36-1 was dissolved in 1,4-dioxane (24 mL), tert-butyl(S)-3-aminopiperidine-1-carboxylate (1.6 g, 7.8 mmol), palladium acetate (0.2 g, 0.7 mmol), Xantphos (0.8 g, 1.4 mmol) and sodium carbonate (2.3 g, 21.3 mmol) were sequentially added thereto, and then stirred at reflux at 100° C. for 12 hours. Upon completion of the reaction, the reaction mixture was filtered through celite, concentrated under reduced pressure, and purified by column chromatography (ethyl acetate 100%) to give the title compound (280 mg, yield: 15%).

Step 36-3: Preparation of tert-butyl 3-((6-((5-methylthiazol-2-yl) amino)-4-(pyridin-3-ylmethyl) pyridin-2-yl) amino) piperidine-1-carboxylate

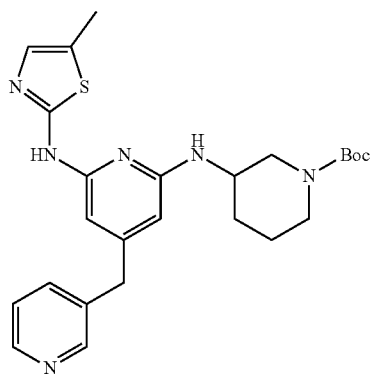 [SMILES: Cc1cnc(Nc2cc(Cc3cccnc3)cc(NC3CCCN(C(=O)OC(C)(C)C)C3)n2)s1]

After tert-butyl(S)-3-((6-chloro-4-(pyridin-3-ylmethyl) pyridin-2-yl) amino) piperidine-1-carboxylate (0.4 g, 2.3 mmol) obtained in step 36-2 was dissolved in 1,4-dioxane (6 mL), 5-methylthiazol-2-amine (0.1 g, 2.6 mmol), palladium acetate (0.02 g, 0.2 mmol), Xantphos (0.1 g, 0.5 mmol) and cesium carbonate (0.9 g, 7.0 mmol) were sequentially added thereto and reacted in a microwave reactor at 150° C. for 1 hour. Upon completion of the reaction, the reaction mixture was filtered through celite, concentrated under reduced pressure, and purified by column chromatography (dichloromethane/methanol=9/1) to give the title compound (360 mg, yield: 84%).

Step 36-4: Preparation of $N^2$-(5-methylthiazol-2-yl)-$N^6$-(piperidin-3-yl)-4-(pyridin-3-ylmethyl) pyridin-2,6-diamine

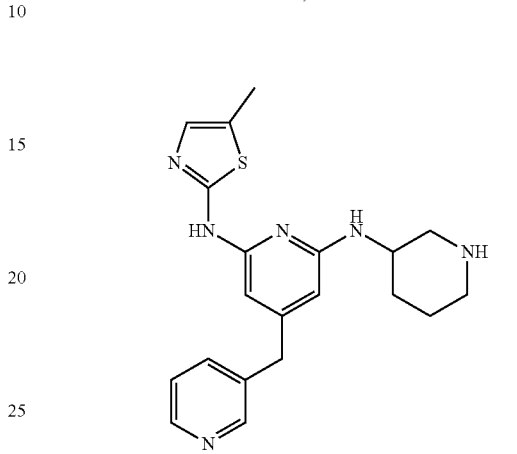

After tert-butyl 3-((6-((5-methylthiazol-2-yl) amino)-4-(pyridin-3-ylmethyl) pyridin-2-yl) amino) piperidine-1-carboxylate (0.2 g, 0.3 mmol) obtained in step 36-3 was dissolved in dichloromethane (2 mL), trifluoroacetic acid (0.5 mL, 6.6 mmol) was added thereto, and then stirred at 20° C. for 2 hours. Upon completion of the reaction, 1N sodium hydroxide solution was added to adjust the pH to 7, diluted with ethyl acetate, and washed with brine. The organic layer was collected, dried over anhydrous sodium sulfate, filtered, and concentrated under reduced pressure to give the title compound (180 mg, yield: 100%).

Step 36-5: Preparation of(S)-1-(3-((6-((5-methylthiazol-2-yl) amino)-4-(pyridin-3-ylmethyl) pyridin-2-yl) amino) piperidin-1-yl) prop-2-en-1-one

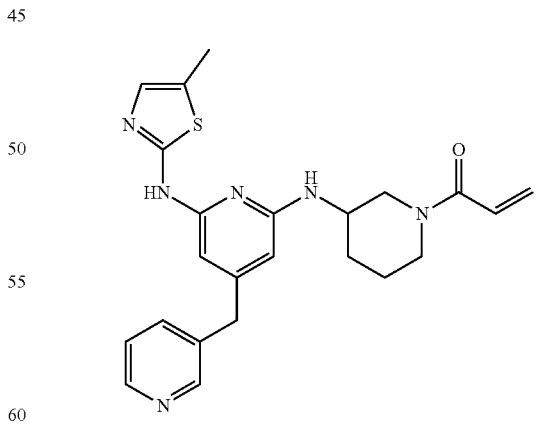

$N^2$-(5-methylthiazol-2-yl)-$N^6$-(piperidin-3-yl)-4-(pyridin-3-ylmethyl) pyridin-2,6-diamine (0.2 g, 0.4 mmol) obtained in step 36-4 was dissolved in tetrahydrofuran (6 mL) and water (2 mL), and then cooled to 0° C., and sodium bicarbonate (0.1 g, 1.1 mmol) was added thereto. Acryloyl chloride (0.05 mL, 0.6 mmol) was slowly added to the reaction solution, and then stirred at 0° C. for 10 minutes. Upon completion of the reaction, the reaction mixture was diluted with ethyl acetate, washed with brine, concentrated under reduced pressure, and purified by column chromatography (dichloromethane/methanol=9/1) to give the title compound (19 mg, yield: 25%).

¹H NMR (500 MHZ, CDCl₃): 8.49 (m, 2H), 7.45-7.48 (m, 1H), 7.20-7.25 (m, 1H), 6.78 (s, 1H), 6.40-6.59 (m, 1H), 6.18-6.30 (m, 1H), 5.50-5.85 (m, 3H), 4.34-4.48 (m, 1H), 4.15-4.30 (m, 2H), 4.85-4.89 (m, 1H), 3.83 (s 2H), 3.31-3.70 (m, 3H), 2.32 (s, 3H), 2.10-2.15 (m, 1H), 1.80-1.85 (m, 1H).

Example 37: Preparation of(S)-1-(3-((6-((5-methylthiazol-2-yl) amino)-4-(pyridin-2-ylmethyl) pyridin-2-yl) amino) piperidin-1-yl) prop-2-en-1-one

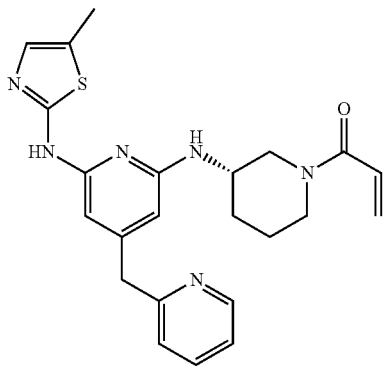 [SMILES: C=CC(=O)N1CCC[C@H](Nc2cc(Cc3ccccn3)cc(Nc3ncc(C)s3)n2)C1]

The title compound (11 mg, yield: 22%) was obtained in the same manner as in Example 36, except that in step 36-1 of Example 36, 2-(bromomethyl) pyridine hydrogen bromide was used instead of 3-(bromomethyl) pyridine hydrogen bromide.

¹H NMR (500 MHZ, CDCl₃): 8.55 (m, 1H), 7.59-7.61 (m, 1H), 7.27-7.35 (m, 2H), 6.90-6.95 (s, 1H), 6.45-6.55 (m, 1H), 6.20-6.25 (m, 1H), 5.95-6.00 (m, 1H), 5.85-5.90 (m, 1H), 5.42-5.48 (m, 1H), 4.18-4.30 (m, 2H), 3.92 (s, 2H), 3.85-3.90 (m, 1H), 3.35-3.40 (m, 2H), 2.37 (s, 3H), 2.01-2.10 (m, 1H), 1.85-1.90 (m, 1H).

Example 38: Preparation of(S)-2-((1-acryloylpiperidin-3-yl) amino)-6-(5-methylthiazol-2-yl) amino) isonicotinonitrile

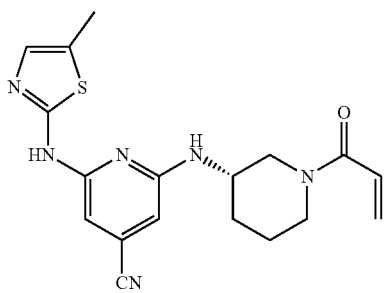 [SMILES: C=CC(=O)N1CCC[C@H](Nc2cc(C#N)cc(Nc3ncc(C)s3)n2)C1]

The title compound (11 mg, yield: 22%) was obtained in the same manner as in Example 1, except that in step 1-3 of Example 1, 2,6-dichloroisonicotinonitrile was used instead of 4-((2,6-dichloropyridin-4-yl) methyl) morpholine.

¹H NMR (500 MHZ, CDCl₃): 6.95-7.02 (m, 1H), 6.20-6.45 (m, 3H), 5.50-5.75 (m, 1H), 4.95-5.05 (m, 1H), 4.17-4.28 (m, 1H), 3.80-4.10 (m, 1H), 3.50-3.78 (m, 3H), 2.37 (s, 3H), 2.10-2.15 (m, 1H), 1.80-1.87 (m, 1H).

Example 39: Preparation of(S)-1-(3-((6-((5-methylthiazol-2-yl) amino)-4-phenylpyridin-2-yl) amino) piperidin-1-yl) prop-2-en-1-one

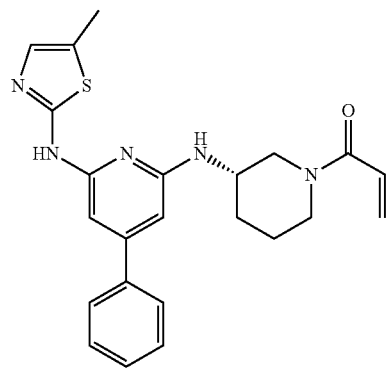 [SMILES: C=CC(=O)N1CCC[C@H](Nc2cc(-c3ccccc3)cc(Nc3ncc(C)s3)n2)C1]

The title compound (10 mg, yield: 22%) was obtained in the same manner as in Example 1, except that in step 1-3 of Example 1, 2,6-dichloro-4-phenylpyridine was used instead of 4-((2,6-dichloropyridin-4-yl) methyl) morpholine.

¹H NMR (500 MHZ, CDCl₃): 7.52-7.60 (m, 2H), 7.35-7.50 (m, 3H), 6.95-7.02 (s, 1H), 6.42-6.50 (m, 1H), 6.17-6.37 (m, 3H), 5.42-5.50 (m, 1H), 4.42-4.50 (m, 1H), 4.28-4.33 (m, 1H), 3.89-3.95 (m, 1H), 3.33-3.50 (m, 2H), 2.30 (s, 3H), 2.05-2.15 (m, 2H), 1.81-1.90 (m, 2H).

Example 40: Preparation of(S)-1-(3-((4-((1-methylpiperidin-4-yl) oxy)-6-((5-methylthiazol-2-yl) amino) pyridin-2-yl) amino) piperidin-1-yl) prop-2-yn-1-one

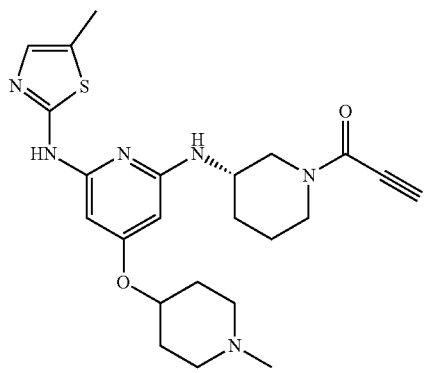 [SMILES: C#CC(=O)N1CCC[C@H](Nc2cc(OC3CCN(C)CC3)cc(Nc3ncc(C)s3)n2)C1]

The title compound (10.0 mg, yield: 8.9%) was obtained in the same manner as in Example 33, except that in step 33-7 of Example 33, propioloyl chloride was used instead of acryloyl chloride.

1H NMR (500 MHZ, CDCl₃): 7.40 (s, 1H), 6.97 (s, 1H), 5.74 (d, 1H), 5.55 (d, 1H), 4.31-4.40 (m, 2H), 4.16-4.21 (m, 1H), 4.24 (d, 1H), 3.82-3.87 (m, 1H), 2.67 (s, 2H), 2.35 (t, 3H), 2.30 (s, 6H), 1.94-1.99 (m, 3H), 1.83-1.89 (m, 4H), 1.65-1.74 (m, 3H)

Example 41: Preparation of (S)-1-(3-((4-((1-methylpiperidin-4-yl) oxy)-6-((5-methylthiazol-2-yl) amino) pyridin-2-yl) amino) piperidin-1-yl) but-2-yn-1-one

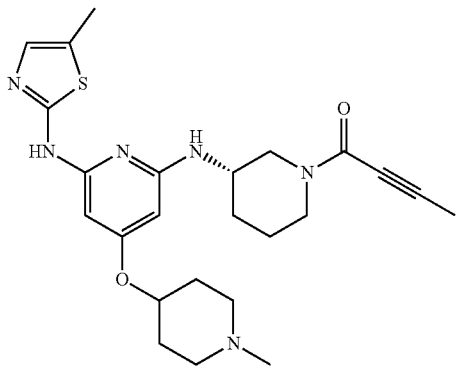 [SMILES: CC#CC(=O)N1CCC[C@H](Nc2cc(OC3CCN(C)CC3)cc(Nc3ncc(C)s3)n2)C1]

The title compound (40.0 mg, yield: 34.4%) was obtained in the same manner as in Example 33, except that in step 33-7 of Example 33, but-2-ynoyl chloride was used instead of acryloyl chloride.

$^1$H NMR (500 MHZ, CDCl$_3$): 10.4 (s, 1H), 6.99 (s, 1H), 5.73 (s, 0.5H), 5.71 (s, 0.5H), 5.55 (d, 0.5H), 5.53 (d, 0.5H), 4.35-4.49 (m, 1H), 4.28-4.29 (m, 1H), 4.24 (d, 1H), 3.82-3.86 (m, 1H), 3.33-3.47 (m, 2H), 2.70 (s, 2H), 2.38 (d, 3H), 2.30 (s, 3H), 2.21-2.26 (m, 3H), 2.09-2.13 (m, 1H), 2.00 (s, 2H), 1.80-1.83 (m, 2H), 1.78 (s, 3H), 1.61-1.67 (m, 2H)

Example 42: Preparation of (S)-1-(3-((4-((4-ethylpiperazin-1-yl) methyl)-6-((5-methylthiazol-2-yl) amino) pyridin-2-yl) amino) piperidin-1-yl) prop-2-en-1-one

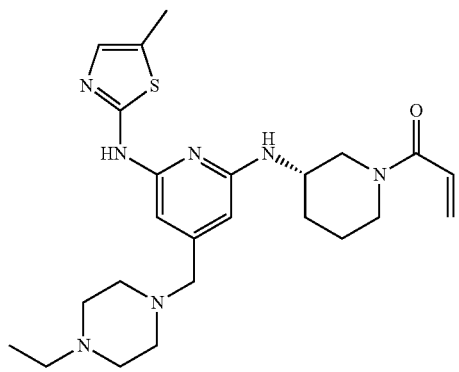 [SMILES: C=CC(=O)N1CCC[C@H](Nc2cc(CN3CCN(CC)CC3)cc(Nc3ncc(C)s3)n2)C1]

The title compound (50.0 mg, yield: 25.0%) was obtained in the same manner as in Example 22, except that in step 22-1 of Example 22, iodoethane was used instead of 1-bromo-2-methoxyethane.

1H NMR (500 MHZ, MeOH): 6.89-6.88 (m, 1H), 6.85-6.45 (m, 1H), 6.20-6.02 (m, 3H), 5.80 (m, 0.5H), 5.45 (m, 0.5H), 4.60 (m, 0.5H), 4.4-4.2 (m, 1H), 4.15-4.00 (1.5H), 3.40 (s, 2H), 2.82-2.80 (m, 2H), 2.50 (m, 7H), 2.40 (m, 2H), 2.27 (s, 3H), 2.20-2.10 (m, 1H), 1.92-1.80 (m, 1H), 1.66-1.59 (m, 3H), 1.10-1.07 (t, 3H)

Example 43: Preparation of (S)-1-(3-((4-((4-methylpiperazin-1-yl) methyl)-6-(5-methylthiazol-2-yl) amino) pyridin-2-yl) amino) piperidin-1-yl) prop-2-en-1-one

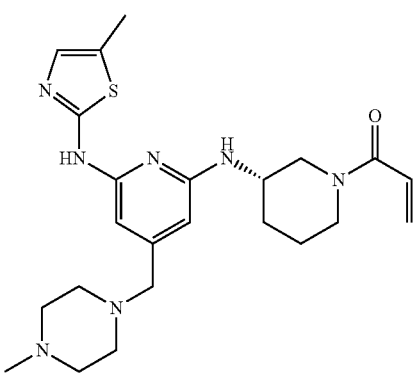 [SMILES: C=CC(=O)N1CCC[C@H](Nc2cc(CN3CCN(C)CC3)cc(Nc3ncc(C)s3)n2)C1]

The title compound (61.0 mg, yield: 21.0%) was obtained in the same manner as in Example 22, except that in step 22-1 of Example 22, iodomethane was used instead of 1-bromo-2-methoxyethane.

1H NMR (500 MHZ, DMSO): 10.53-10.49 (m, 1H), 6.91 (m, 1H), 6.80-6.70 (m, 0.5H), 6.54-6.46 (m, 1.5H), 6.07-5.95 (m, 3H), 5.65-5.63 (m, 0.5H), 5.42-5.40 (m, 0.5H), 4.40-4.50 (m, 0.5H), 4.20-4.00 (m, 1H), 3.90-3.87 (m, 1.5H), 3.26 (s, 2H), 3.12-3.08 (m, 1H), 2.66-2.61 (m, 0.5H), 2.41-2.31 (m, 4H), 2.19 (s, 3H), 2.13 (s, 3H), 2.06-1.97 (m, 3H), 1.81 (m, 1.5H) 1.81 (m, 1H), 1.54-1.44 (m, 2H)

Example 44: Preparation of 5-methyl-N-(6-methyl-4-(morpholinomethyl) pyridin-2-yl) thiazol-2-amine

Step 44-1: Preparation of 4-((2-chloro-6-methylpyridin-4-yl) methyl) morpholine

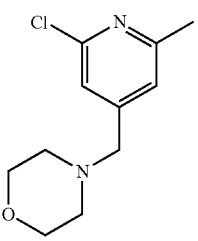

The title compound (112.0 mg, yield: 46%) was obtained in the same manner as in step 1-1, except that in step 1-1 of Example 1, 2-chloro-6-methylisonicotinic acid was used instead of 2,6-dichloroisonicotinic acid.

Step 44-2: Preparation of 5-methyl-N-(6-methyl-4-(morpholinomethyl) pyridin-2-yl) thiazol-2-amine

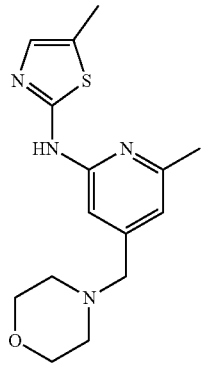 [SMILES: Cc1cc(CN2CCOCC2)cc(Nc2ncc(C)s2)n1]

The title compound (55.0 mg, yield: 54%) was obtained in the same manner as in Step 1-2 of Example 1 by using the intermediate obtained in step 44-1.

1H NMR (500 MHZ, CDCl$_3$): 7.10 (s, 1H), 6.72 (s, 1H), 6.67 (s, 1H), 3.74-3.73 (m, 4H), 3.43 (s, 2H), 2.51 (s, 3H), 2.46 (m, 4H), 2.41 (s, 3H)

Example 45: Preparation of(S)-3-chloro-1-(3-((6-((5-methylthiazol-2-yl) amino)-4-(morpholinomethyl) pyridin-2-yl) amino) piperidin-1-yl) propan-1-one

Step 45-1: Preparation of(S)-1-(3-((6-((5-methylthiazol-2-yl) amino)-4-(morpholinomethyl) pyridin-2-yl) amino) piperidin-1-yl) prop-2-en-1-one hydrochloride

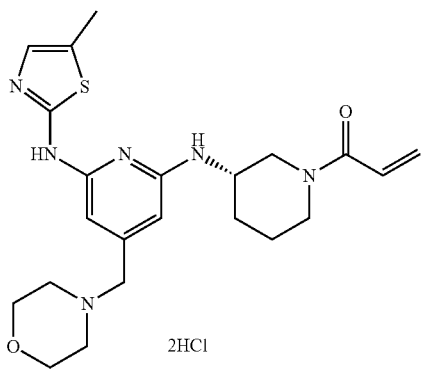 [SMILES: C=CC(=O)N1CCC[C@H](Nc2cc(CN3CCOCC3)cc(Nc3ncc(C)s3)n2)C1]

10.0 g of(S)-1-(3-((6-((5-methylthiazol-2-yl) amino)-4-(morpholinomethyl) pyridin-2-yl) amino) piperidin-1-yl) prop-2-en-1-one as the material of Example 5 was dissolved in 200.0 ml of ethyl acetate, 3 equivalents of 1N-hydrochloric acid dissolved in ethyl acetate was added thereto. The mixture was stirred at room temperature for 1 hour, filtered, and then dried under reduced pressure for 12 hours at room temperature to give(S)-1-(3-((6-((5-methylthiazol-2-yl) amino)-4-(morpholinomethyl) pyridin-2-yl) amino) piperidine-1-yl) prop-2-en-1-one hydrochloride (11.6 g. yield: 85%).

Step 45-2: Preparation of(S)-3-chloro-1-(3-((6-((5-methylthiazol-2-yl) amino)-4-(morpholinomethyl) pyridin-2-yl) amino) piperidin-1-yl) propan-1-one

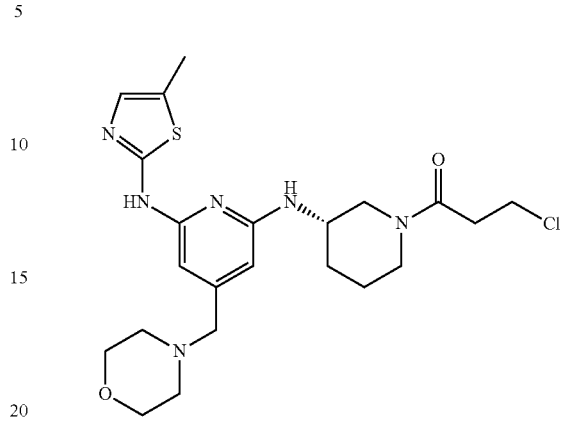

The material obtained in step 45-1 was stored at −20° C. for 7 months. The material produced during the storage process was separated by column using a mixed solvent of methylene chloride and methanol in a ratio of 15:1 to give the title compound (30.0 mg, yield: 5%).

1H NMR (500 MHZ, CDCl$_3$): 7.03-7.0 (d, 1H), 6.17-6.12 (d, 1H), 5.98 (s, 1H), 4.38-4.30 (m, 1H), 4.20-4.11 (m, 2H), 3.88-3.86 (m, 1H), 3.75-3.70 (m, 4H), 3.68-3.56 (m, 1H), 3.43-3.39 (m, 1H), 3.34 (s, 2H), 2.91-2.80 (m, 1H), 2.80-2.71 (m, 1H), 2.62-2.45 (m, 1H), 2.37 (m, 4H), 2.12 (s, 3H), 2.12-2.11 (m, 1H), 2.10-2.12 (m, 1H), 1.90-1.80 (m, 2H)

Example 46: Preparation of (S,E)-3-chloro-1-(3-(6-(5-methylthiazol-2-ylamino)-4-(morpholinomethyl) pyridin-2-ylamino) piperidin-1-yl) prop-2-en-1-one

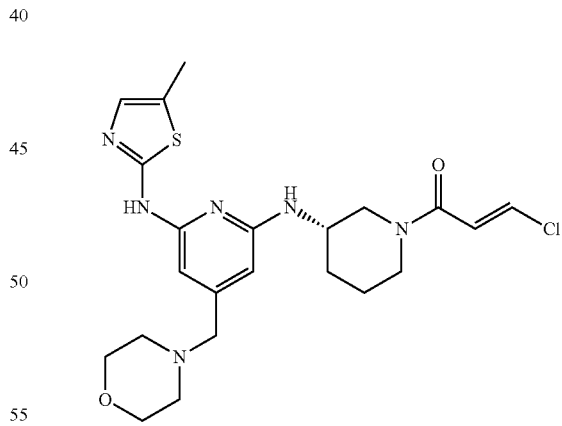

The material obtained in step 45-1 was stored at −20° C. for 7 months. The material produced during the storage process was separated by column using a mixed solvent of methylene chloride and methanol in a ratio of 15:1 to give the title compound (3.0 mg, yield: 0.5%).

1H NMR (500 MHZ, CDCl$_3$): 6.99 (s, 1H), 6.70-6.60 (m, 1H), 6.4-6.2 (m, 2H), 5.8-5.5 (m, 1H), 3.9-3.8 (m, 2H), 3.8-3.7 (m, 4H), 3.6-3.7 (m, 1H), 3.49 (s, 2H), 3.39-3.41 (m, 2H), 2.52 (m, 4H), 2.33 (s, 3H), 1.85-1.82 (m, 2H), 1.68-1.60 (m, 2H)

Example 47: Preparation of(S)-1-(3-(4-((4-(3-aminopropyl) piperazin-1-yl) methyl)-6-(5-methylthiazol-2-vlamino) pyridin-2-vlamino) piperidin-1-yl) prop-2-en-1-one

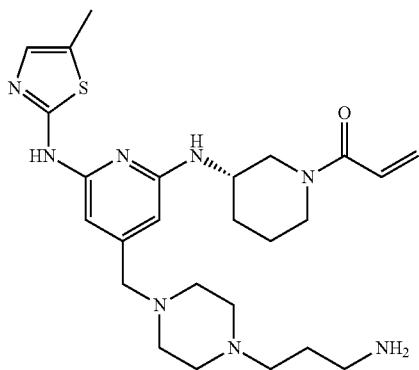 [SMILES: C=CC(=O)N1CCC[C@H](Nc2cc(CN3CCN(CCCN)CC3)cc(Nc3ncc(C)s3)n2)C1]

After(S)-3-(4-((2-((1-acryloylpiperidin-3-yl) amino)-6-((5-methylthiazol-2-yl) amino) pyridin-4-yl) methyl) piperazin-1-yl) propanenitrile (35.0 mg, 1.0 eq) as the material of Example 34 was dissolved in methanol (5.0 mL), 10% palladium/carbon was added thereto at room temperature, and reacted for 5 minutes. Then, the reaction mixture was filtered with methanol using celite. The separated solution was concentrated under reduced pressure and purified by column chromatography to obtain the title compound (4.0 mg, yield: 12.1%) as a brown solid.

1H NMR (500 MHZ, MeOD): 6.57 (s, 1H), 6.53-6.50 (m, 1.5H), 6.08-5.98 (m, 2.5H), 5.67-5.61 (m, 0.5H), 5.42-5.38 (m, 0.5H), 4.48-4.29 (m, 0.5H), 4.20-4.06 (m, 1H), 3.98-3.90 (m, 1.5H), 3.29 (s, 2H), 3.17-3.11 (m, 1H), 2.65-2.62 (m, 2.5H), 2.40-2.36 (m, 6H), 2.23 (s, 3H), 2.06-1.99 (m, 3H), 1.80-1.79 (m, 2.5H), 1.77 (m, 2H) 1.54-1.40 (m, 2H)

Example 48: Preparation of(S)-1-(3-(6-(1H-pyrazol-3-ylamino)-4-(morpholinomethyl) pyridin-2-ylamino) piperidin-1-yl) prop-2-en-1-one Step 48-1: Preparation of tert-butyl(S)-3-((6-((1H-pyrazol-3-yl) amino)-4-(morpholinomethyl) pyridin-2-yl) amino) piperidine-1-carboxylate

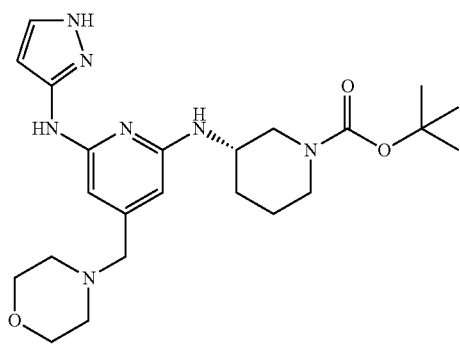 [SMILES: CC(C)(C)OC(=O)N1CCC[C@H](Nc2cc(CN3CCOCC3)cc(Nc3cc[nH]n3)n2)C1]

After(S)-tert-butyl 3-((6-((5-methylthiazol-2-yl) amino)-4-(morpholinomethyl) pyridin-2-yl) amino) piperidine-1-carboxylate (41.0 mg, 1.0 eq) was dissolved in 1,4-dioxane (2.0 mL), tris (dibenzylideneacetone) dipalladium (0) (9.2 mg, 0.1 eq) and (+)-2,2'-bis (diphenylphosphino)-1,1'-binaphthalene (12.5 mg, 0.2 eq) were added thereto. 1H-pyrazol-3-amine (8.3 mg, 1.0 eq) was added and then cesium carbonate (97.7 mg, 3.0 eq) was sequentially added. The mixture was reacted in a microwave reactor at 130° C. for 30 minutes. After cooling to 30° C. or less, water (10.0 mL) and ethyl acetate (10.0 mL) were added, and then the layers were separated. The ethyl acetate layer was dried over anhydrous sodium sulfate and then concentrated under reduced pressure. The resulting residue was purified by column chromatography (ethyl acetate:hexane=1:1) to give the title compound (50.2 mg, yield: 99.8%).

Step 48-2: Preparation of(S)-4-(morpholinomethyl)-$N^2$-(piperidin-3-yl)-$N^6$-(1H-pyrazol-3-yl) pyridin-2,6-diamine

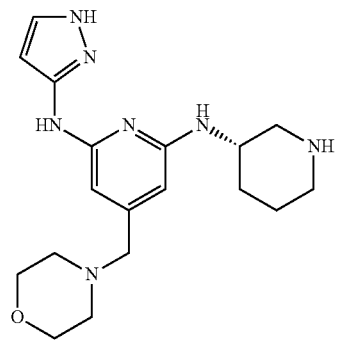 [SMILES: c1cc(Nc2cc(CN3CCOCC3)cc(N[C@H]3CCCNC3)n2)n[nH]1]

After the intermediate (50.0 mg, 1.0 eq) obtained in step 48-1 was dissolved in ethyl acetate (10.0 mL), 6N-hydrochloric acid aqueous solution (0.4 mL, 20.0 eq) was slowly added dropwise, and then stirred for 2 hours. After adjusting the pH to 9~12 using 12N-sodium hydroxide aqueous solution, the separated dichloromethane layer was dried over anhydrous sodium sulfate and then concentrated under reduced pressure. The resulting residue was purified by column chromatography (dichloromethane:methanol=10:1) to give the title compound (34.2 mg, yield: 87.9%).

Step 48-3: Preparation of(S)-1-(3-(6-(1H-pyrazol-3-ylamino)-4-(morpholinomethyl) pyridin-2-ylamino) piperidin-1-yl) prop-2-en-1-one

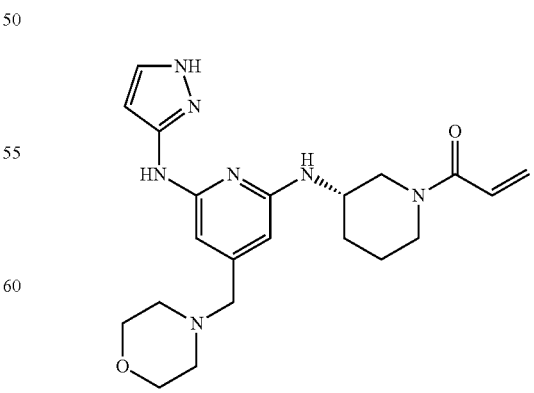

After the intermediate (20.0 mg, 1.0 eq) obtained in step 48-2 was dissolved in tetrahydrofuran (2.0 mL), water (1.0 mL) was added and sodium bicarbonate (14.1 mg, 3.0 eq) was added, and then cooled to 0 to 10° C. Acryloyl chloride (5.6 μl, 1.0 eq) was slowly added dropwise, and then stirred for 30 minutes to complete the reaction. The layers were separated with dichloromethane, and then dried over anhydrous sodium sulfate and concentrated under reduced pressure. The resulting residue was purified by column chromatography (dichloromethane:methanol=15:1) to give the title compound (5.7 mg, yield: 15.4%).

1H NMR (500 MHZ, MeOD): 7.76 (d, 1H), 6.54 (d, 1H), 6.17-6.13 (m, 1H), 6.06 (s, 2H), 6.02-5.92 (m, 1H), 5.50-5.25 (m, 1H), 3.83-3.74 (m, 4H), 3.64 (s, 2H), 2.65-2.27 (m, 4H), 2.12-2.07 (m, 1H), 1.73 (m, 1H), 1.65-1.48 (m, 2H), 1.43-1.20 (m, 5H)

Example 49: Preparation of(S)-1-(3-(4-(morpholinomethyl)-6-(5-(trifluoromethyl) thiazol-2-ylamino) pyridin-2-ylamino) piperidin-1-yl) prop-2-en-1-one Step 49-1: Preparation of tert-butyl(S)-3-((4-(morpholinomethyl)-6-((5-(trifluoromethyl) thiazol-2-yl) amino) pyridin-2-yl) amino) piperidine-1-carboxylate

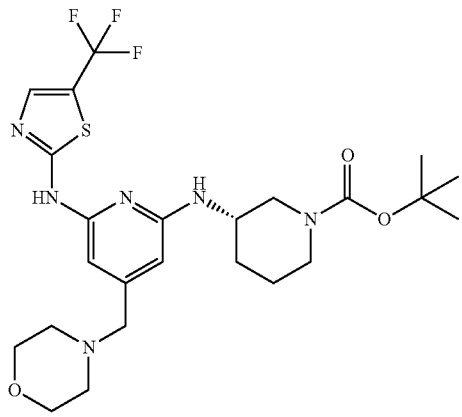 [SMILES: CC(C)(C)OC(=O)N1CCC[C@H](Nc2cc(CN3CCOCC3)cc(Nc3ncc(C(F)(F)F)s3)n2)C1]

After(S)-tert-butyl 3-((6-((5-methylthiazol-2-yl) amino)-4-(morpholinomethyl) pyridin-2-yl) amino) piperidin-1-carboxylate (200.0 mg, 1.0 eq) was dissolved in 1,4-dioxane (2.0 mL), palladium acetate (11.9 mg, 0.1 eq) and Xantphos (56.7 mg, 0.2 eq) were added thereto. 5-(Trifluoromethyl) thiazol-2-amine (81.8 mg, 1.0 eq) and cesium carbonate (476.0 mg, 3.0 eq) was sequentially added. The reactant was allowed to react in a microwave reactor at 150° C. for 1 hour. After cooling to 30° C. or less, water (10.0 mL) and ethyl acetate (10.0 mL) were added, and then the layers were separated. The ethyl acetate layer was dried over anhydrous sodium sulfate and then concentrated under reduced pressure. The resulting residue was purified by column chromatography (ethyl acetate:hexane=1:1) to give the title compound (68.2 mg, yield: 25.8%).

Step 49-2: Preparation of(S)-4-(morpholinomethyl)-N²-(piperidin-3-yl)-N⁶-(5-(trifluoromethyl) thiazol-2-yl) pyridin-2,6-diamine

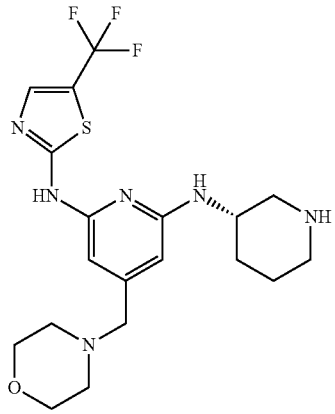 [SMILES: FC(F)(F)c1cnc(Nc2cc(CN3CCOCC3)cc(N[C@H]3CCCNC3)n2)s1]

After the intermediate (50.0 mg, 1.0 eq) obtained in step 48-1 was dissolved in acetate (10.0 mL), 6N-hydrochloric acid aqueous solution (0.4 mL, 20.0 eq) was slowly added dropwise, and then stirred for 2 hours. After adjusting the pH to 9~12 using 12N-sodium hydroxide aqueous solution, the separated dichloromethane layer was dried over anhydrous sodium sulfate and then concentrated under reduced pressure. The resulting residue was purified by column chromatography (dichloromethane:methanol=10:1) to give the title compound (27.0 mg, yield: 44.3%).

Step 49-3: Preparation of(S)-1-(3-(4-(morpholinomethyl)-6-(5-(trifluoromethyl) thiazol-2-ylamino) pyridin-2-ylamino) piperidin-1-yl) prop-2-en-1-one

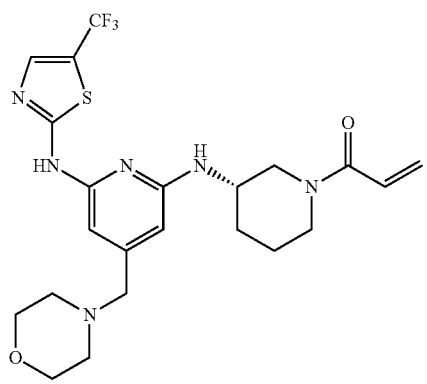 [SMILES: C=CC(=O)N1CCC[C@H](Nc2cc(CN3CCOCC3)cc(Nc3ncc(C(F)(F)F)s3)n2)C1]

After the intermediate (20.0 mg, 1.0 eq) obtained in step 49-2 was dissolved in tetrahydrofuran (2.0 mL), water (1.0 mL) was added and sodium bicarbonate (17.2 mg, 3.0 eq) was added, and then cooled to 0 to 10° C. Acryloyl chloride (4.8 μl, 1.0 eq) was slowly added dropwise, and then stirred for 30 minutes to complete the reaction. The layers were separated, then dried over anhydrous sodium sulfate and concentrated under reduced pressure. The resulting residue was purified by column chromatography (dichloromethane:methanol=15:1) to give the title compound (3.6 mg, yield: 16.0%).

1H NMR (500 MHZ, MeOD): 7.66 (d, 1H), 6.83-6.72 (m, 0.5H), 6.55-6.44 (m, 0.5H), 6.23 (d, 1H), 6.16 (d, 1H), 6.05 (d, 0.5H), 5.73 (d, 0.5H), 5.48 (d, 0.5H), 4.54 (d, 0.5H), 4.43-4.14 (m, 1H), 4.03-3.93 (m, 1.5H), 3.75-3.62 (m, 4H), 3.38 (s, 2H), 3.27-3.18 (m, 1H), 2.86 (t, 0.5H), 2.53-2.38 (m, 4H), 2.28-2.12 (m, 1H), 1.96-1.83 (m, 1H), 1.72-1.49 (m, 2.5H), 1.38-1.23 (m, 1.5H)

Example 50: Preparation of(S)-1-(3-(6-(5-chloro-1H-pyrazol-3-ylamino)-4-(morpholinomethyl) pyridin-2-ylamino) piperidin-1-yl) prop-2-en-1-one

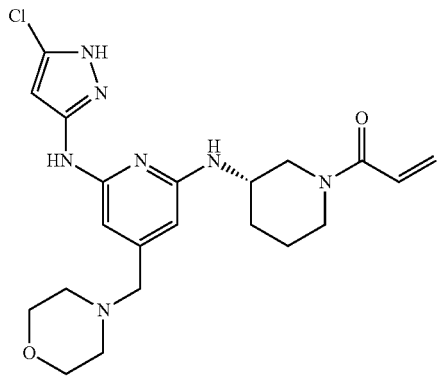 [SMILES: C=CC(=O)N1CCC[C@H](Nc2cc(CN3CCOCC3)cc(Nc3cc(Cl)[nH]n3)n2)C1]

The title compound (14.0 mg, yield: 7.7%) was obtained in the same manner as in Example 48, except that in step 48-1,5-chloro-1H-pyrazol-3-amine was used instead of 1H-pyrazol-3-amine.

1H NMR (500 MHz, MeOD): 6.16-6.14 (m, 1H), 6.13-6.11 (m, 1H), 6.06 (s, 2H), 6.03-6.02 (m, 1H), 5.52-5.50 (m, 1H), 3.73-3.70 (m, 4H), 3.62 (s, 2H), 2.60-2.15 (m, 4H), 2.32-2.06 (m, 1H), 1.72-1.65 (m, 1H), 1.65-1.50 (m, 2H), 1.44-1.25 (m, 5H)

Example 51: Preparation of(S)-1-(3-(4-(morpholinomethyl)-6-(thiazol-2-ylamino) pyridin-2-ylamino) piperidin-1-yl) prop-2-en-1-one

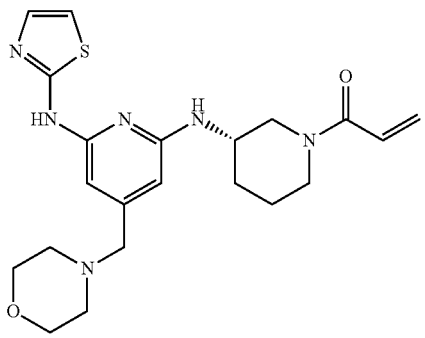 [SMILES: C=CC(=O)N1CCC[C@H](Nc2cc(CN3CCOCC3)cc(Nc3nccs3)n2)C1]

The title compound (3.2 mg, yield: 21.1%) was obtained in the same manner as in Example 49, except that in step 49-1, thiazol-2-amine was used instead of 5-(trifluoromethyl) thiazol-2-amine.

1H NMR (500 MHZ, MeOD): 6.68-6.53 (d, 1H), 6.38-6.30 (d, 2H), 6.17-6.05 (m, 2H), 5.89-5.83 (d, 1H), 5.47-5.43 (m, 0.5H), 5.37-5.32 (m, 0.5H), 3.94-3.87 (m, 1H), 3.80- 3.66 (m, 2H), 3.63-3.48 (m, 2H), 2.58-2.16 (m, 4H), 2.08-1.73 (m, 4H), 1.65-1.55 (m, 2H), 1.41-1.33 (m, 4H)

Example 52: Preparation of(S)-1-(3-(3-fluoro-6-(5-methylthiazol-2-ylamino)-4-(morpholinomethyl) pyridin-2-ylamino) piperidin-1-yl) prop-2-en-1-one Step 52-1: Preparation of (2,6-dichloro-3-fluoropyridin-4-yl) (morpholino) methanone

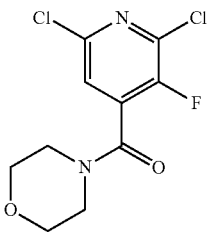 [SMILES: O=C(c1cc(Cl)nc(Cl)c1F)N1CCOCC1]

After 2,6-dichloro-3-fluoronicotinic acid (500.0 mg, 1.0 eq) was dissolved in tetrahydrofuran (15.0 mL), 1,1-carbonyldiimidazole (463.3 mg, 1.2 eq) was added thereto. The mixture was stirred at room temperature (25~30° C.) for 1 hour under nitrogen gas, and then morpholine (0.2 mL, 1.2 eq) was added and stirred at the same temperature for 2 hours to complete the reaction. Ethyl acetate (50.0 mL) and water (50.0 mL) were added thereto, followed by extraction, and the aqueous layer was re-extracted three times using ethyl acetate (50.0 mL). The ethyl acetate layer was dried over anhydrous sodium sulfate and then concentrated under reduced pressure. The resulting residue was purified by column chromatography (ethyl acetate:hexane=1:5) to give the title compound (581.0 mg, 87.5%).

Step 52-2: Preparation of 4-((2,6-dichloro-3-fluoropyridin-4-yl) methyl) morpholine

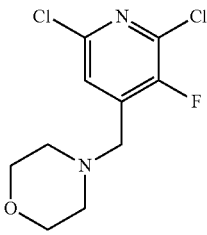 [SMILES: Fc1c(CN2CCOCC2)cc(Cl)nc1Cl]

The intermediate (500.0 mg, 1.0 eq) obtained in step 52-1 was dissolved in dichloromethane (20.0 mL), and then stirred at room temperature (25 to 30° C.). 0.9M borane-tetrahydrofuran (6.0 mL, 3.0 eq) was slowly added dropwise. The mixture was stirred at room temperature for 12 hours to complete the reaction. The reaction solution was cooled to 0 to 10° C., and then 6N-hydrochloric acid aqueous solution (39.0 mL, 20.0 eq) was slowly added dropwise and then stirred at the same temperature for 1 hour. After adjusting the pH to 9 to 12 using 6N-sodium hydroxide aqueous solution, the mixture was extracted twice with dichloromethane. The dichloromethane layer was separated, dried over anhydrous sodium sulfate, and then concentrated under reduced pressure. The resulting residue was purified by column chromatography (ethyl acetate:hexane=1:1) to give the title compound (430.2 mg, yield: 85.9%).

Step 52-3: Preparation of tert-butyl(S)-3-((6-chloro-3-fluoro-4-(morpholinomethyl) pyridin-2-yl) amino) piperidine-1-carboxylate

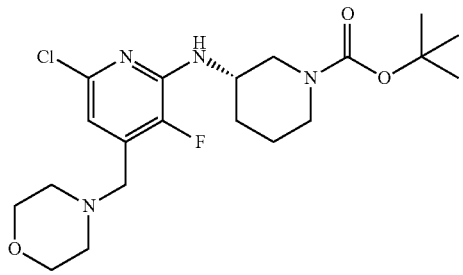 [SMILES: CC(C)(C)OC(=O)N1CCC[C@H](Nc2nc(Cl)cc(CN3CCOCC3)c2F)C1]

To the intermediate (100.0 mg, 1.0 eq) obtained in step 52-2, 1,4-dioxane (2.0 mL) was added and dissolved, and then palladium acetate (9.3 mg, 0.1 eq) and Xantphos (43.4 mg, 0.2 eq) were added thereto. Tert-butyl(S)-3-aminopiperidine-1-carboxylate (75.5 mg, 1.0 eq) was added, and then cesium carbonate (325.8 mg, 3.0 eq) was sequentially added. The mixture was reacted in a microwave reactor at 140° C. for 30 minutes. After cooling to 30° C. or less, water (10.0 mL) and ethyl acetate (10.0 mL) were added, and then the layers were separated. The ethyl acetate layer was dried over anhydrous sodium sulfate and then concentrated under reduced pressure. The resulting residue was purified by column chromatography (ethyl acetate:hexane=1:1) to give the title compound (144.0 mg, yield: 89.4%).

Step 52-4: Preparation of tert-butyl(S)-3-((3-fluoro-6-((5-methylthiazol-2-yl) amino)-4-(morpholinomethyl) pyridin-2-yl) amino) piperidine-1-carboxylate

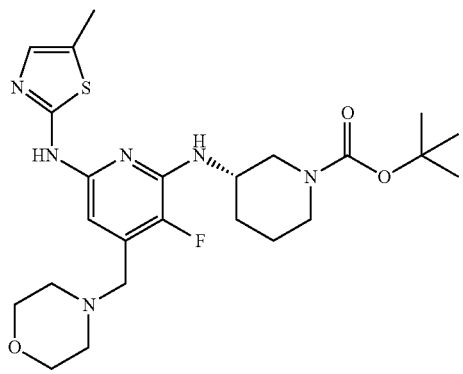 [SMILES: Cc1cnc(Nc2cc(CN3CCOCC3)c(F)c(N[C@H]3CCCN(C(=O)OC(C)(C)C)C3)n2)s1]

The intermediate (100.0 mg, 1.0 eq) obtained in step 52-3 was dissolved in 1,4-dioxane (2.0 mL). Palladium acetate (5.1 mg, 0.1 eq), Xantphos (24.3 mg, 0.2 eq), 5-methyl-thiano-2-amine (24.0 mg, 1.0 eq), and cesium carbonate (205.8 g, 3.0 eq) were sequentially added thereto. The mixture was reacted in a microwave reactor at 150° C. for 30 minutes. After cooling to 30° C. or less, water (10.0 mL) and ethyl acetate (10.0 mL) were added, and then the layers were separated. The ethyl acetate layer was dried over anhydrous sodium sulfate and then concentrated under reduced pressure. The resulting residue was purified by column chromatography (ethyl acetate:hexane=1:1) to give the title compound (86.2 mg, yield: 81.8%).

Step 52-5: Preparation of(S)-3-fluoro-$N^6$-(5-methyl-thiazol-2-yl)-4-(morpholinomethyl)-$N^2$-(piperidin-3-yl) pyridin-2,6-diamine

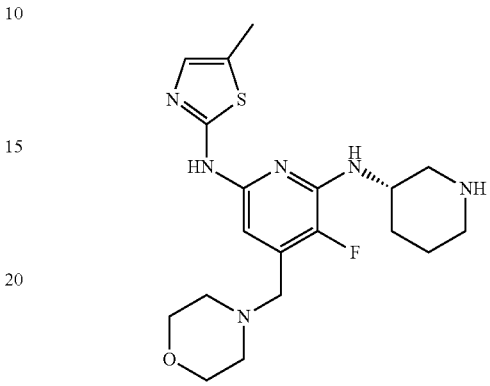

After the intermediate (80.0 mg, 1.0 eq) obtained in step 52-4 was dissolved in ethyl acetate (10.0 mL), 6N-hydrochloric acid aqueous solution (0.6 mL, 20.0 eq) was slowly added dropwise thereto, and then stirred for 2 hours. After adjusting the pH to 9~12 using 12N-sodium hydroxide aqueous solution, the separated dichloromethane layer was dried over anhydrous sodium sulfate and then concentrated under reduced pressure. Ethyl acetate (10.0 mL) was added to the resulting residue and crystals were produced for 30 minutes. The crystals were filtered and then dried to give the title compound (60.5 mg, yield: 99.9%).

Step 52-6: Preparation of(S)-1-(3-(3-fluoro-6-(5-methylthiazol-2-ylamino)-4-(morpholinomethyl) pyridin-2-ylamino) piperidin-1-yl) prop-2-en-1-one

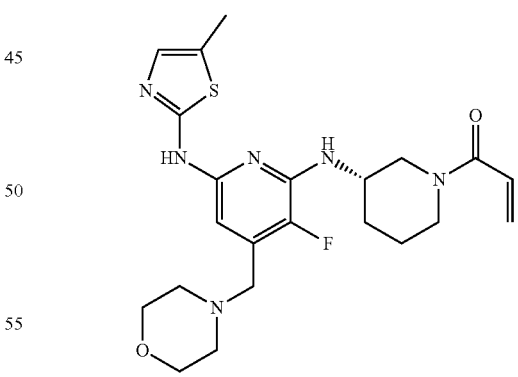

After the intermediate (50.0 mg, 1.0 eq) obtained in step 52-5 was dissolved in tetrahydrofuran (4.0 mL), water (1.0 mL) was added and sodium bicarbonate (31.0 mg, 3.0 eq) was added, and then cooled to 0 to 10° C. Acryloyl chloride (9.9 μl, 1.0 eq) was slowly added dropwise, and then stirred for 30 minutes to complete the reaction. The layers were separated with dichloromethane, dried over anhydrous sodium sulfate and concentrated under reduced pressure. The resulting residue was purified by column chromatography (dichloromethane:methanol=15:1) to give the title compound (26.5 mg, yield: 46.8%).

1H NMR (500 MHZ, MeOD): 6.88-6.80 (m, 1H), 6.65 (m, 1H), 6.21-6.15 (m, 1H), 5.68 (d, 1H), 5.37-5.28 (m, 1H), 3.72-3.65 (m, 4H), 3.53-3.48 (s, 3H), 2.76-2.69 (m, 2H), 2.52-2.42 (m, 4H), 2.28-2.14 (m, 3H), 2.12-1.98 (m, 2H), 1.66-1.53 (m, 4H)

Example 53: Preparation of(S)-1-(3-(4-(morpholinomethyl)-6-(pyridin-2-ylamino) pyridin-2-ylamino) piperidin-1-yl) prop-2-en-1-one

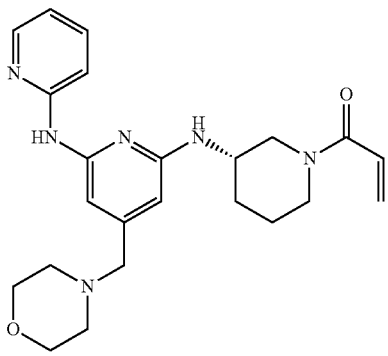 [SMILES: C=CC(=O)N1CCC[C@H](Nc2cc(CN3CCOCC3)cc(Nc3ccccn3)n2)C1]

The title compound (11.0 mg, yield: 31.0%) was obtained in the same manner as in Example 48, except that in step 48-1, pyridin-2-amine was used instead of 1H-pyrazol-3-amine.

1H NMR (500 MHZ, MeOD): 8.50-8.45 (t, 2H), 7.51 (d, 1H), 6.80-6.75 (m, 1H), 6.70-6.62 (m, 0.5H), 6.24-6.16 (m, 1.5H), 6.14-6.08 (d, 0.5H), 5.77-5.51 (m, 0.5H), 4.03-3.92 (m, 1H), 3.91-3.77 (m, 2H), 3.74-3.65 (m, 4H), 3.42-3.37 (m, 3H), 3.26-3.18 (m, 0.5H), 2.81-2.74 (m, 0.5H), 2.54-2.40 (m, 4H), 2.12-1.98 (m, 1H), 1.89-1.81 (m, 1H)

Example 54: Preparation of(S)-1-(3-(4-(morpholinomethyl)-6-(pyrimidin-2-ylamino) pyridin-2-ylamino) piperidin-1-yl) prop-2-en-1-one

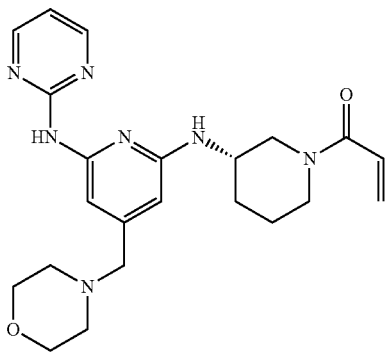 [SMILES: C=CC(=O)N1CCC[C@H](Nc2cc(CN3CCOCC3)cc(Nc3ncccn3)n2)C1]

The title compound (24.2 mg, 24.3%) was obtained in the same manner as in Example 1, except that in step 48-1, pyrimidine-2-amine was used instead of 1H-pyrazol-3-amine.

1H NMR (500 MHZ, MeOD): 8.15-8.10 (m, 1H), 7.80 (d, 1H), 7.62-7.56 (m, 1H), 6.86-6.80 (m, 1H), 6.58-6.45 (m, 1.5H), 6.24-6.19 (m, 0.5H), 6.09 (m, 1H), 6.06-6.00 (m, 0.5H), 5.79-5.73 (m, 0.5H), 4.01-3.80 (m, 4H) 3.73-3.65 (m, 4H), 3.36 (s, 2H), 2.52-2.41 (m, 4H), 2.14-2.304 (m, 1H), 1.94-1.86 (m, 2H), 1.73-1.56 (m, 2H)

Experimental Example: Inhibitory Activity Against BTK and ITK

Inhibitory activities against BTK and ITK were measured for the compounds prepared in the above Examples as follows.

The inhibitory activities against BTK were evaluated using 'ADP-Glo™+BTK Kinase enzyme system' kit (Promega Corporation). In a white 96-well plate, 10 μl of BTK enzyme prepared so as to have a final concentration of 1 ng/μl was mixed with 5 μl of compounds having a final concentration of 1 uM in the case of evaluating a single concentration of compound and a concentration of 1000, 300, 100, 30, 10, 3, 1, 0.3, 0.1 and 0.03 nM in the case of $IC_{50}$ evaluation, and then reacted at room temperature for 15 minutes. 5 μl of substrate and 5 μl of ATP prepared so as to have a final concentration of 10 UM were added to the plate on which reactions were completed, and then allowed to react at 30° C. for 1 hour. All wells of the plate were treated with 25 μl of ADP-Glo™ reagent and allowed to react at 30° C. for 40 minutes. After that, all wells were treated with 50 μl of kinase detection buffer, and then reacted at 30° C. for 30 minutes under light shielding conditions. For the plate on which all reactions were completed, luminescence was measured and the results were calculated. Evaluation was carried out in duplicate, and negative control and positive control were calculated depending on whether or not the enzyme was added without treatment of the compound. The $IC_{50}$ was calculated based on the calculated values.

The inhibitory activity against ITK was evaluated using 'ADP-Glo™+ITK Kinase enzyme system' kit (Promega Corporation). In a white 96-well plate, 10 μl of ITK enzyme prepared so as to have a final concentration of 0.4 ng/μl was mixed with 5 μl of compounds having a final concentration of 1 uM in the case of evaluating a single concentration of compound and a concentration of 1000, 300, 100, 30, 10, 3, 1, 0.3, 0.1 and 0.03 nM in the case of $IC_{50}$ evaluation, and then reacted at room temperature for 15 minutes. To the plate on which reactions were completed, 5 μl of substrate and 5 μl of ATP prepared so as to have a final concentration of 25 μl were added and then allowed to react at 30° C. for 1 hour. All wells of the plate were treated with 25 μl of ADP-Glo™ reagent and then allowed to react at 30° C. for 40 minutes. After that, all wells were treated with 50 μl of kinase detection buffer, and then allowed to react at 30° C. for 30 minutes under light shielding conditions. For the plate on which all reactions were completed, luminescence was measured and the results were calculated. Evaluation was carried out in duplicate, and negative control and positive control were calculated depending on whether or not the enzyme was added without treatment of the compound. The $IC_{50}$ was calculated based on the calculated values. The results are shown in Table 1 below.

TABLE 1

| Example No. | Inhibitory activity | |
|---|---|---|
| | ITK $IC_{50}$ (nM) | BTK $IC_{50}$ (nM) |
| 1 | 4.1 | 4.7 |
| 2 | 2.6 | 3.1 |

TABLE 1-continued

| Example No. | Inhibitory activity | |
|---|---|---|
| | ITK IC$_{50}$ (nM) | BTK IC$_{50}$ (nM) |
| 3 | 9.1 | 10.3 |
| 4 | 1.6 | 0.4 |
| 5 | >200 | 151.6 |
| 6 | 36.0 | 27.7 |
| 7 | 3.5 | 3.6 |
| 8 | 71.7 | 72.5 |
| 9 | >1000 | >1000 |
| 10 | >40 | 2.4 |
| 11 | 7.8 | 8.5 |
| 12 | 2 | 2 |
| 13 | >200 | >200 |
| 14 | 49.1 | 3.3 |
| 15 | 47.3 | 2.3 |
| 16 | >1000 | 1.1 |
| 17 | 1.9 | 1.5 |
| 18 | 50.5 | 5.2 |
| 19 | 200.0 | 875.3 |
| 20 | 1.1 | 1.1 |
| 21 | 1.9 | 1.3 |
| 22 | 1.0 | 1.2 |
| 23 | 200.0 | 36.6 |
| 24 | 2.3 | 2.2 |
| 25 | ~1000 | ~1000 |
| 26 | 17.7 | 2.2 |
| 27 | 43.8 | 85.2 |
| 28 | 31.7 | 8.8 |
| 29 | 50.4 | 18.5 |
| 30 | 47.0 | 67.1 |
| 31 | 15.6 | 8.8 |
| 32 | 5.6 | 3 |
| 33 | 3.9 | 1.8 |
| 34 | 1.7 | 1.1 |
| 35 | 13.4 | 2.1 |
| 36 | 1.8 | 3.9 |
| 37 | 1.9 | 3.2 |
| 38 | 2.6 | 1.6 |
| 39 | 4.8 | 7.5 |
| 40 | 10.8 | 10.3 |
| 41 | 128.0 | 9.5 |
| 42 | 2.2 | 2.5 |
| 43 | 2.1 | 1.6 |
| 44 | ~1000 | >1000 |
| 45 | 91.6 | 30.8 |
| 46 | 31.8 | 5.2 |
| 47 | 9.0 | 6.1 |
| 48 | ~1000 | ~1000 |
| 49 | 3.0 | 2.0 |
| 50 | ~1000 | ~1000 |
| 51 | ~1000 | ~1000 |
| 52 | ~1000 | ~1000 |
| 53 | 42.8 | 7.7 |
| 54 | ~1000 | ~1000 |

The invention claimed is:

1. A compound represented by the following Chemical Formula 1, or a pharmaceutically acceptable salt thereof:

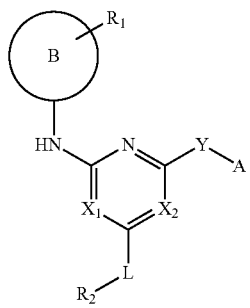

[Chemical Formula 1]

wherein, in Chemical Formula 1,

B is a 5-membered or 6-membered heterocycle containing 1 to 3 heteroatoms each independently selected from the group consisting of N, O and S, provided that the 5-membered or 6-membered heterocycle includes at least one N, $R_1$ is hydrogen, halogen, $C_{1-4}$ alkyl, or $C_{1-4}$ haloalkyl, $X_1$ and $X_2$ are each CH, L is $C_{1-4}$ alkylene or —O—, $R_2$ is pyridinyl; morpholino; piperazinyl; or piperidinyl, wherein, the piperazinyl and the piperidinyl are each independently unsubstituted or substituted with $C_{1-4}$ alkyl, $C_{1-4}$ alkyl substituted with cyano, $C_{1-4}$ alkyl substituted with amino, $C_{1-4}$ alkyl substituted with $C_{1-4}$ alkoxy, or —CO—($C_{1-4}$ alkyl), Y is —O—, —NH—, or —N($C_{1-4}$ alkyl)-, and A is

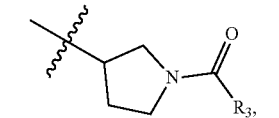

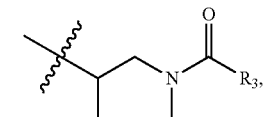

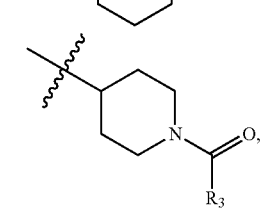

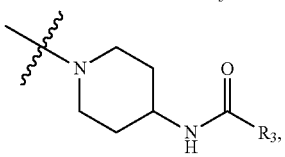

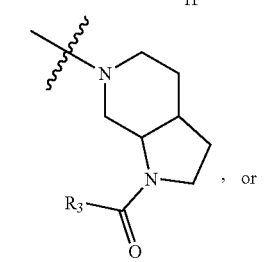

, or

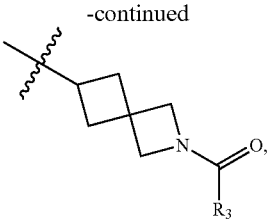

wherein $R_3$ is $C_{1-4}$ alkyl, $C_{1-4}$ haloalkyl, $C_{2-4}$ alkenyl, $C_{2-4}$ haloalkenyl, $C_{2-4}$ alkynyl, or $C_{2-4}$ haloalkynyl.

2. The compound or a pharmaceutically acceptable salt thereof according to claim 1, wherein B is a thiazole, pyrazole, pyridine, or pyrimidine ring, and $R_1$ is hydrogen, chloro, methyl, or trifluoromethyl.

3. The compound or a pharmaceutically acceptable salt thereof according to claim 1, wherein L is methylene or —O—.

4. The compound or a pharmaceutically acceptable salt thereof according to claim 1, wherein $R_2$ is pyridinyl; morpholino; piperazinyl substituted with methyl; piperazinyl substituted with ethyl; piperazinyl substituted with 2-cyanoethyl; piperazinyl substituted with 3-aminopropyl; piperazinyl substituted with 2-methoxyethyl; piperazinyl substituted with —CO-(methyl); unsubstituted piperidinyl; or piperidinyl substituted with methyl.

5. The compound or a pharmaceutically acceptable salt thereof according to claim 1, wherein Y is —O—, —NH—, or —N(methyl)-.

6. The compound or a pharmaceutically acceptable salt thereof according to claim 1, wherein $R_3$ is —$CH_2CH_2Cl$, —$CH=CH_2$, —$CH=CHCH_3$, —$CH=CHCl$, —$C\equiv CH$, or —$C\equiv CCH_3$.

7. The compound or a pharmaceutically acceptable salt thereof according to claim 1, wherein the compound represented by Chemical Formula 1 is represented by the following Chemical Formula 1-1:

[Chemical Formula 1-1]

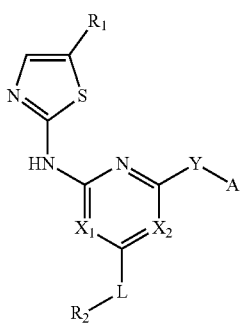

wherein, in Chemical Formula 1-1,
$R_1$ is hydrogen, $C_{1-4}$ alkyl, or $C_{1-4}$ haloalkyl,
$X_1$ and $X_2$ are each CH,
L is $C_{1-4}$ alkylene or —O—,
$R_2$ is pyridinyl; morpholino; piperazinyl; or piperidinyl,
wherein the piperazinyl and piperidinyl are each independently unsubstituted or substituted with $C_{1-4}$ alkyl, $C_{1-4}$ alkyl substituted with cyano, $C_{1-4}$ alkyl substituted with amino, $C_{1-4}$ alkyl substituted with $C_{1-4}$ alkoxy, or —CO—($C_{1-4}$ alkyl),
Y is —O—, —NH—, or —N($C_{1-4}$ alkyl)-, and
A is

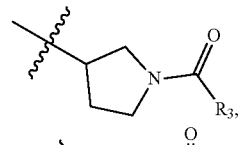

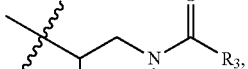

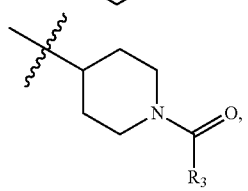

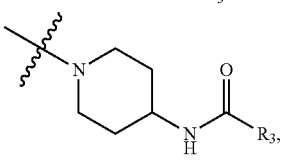

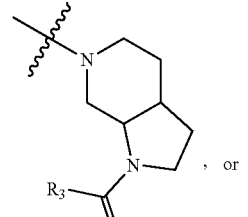

, or

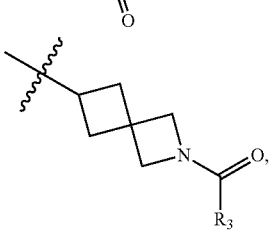

wherein $R_3$ is $C_{1-4}$ haloalkyl, $C_{2-4}$ alkenyl, $C_{2-4}$ haloalkenyl, or $C_{2-4}$ alkynyl, or a pharmaceutically acceptable salt thereof.

8. The compound or a pharmaceutically acceptable salt thereof according to claim 7, wherein
$R_1$ is $C_{1-4}$ alkyl,
$X_1$ and $X_2$ are each CH,
L is $C_{1-4}$ alkylene or —O—,
$R_2$ is pyridinyl; morpholino; piperazinyl; or piperidinyl,
wherein the piperazinyl and piperidinyl are each independently unsubstituted or substituted with $C_{1-4}$ alkyl, $C_{1-4}$ alkyl substituted with cyano, $C_{1-4}$ alkyl substituted with $C_{1-4}$ alkoxy, or —CO—($C_{1-4}$ alkyl),
Y is —O—, —NH—, or —N($C_{1-4}$ alkyl)-, and
A is

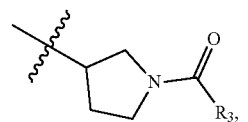

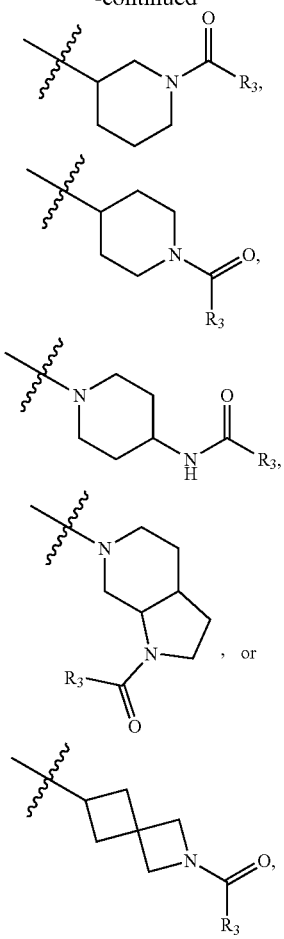

wherein $R_3$ is $C_{2-4}$ alkenyl, or $C_{2-4}$ alkynyl.

9. The compound or a pharmaceutically acceptable salt thereof according to claim 1, wherein the compound represented by Chemical Formula 1 is represented by the following Chemical Formula 1-2:

[Chemical Formula 1-2]

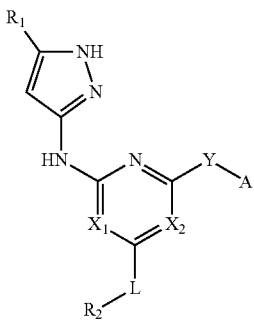

wherein, in Chemical Formula 1-2,
$R_1$ is hydrogen or halogen,
$X_1$ and $X_2$ are each CH,
L is $C_{1-4}$ alkylene,
$R_2$ is morpholino,
Y is —NH—,
A is

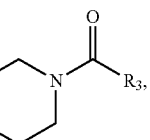

wherein $R_3$ is $C_{2-4}$ alkenyl,
or a pharmaceutically acceptable salt thereof.

10. The compound or a pharmaceutically acceptable salt thereof according to claim 1, wherein the compound represented by Chemical Formula 1 is represented by the following Chemical Formula 1-3:

[Chemical Formula 1-3]

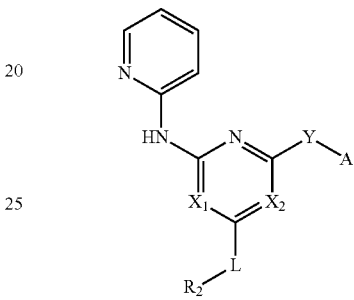

wherein, in Chemical Formula 1-3,
$X_1$ and $X_2$ are each CH,
L is $C_{1-4}$ alkylene,
$R_2$ is morpholino,
Y is —NH—,
A is

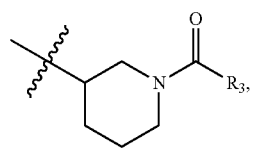

wherein $R_3$ is $C_{2-4}$ alkenyl,
or a pharmaceutically acceptable salt thereof.

11. The compound or a pharmaceutically acceptable salt thereof according to claim 1, wherein the compound represented by Chemical Formula 1 is represented by the following Chemical Formula 1-4:

[Chemical Formula 1-4]

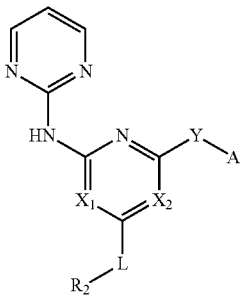

wherein, in Chemical Formula 1-4,
$X_1$ and $X_2$ are each CH,
L is $C_{1-4}$ alkylene,
$R_2$ is morpholino,
Y is —NH—,
A is

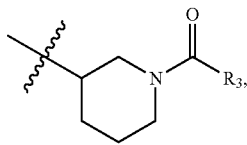

wherein $R_3$ is $C_{2-4}$ alkenyl,
or a pharmaceutically acceptable salt thereof.

12. A compound selected from the group consisting of:
1) 1-(3-((6-((5-methylthiazol-2-yl) amino)-4-(morpholinomethyl) pyridin-2-yl) amino) piperidin-1-yl) prop-2-en-1-one,
2) 1-(3-((6-((5-methylthiazol-2-yl) amino)-4-(morpholinomethyl) pyridin-2-yl) amino) pyrrolidin-1-yl) prop-2-en-1-one,
3) 1-(4-((6-((5-methylthiazol-2-yl) amino)-4-(morpholinomethyl) pyridin-2-yl) amino) piperidin-1-yl) prop-2-en-1-one,
4) (R)-1-(3-((6-((5-methylthiazol-2-yl) amino)-4-(morpholinomethyl) pyridin-2-yl) amino) piperidin-1-yl) prop-2-en-1-one,
5) (S)-1-(3-((6-((5-methylthiazol-2-yl) amino)-4-(morpholinomethyl) pyridin-2-yl) amino) piperidin-1-yl) prop-2-en-1-one,
6) (R)-1-(3-((6-((5-methylthiazol-2-yl) amino)-4-(morpholinomethyl) pyridin-2-yl) amino) pyrrolidin-1-yl) prop-2-en-1-one,
7) (S)-1-(3-((6-((5-methylthiazol-2-yl) amino)-4-(morpholinomethyl) pyridin-2-yl) amino) pyrrolidin-1-yl) prop-2-en-1-one,
10) 1-(3-((6-((5-methylthiazol-2-yl) amino)-4-(morpholinomethyl) pyridin-2-yl) oxy) pyrrolidin-1-yl) prop-2-en-1-one,
11) 1-(4-((6-((5-methylthiazol-2-yl) amino)-4-(morpholinomethyl) pyridin-2-yl) oxy) piperidin-1-yl) prop-2-en-1-one,
12) 1-(3-((6-((5-methylthiazol-2-yl) amino)-4-(morpholinomethyl) pyridin-2-yl) oxy) piperidin-1-yl) prop-2-en-1-one,
13) (R)-1-(3-((6-((5-methylthiazol-2-yl) amino)-4-(morpholinomethyl) pyridin-2-yl) amino) piperidin-1-yl) but-2-yn-1-one,
14) 1-(3-((6-((5-methylthiazol-2-yl) amino)-4-(morpholinomethyl) pyridin-2-yl) amino) pyrrolidin-1-yl) but-2-yn-1-one,
15) (S)-1-(3-((6-((5-methylthiazol-2-yl) amino)-4-(morpholinomethyl) pyridin-2-yl) oxy) piperidin-1-yl) prop-2-en-1-one,
18) (S)-1-(3-((6-((5-methylthiazol-2-yl) amino)-4-(morpholinomethyl) pyridin-2-yl) amino) piperidin-1-yl) but-2-yn-1-one,
19) 1-(4-((6-((5-methylthiazol-2-yl) amino)-4-(morpholinomethyl) pyridin-2-yl) amino) piperidin-1-yl) but-2-yn-1-one,
20) (S)-1-(3-((4-((4-acetylpiperazin-1-yl) methyl)-6-(5-methylthiazol-2-yl) amino) pyridin-2-yl) amino) piperidin-1-yl) prop-2-en-1-one,
26) (S)-1-(3-(methyl (6-((5-methylthiazol-2-yl) amino)-4-(morpholinomethyl) pyridin-2-yl) amino) piperidin-1-yl) prop-2-en-1-one,
30) 1-(6-(((6-((5-methylthiazol-2-yl) amino)-4-(morpholinomethyl) pyridin-2-yl) amino)-2-azaspiro[3.3] heptan-2-yl) prop-2-en-1-one,
33) (S)-1-(3-((4-((1-methylpiperidin-4-yl) oxy)-6-((5-methylthiazol-2-yl) amino) pyridin-2-yl) amino) piperidin-1-yl) prop-2-en-1-one,
34) (S)-3-(4-((2-((1-acryloylpiperidin-3-yl) amino)-6-((5-methylthiazol-2-yl) amino) pyridin-4-yl) methyl) piperazin-1-yl) propanenitrile,
36) (S)-1-(3-((6-((5-methylthiazol-2-yl) amino)-4-(pyridin-3-ylmethyl) pyridin-2-yl) amino) piperidin-1-yl) prop-2-en-1-one,
37) (S)-1-(3-((6-((5-methylthiazol-2-yl) amino)-4-(pyridin-2-ylmethyl) pyridin-2-yl) amino) piperidin-1-yl) prop-2-en-1-one,
40) (S)-1-(3-((4-((1-methylpiperidin-4-yl) oxy)-6-((5-methylthiazol-2-yl) amino) pyridin-2-yl) amino) piperidin-1-yl) prop-2-yn-1-one,
41) (S)-1-(3-((4-((1-methylpiperidin-4-yl) oxy)-6-((5-methylthiazol-2-yl) amino) pyridin-2-yl) amino) piperidin-1-yl) but-2-yn-1-one,
42) (S)-1-(3-((4-((4-ethylpiperazin-1-yl) methyl)-6-((5-methylthiazol-2-yl) amino) pyridin-2-yl) amino) piperidin-1-yl) prop-2-en-1-one,
43) (S)-1-(3-((4-((4-methylpiperazin-1-yl) methyl)-6-(5-methylthiazol-2-yl) amino) pyridin-2-yl) amino) piperidin-1-yl) prop-2-en-1-one,
45) (S)-3-chloro-1-(3-((6-((5-methylthiazol-2-yl) amino)-4-(morpholinomethyl) pyridin-2-yl) amino) piperidin-1-yl) propan-1-one,
46) (S,E)-3-chloro-1-(3-(6-(5-methylthiazol-2-ylamino)-4-(morpholinomethyl) pyridin-2-ylamino) piperidin-1-yl) prop-2-en-1-one,
47) (S)-1-(3-(4-((4-(3-aminopropyl) piperazin-1-yl) methyl)-6-(5-methylthiazol-2-ylamino) pyridin-2-ylamino) piperidin-1-yl) prop-2-en-1-one,
49) (S)-1-(3-(4-(morpholinomethyl)-6-(5-(trifluoromethyl) thiazol-2-ylamino) pyridin-2-ylamino) piperidin-1-yl) prop-2-en-1-one,
53) (S)-1-(3-(4-(morpholinomethyl)-6-(pyridin-2-ylamino) pyridin-2-ylamino) piperidin-1-yl) prop-2-en-1-one, and pharmaceutically acceptable salts of any of the foregoing.

13. A pharmaceutical composition comprising the compound according to claim 1 or a pharmaceutically acceptable salt thereof as an active ingredient and one or more pharmaceutically acceptable carriers or diluents.

14. A compound represented by the following Chemical Formula 1, or a pharmaceutically acceptable salt thereof:

[Chemical Formula 1]

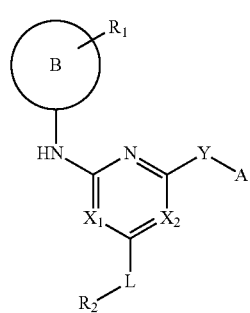

wherein, in Chemical Formula 1,
B is a thiazole ring,
$R_1$ is $C_{1-4}$ alkyl,
$X_1$ and $X_2$ are CH,
L is methylene,
$R_2$ is morpholino; piperazinyl substituted with ethyl; or unsubstituted piperidinyl,
Y is —O— or —NH—, and
A is

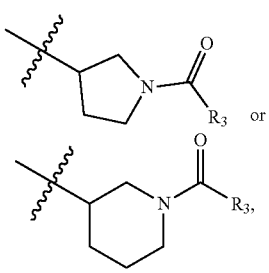

wherein $R_3$ is $C_{2-4}$ alkenyl or $C_{2-4}$ alkynyl.

15. A compound or a pharmaceutically acceptable salt thereof, wherein the compound is:
1) 1-(3-((6-((5-methylthiazol-2-yl) amino)-4-(morpholinomethyl) pyridin-2-yl) amino) piperidin-1-yl) prop-2-en-1-one.

16. A pharmaceutical composition comprising the compound according to claim 12 or a pharmaceutically acceptable salt thereof as an active ingredient and one or more pharmaceutically acceptable carriers or diluents.

17. A pharmaceutical composition comprising the compound according to claim 14 or a pharmaceutically acceptable salt thereof as an active ingredient and one or more pharmaceutically acceptable carriers or diluents.

18. A pharmaceutical composition comprising the compound according to claim 15 or a pharmaceutically acceptable salt thereof as an active ingredient and one or more pharmaceutically acceptable carriers or diluents.

* * * * *

UNITED STATES PATENT AND TRADEMARK OFFICE
CERTIFICATE OF CORRECTION

PATENT NO. : 12,227,498 B2
APPLICATION NO. : 17/269325
DATED : February 18, 2025
INVENTOR(S) : Wol Young Kim et al.

Page 1 of 1

It is certified that error appears in the above-identified patent and that said Letters Patent is hereby corrected as shown below:

In the Claims

At Column 73, Line 39, "alkenyl," should be -- alkenyl --.

Signed and Sealed this
Fifteenth Day of July, 2025

Coke Morgan Stewart
*Acting Director of the United States Patent and Trademark Office*